(12) United States Patent
Boudreaux et al.

(10) Patent No.: US 10,806,478 B2
(45) Date of Patent: Oct. 20, 2020

(54) METHODS FOR ASSEMBLING SURGICAL INSTRUMENTS

(71) Applicant: Ethicon LLC, Guaynabo, PR (US)

(72) Inventors: Chad P. Boudreaux, Cincinnati, OH (US); Jason R. Lesko, Cincinnati, OH (US); Eric N. Johnson, Maineville, OH (US); Kevin M. Fiebig, Cincinnati, OH (US); Carl J. Draginoff, Jr., Mason, OH (US); Scott B. Killinger, Madeira, OH (US); Kris E. Kallenberger, Cincinnati, OH (US); Barry C. Worrell, Centerville, OH (US)

(73) Assignee: Ethicon LLC, Guaynabo, PR (US)

( * ) Notice: Subject to any disclaimer, the term of this patent is extended or adjusted under 35 U.S.C. 154(b) by 7 days.

(21) Appl. No.: 16/185,382

(22) Filed: Nov. 9, 2018

(65) Prior Publication Data

US 2019/0076159 A1     Mar. 14, 2019

Related U.S. Application Data

(62) Division of application No. 14/658,944, filed on Mar. 16, 2015, now Pat. No. 10,159,506.

(51) Int. Cl.
*A61B 17/295*    (2006.01)
*A61B 18/14*     (2006.01)
(Continued)

(52) U.S. Cl.
CPC ............ *A61B 17/295* (2013.01); *A61B 17/29* (2013.01); *A61B 18/1445* (2013.01);
(Continued)

(58) Field of Classification Search
CPC .................. A61B 17/295; A61B 17/29; A61B 2017/2919; A61B 2017/294;
(Continued)

(56) References Cited

U.S. PATENT DOCUMENTS 4,203,430 A   5/1980   Takahashi
5,254,088 A   10/1993  Lundquist et al.
(Continued)

FOREIGN PATENT DOCUMENTS

EP    2044893 A2    4/2009

OTHER PUBLICATIONS

International Search Report for Application No. PCT/US2016/020078 dated Apr. 21, 2016 (4 pages).
(Continued)

*Primary Examiner* — Jermie E Cozart
(74) *Attorney, Agent, or Firm* — Mintz Levin Cohn Ferris Glovsky and Popeo, P.C.

(57) ABSTRACT

Various exemplary methods and devices for actuating surgical instruments are provided. In general, a surgical device can include one or more actuation shafts configured to facilitate actuation of the device. In an exemplary embodiment, the device can include four actuation shafts, two actuation shafts to facilitate articulation of the device, one actuation shaft to facilitate opening and closing of jaws at a distal end of the device, and one actuation shaft to facilitate moving a cutting element of the device. In an exemplary embodiment, each of the one or more actuation shafts can include a distal elongate member and a proximal elongate member having a proximal end attached to a distal end of the distal elongate member. The proximal elongate member can be rigid, and the distal elongate member can be flexible.

5 Claims, 39 Drawing Sheets

(51) Int. Cl.
*A61B 17/29* (2006.01)
*A61B 18/00* (2006.01)
*A61B 17/00* (2006.01)

(52) U.S. Cl.
CPC ............... *A61B 2017/00526* (2013.01); *A61B 2017/294* (2013.01); *A61B 2017/2905* (2013.01); *A61B 2017/2912* (2013.01); *A61B 2017/2927* (2013.01); *A61B 2018/0063* (2013.01); *A61B 2018/00601* (2013.01); *A61B 2018/1455* (2013.01); *Y10T 29/49863* (2015.01)

(58) Field of Classification Search
CPC ...... A61B 18/1445; A61B 2017/00526; A61B 2017/2905; A61B 2017/2912; A61B 2017/2927; Y10T 29/49863
See application file for complete search history.

(56) References Cited

U.S. PATENT DOCUMENTS

| | | |
|---|---|---|
| 5,632,432 A | 5/1997 | Schulze et al. |
| 2002/0038116 A1 | 3/2002 | Lee et al. |
| 2003/0036748 A1 | 2/2003 | Cooper et al. |
| 2003/0045900 A1 | 3/2003 | Hahnen et al. |
| 2004/0236316 A1 | 11/2004 | Danitz et al. |
| 2007/0175949 A1 | 8/2007 | Shelton et al. |
| 2007/0250113 A1 | 10/2007 | Hegeman et al. |
| 2007/0276430 A1 | 11/2007 | Lee et al. |
| 2009/0202387 A1 | 8/2009 | Dlugos, Jr. et al. |
| 2009/0312773 A1 | 12/2009 | Cabrera et al. |
| 2011/0295242 A1 | 12/2011 | Spivey et al. |
| 2012/0074200 A1 | 3/2012 | Schmid et al. |
| 2012/0078243 A1 | 3/2012 | Worrell et al. |
| 2012/0078247 A1 | 3/2012 | Worrell et al. |
| 2013/0023868 A1 | 1/2013 | Worrell et al. |
| 2013/0123783 A1 | 5/2013 | Marczyk et al. |
| 2016/0270809 A1 | 9/2016 | Boudreaux et al. |

OTHER PUBLICATIONS

PolyMed™ Technical Datasheet. [Dated no later than Mar. 2, 2015].
U.S. Appl. No. 14/659,037, filed Mar. 16, 2015.
U.S. Appl. No. 14/658,944, filed Mar. 16, 2015, Chad P. Boudreaux et al.

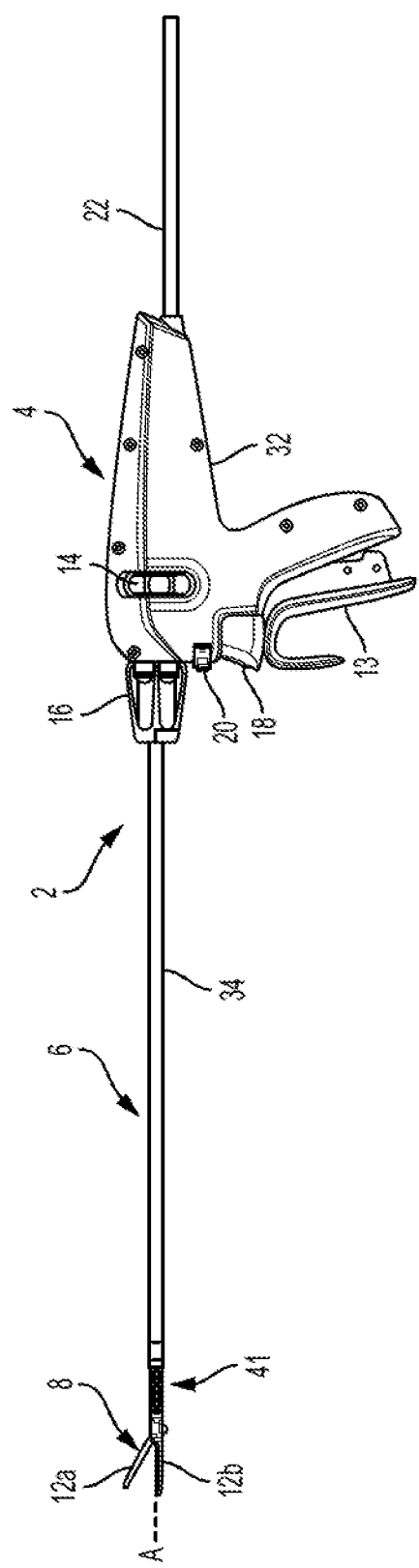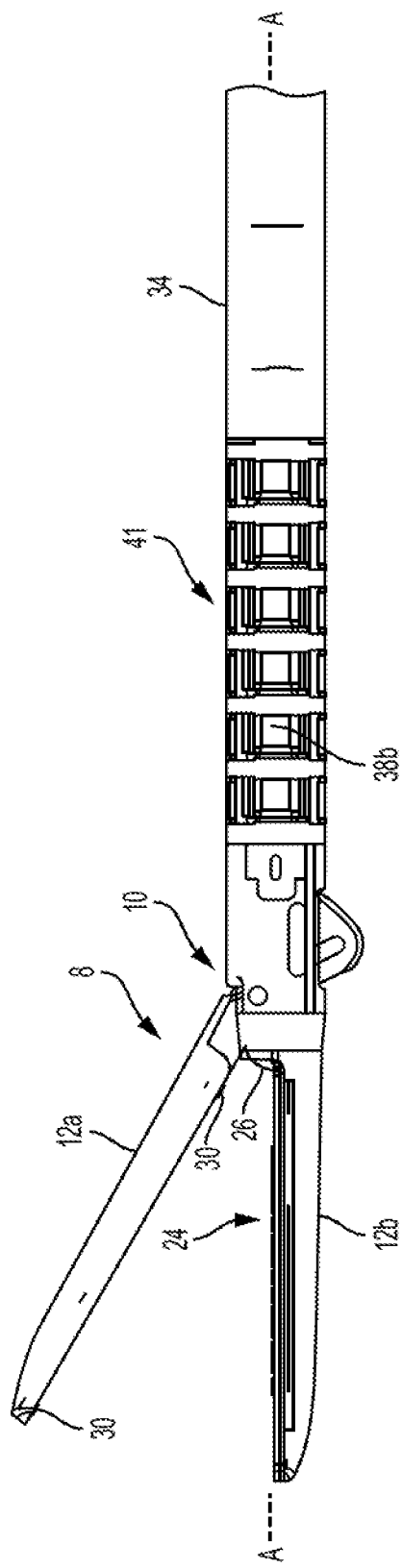

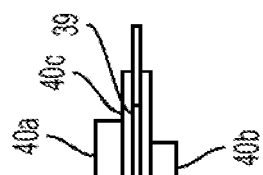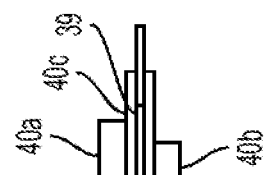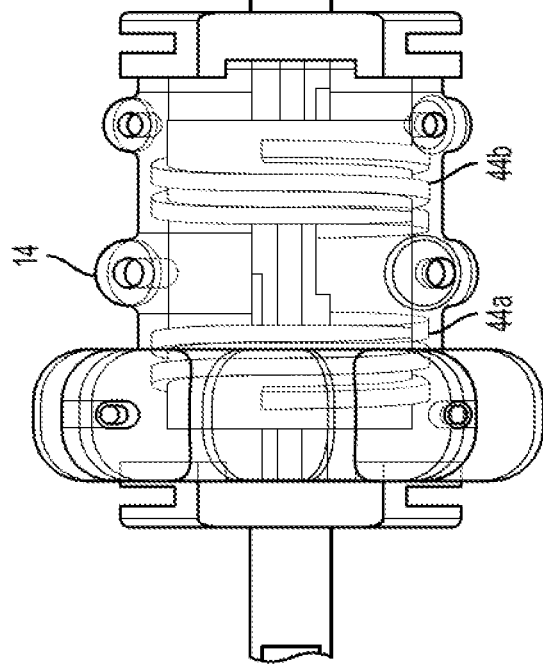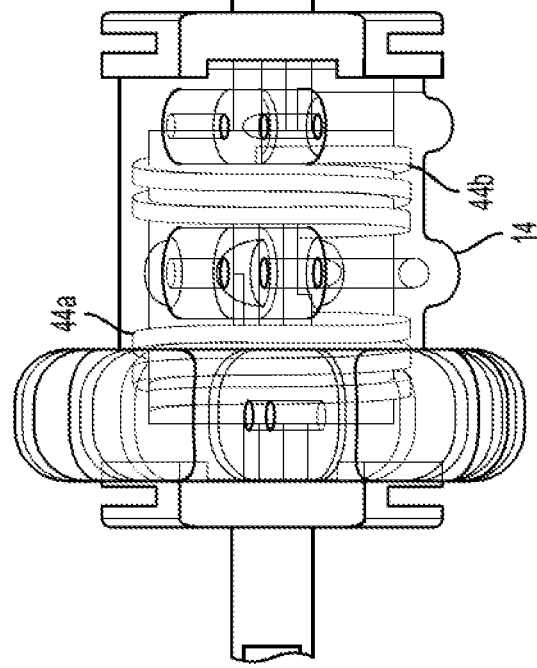
FIG. 19
FIG. 20

METHODS FOR ASSEMBLING SURGICAL INSTRUMENTS

CROSS-REFERENCE TO RELATED APPLICATIONS

The present application claims priority to U.S. patent application Ser. No. 14/658,944 entitled "Methods And Devices For Actuating Surgical Instruments" filed Mar. 16, 2015, which is hereby incorporated by reference in its entirety.

FIELD OF THE INVENTION

The present disclosure relates generally to methods and devices for actuating surgical instruments.

BACKGROUND

Minimally invasive surgical techniques such as endoscopies and laparoscopies are often preferred over traditional surgeries because the recovery time, pain, and surgery-related complications are typically less with minimally invasive surgical techniques. Rather than cut open large portions of the body in order to access inner cavities, surgeons either rely on natural orifices of the body or create one or more small orifices in which surgical instruments can be inserted to allow surgeons to visualize and operate at the surgical site.

Some minimally invasive procedures can require that a working end of a device, which is inserted into the body, be articulated to angularly reorient the working end relative to the tissue. During such a procedure, for example, it is often necessary to reorient the working end such that jaws at the working end are at an angle relative to a shaft of the device, while still allowing the jaws to open and close to grasp tissue. Such angulation is often achieved via one or more cables attached to the jaws. However, with current cable driven jaw reorienting actuation systems, after articulation of the device, the cables are subject to high tensions which makes opening and closing of the jaws with precision difficult.

Accordingly, there remains a need for improved methods and devices for actuating surgical instruments.

SUMMARY

In one embodiment, a surgical device is provided that in one embodiment includes a handle, a shaft assembly, and an end effector. The handle can have an actuation mechanism coupled thereto. The shaft assembly can extend distally from the handle, can include an outer elongate shell defining an inner lumen, and can include first and second elongate members extending longitudinally within the inner lumen. The end effector can be coupled to a distal end of the shaft assembly. The actuation mechanism can be configured to be actuated by a user so as to simultaneously cause a first force to be applied to one of the first and second elongate members, and thereby cause the one of the first and second elongate members to slidably translate proximally and longitudinally within the inner lumen, and cause a second force to be applied to the other of the first and second elongate members, and thereby cause the other of the first and second elongate members to slidably translate distally and longitudinally within the inner lumen. The translation of the first and second elongate members can cause articulation of the end effector.

The surgical device can vary in any number of ways. For example, the shaft assembly can include first and second elongate tubes. The first elongate member can be positioned within the first elongate tube in a fixed position relative thereto. The second elongate member can be positioned within the second elongate tube in a fixed position relative thereto. The actuation mechanism can be configured to move the first and second elongate tubes in response to the actuation of the actuation mechanism, thereby causing the translation of the first and second elongate members. The first elongate member can be attached to the first elongate tube via one of welding and crimping, and the second elongate member can be attached to the second elongate tube via one of welding and crimping. Additionally or alternatively, the first and second elongate tubes in a default state of the surgical device can be tensioned in a distal direction and the first and second elongate members in the default state can be tensioned in a proximal direction, and/or the surgical device can include first and second stabilizing members. The first stabilizing member can be attached to the first elongate tube, the second stabilizing member can be attached to the second elongate tube, and the actuation of the actuation mechanism can be configured to simultaneously longitudinally translate the first stabilizing member, thereby causing the longitudinal translation of the first elongate member, and longitudinally translate the second stabilizing member, thereby causing the longitudinal translation of the second elongate member. The surgical device can include a second actuation mechanism configured to be actuated by the user so as to rotate the first and second stabilizing members about a longitudinal axis of the outer elongate shell so as to cause rotation of the end effector about the longitudinal axis.

For another example, the first elongate member can include a first rigid elongate rod, and the second elongate member can include a second rigid elongate rod. The shaft assembly can include a first flexible elongate band having a proximal end attached to a distal end of the first rigid elongate rod, and the second elongate member can include a second flexible elongate band having a proximal end attached to a distal end of the second rigid elongate rod. The first and second flexible elongate bands can be configured to bend during the articulation of the end effector.

For still another example, the surgical device can include first and second stabilizing members. The first stabilizing member can be attached to the first elongate member via one of welding, crimping, and interference fit. The second stabilizing member can be attached to the second elongate member via one of welding, crimping, and interference fit. The actuation of the actuation mechanism can be configured to simultaneously longitudinally translate the first stabilizing member, thereby causing the longitudinal translation of the first elongate member, and longitudinally translate the second stabilizing member, thereby causing the longitudinal translation of the second elongate member.

For yet another example, the surgical device can include a bend region at a distal portion of the shaft assembly. The shaft assembly can be configured to bend at the bend region so as to articulate the end effector. The first elongate member can include a first rigid elongate rod, the second elongate member can include a second rigid elongate rod, and the shaft assembly can include first and second flexible elongate bands each spanning the bend region. The first elongate band can have a proximal end attached to a distal end of the first rigid elongate rod. The second elongate member can include a second flexible elongate band having a proximal end attached to a distal end of the second rigid elongate rod. The first and second flexible elongate bands can be configured to bend in the bend region during the articulation of the end effector.

For still another example, the actuation mechanism can include first and second drums. The first drum can be coupled to the first elongate member, the second drum can be coupled to the second elongate member, and the actuation of the actuation mechanism can be configured to simultaneously move the first drum in a first direction and thereby apply the first force and cause the longitudinal translation of the first elongate member, and move the second drum in a second direction and thereby apply the second force and cause the longitudinal translation of the second elongate member. The second direction can be opposite to the first direction. The actuation mechanism can be configured to continuously rotate 360° about the longitudinal axis. During the continuous 360° rotation of the actuation mechanism, the one of the first and second elongate members can be configured to first translate proximally and longitudinally within the inner lumen and the other of the first and second elongate members can be configured to translate distally and longitudinally within the inner lumen, and then the one of the first and second elongate members can be configured to translate distally and longitudinally within the inner lumen and the other of the first and second elongate members can be configured to translate proximally and longitudinally within the inner lumen.

For another example, the first and second elongate members in a resting state can be tensioned at a non-zero load.

For yet another example, the actuation mechanism includes one of a rotatable knob, a slidable lever, and a movable handle.

In another aspect, a method of assembling the surgical device is provided that in one embodiment includes advancing the first elongate member into a first passageway of a first tube of the shaft assembly, coupling the first elongate member to the end effector, and with the first elongate member coupled to the end effector and within the first passageway, tensioning the first elongate member in a distal direction and tensioning the first tube in a proximal direction so that the first tube pushes proximally against the actuation mechanism and so that the first elongate member and the first tube are simultaneously tensioned. The method can include attaching the tensioned first elongate member to the tensioned first tube so that the tensioned first elongate member and the tensioned first tube are in a fixed position relative to one another. The method can include advancing the second elongate member into a second passageway of a second tube of the shaft assembly, coupling the second elongate member to the end effector, and with the second elongate member coupled to the end effector and within the second passageway, simultaneously tensioning the second elongate member in the distal direction and tensioning the second tube in the proximal direction so that the second tube pushes proximally against the actuation mechanism and so that the second elongate member and the second tube are simultaneously tensioned. The method can include attaching the tensioned second elongate member to the tensioned second tube so that the tensioned second elongate member and the tensioned second tube are in a fixed position relative to one another.

The method can have any number of variations. For example, the first and second elongate members and the first and second tubes can be tensioned from distal ends thereof. For another example, the method can include, prior to the simultaneous tensioning of the first elongate member and the first tube, attaching a proximal end of a first flexible elongate band to a distal end of the first elongate member. The method can include, prior to the simultaneous tensioning of the second elongate member and the second tube, attaching a proximal end of a second flexible elongate band to a distal end of the second elongate member. The method can include attaching a distal end of the first flexible elongate band to the end effector, and attaching a distal end of the second flexible elongate band to the end effector.

In another embodiment, a surgical device is provided that includes an actuation mechanism, a shaft assembly, and an end effector. The shaft assembly can extend distally from the handle, can include an outer elongate shell defining an inner lumen, can include a first rigid elongate member extending longitudinally within the inner lumen, and can include a first flexible elongate member extending longitudinally within the inner lumen. The first flexible elongate member can have a proximal end thereof attached to a distal end of the first rigid elongate member. The end effector can be attached to a distal end of the first flexible elongate member. The actuation mechanism can be configured to be actuated by a user so as to cause the first rigid elongate member and the first flexible elongate member to slidably translate longitudinally within the inner lumen. The translation of the first rigid elongate member and the first flexible elongate member can cause actuation of the end effector. The actuation of the end effector can include one of moving the end effector between open and closed positions, articulating the end effector, and translating a cutting element along the end effector.

The surgical device can have any number of variations. For example, the surgical device can include a handle. The handle can have the actuation mechanism coupled thereto. The shaft assembly can extend distally from the handle.

In another aspect, a method of assembling a surgical device is provided that in one embodiment includes slidably adjusting a position of a first elongate member within a first inner lumen extending through a first tubular member, slidably adjusting a position of a second elongate member within a second inner lumen extending through a second tubular member, coupling an end effector to the first and second elongate members, and coupling an actuation mechanism to the first and second tubular members. The end effector can be configured to manipulate tissue. The method can include, after adjusting the position of the first elongate member, coupling the first elongate member to the end effector, and coupling an actuation mechanism to the first and second tubular members, moving the first elongate member in a proximal direction and moving the first tubular member in a distal direction so as to achieve a first tension load. The method can include, at the achieved first tension load, securing the first elongate member and the first tubular member in a fixed position relative to one another. The method can include, after adjusting the position of the second elongate member, coupling the second elongate member to the end effector, and coupling an actuation mechanism to the first and second tubular members moving the second elongate member in the proximal direction and moving the second tubular member in the distal direction so as to achieve a second tension load. The method can include, at the achieved second tension load, securing the second elongate member and the second tubular member in a fixed position relative to one another. The actuation mechanism coupled to the first and second tubular members can be configured to be selectively actuated so as to cause the first elongate member and the first tube to move as a unit in one of the proximal and distal directions and to cause the second elongate member and the second tube to move as a unit in the other of the proximal and distal directions, thereby causing articulation of the end effector.

The method can vary in any number of ways. For example, securing the first elongate member and the first tubular member in the fixed position relative to one another can include one of crimping the first elongate member and the first tubular member together and welding the first elongate member and the first tubular member together. For another example, the method can include securing a distal end of a first rigid rod to a proximal end of a first flexible band to form the first elongate member, securing a distal end of the first flexible band to the end effector, securing a distal end of a second rigid rod to a proximal end of a second flexible band to form the second elongate member, and securing a distal end of the second flexible band to the end effector. The first band can be configured to move with the first elongate member and the first tube as a unit in the one of the proximal and distal directions, and the second band can be configured to move with the second elongate member and the second tube as a unit in the other of the proximal and distal directions.

BRIEF DESCRIPTION OF DRAWINGS

This invention will be more fully understood from the following detailed description taken in conjunction with the accompanying drawings, in which:

FIG. 1 is a side view of one embodiment of a surgical device;

FIG. 2 is a side view of a distal portion of the surgical device of FIG. 1;

FIG. 19 is a side view of the actuation mechanism and actuation shafts of FIG. 11 moved from the first position to a second position;

FIG. 20 is a side view of the actuation mechanism and actuation shafts of FIG. 19 moved from the second position to a third position;

DETAILED DESCRIPTION

Figure 3:
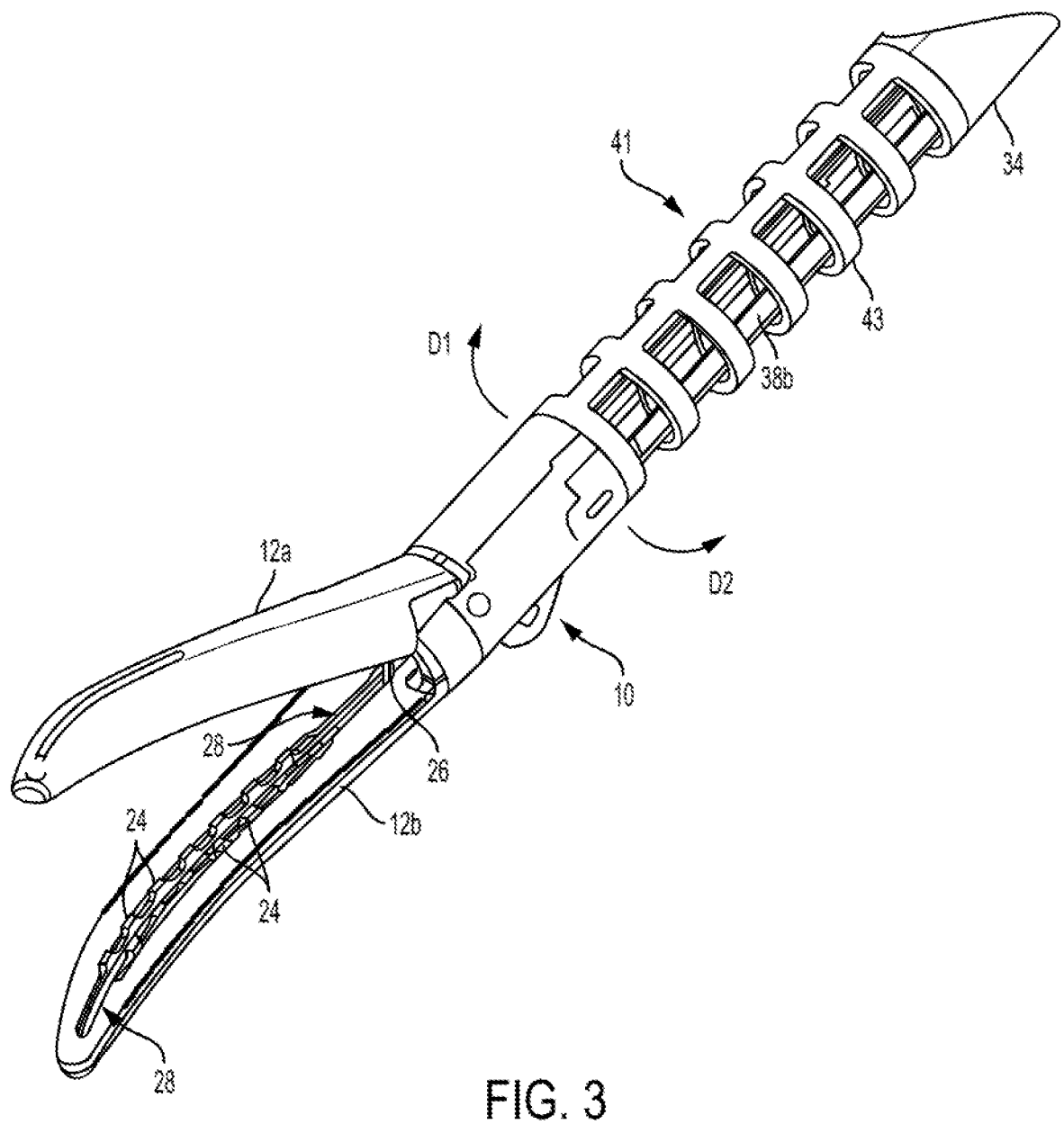
FIG. 3 is a perspective view of a distal portion of the surgical device of FIG. 1.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods and devices for actuating surgical instruments are provided. In general, a surgical device can include one or more actuation shafts configured to facilitate actuation of the device, e.g., articulation of an end effector of the device, opening and closing of jaws at a distal end of the device, moving a cutting element of the device, etc. In an exemplary embodiment, the device can include four actuation shafts, two actuation shafts to facilitate articulation of the device, one actuation shaft to facilitate opening and closing of jaws at a distal end of the device, and one actuation shaft to facilitate moving a cutting element of the device. In an exemplary embodiment, each of the one or more actuation shafts can include a distal elongate member and a proximal elongate member having a distal end attached to a proximal end of the distal elongate member. The proximal elongate member can be rigid, which can help ease insertion of the device into a patient's body directly or through an access device such as a trocar, can facilitate smooth, stable longitudinal translation of the actuation shaft to actuate the device, and/or can facilitate making actuation shafts in a variety of longitudinal lengths since the proximal elongate member can simply be cut to have a desired longitudinal length. The distal elongate member can be flexible, which can accommodate articulation of the device's end effector since the distal elongate member can bend during articulation. In at least some embodiments, each of the one or more actuation shafts can include a tubular member configured to seat the proximal elongate member therein. The tubular member can facilitate attachment of the actuation shaft to an actuator configured to be manually manipulated by a user to cause the desired actuation, e.g., articulation, jaw opening/closing, cutting element movement, etc., and/or can facilitate tensioning of the actuation shaft. Tensioning the actuation shaft can help account for a flexible distal portion of the actuation shaft (e.g., the flexible distal elongate member) by helping to prevent the device from sagging or being loose due to the flexibility of the flexible distal portion of the actuation shaft. The device sagging or being loose can make the device more difficult to advance into a patient because sagging and looseness adversely affects stability, can make the device more difficult to desirably position relative to a surgical target because sagging and looseness adversely affects stability, can inhibit the use of the device in surgical tasks such as otomy creation and tissue manipulation and grasping, and/or can make the device more difficult to actuate since increased force applied by a user can be necessary to overcome the sagging or looseness of the device.

Various exemplary methods of manufacturing the surgical instruments described herein are provided. In general, a surgical device including at least one actuation shaft having a rigid proximal portion and a flexible distal portion (e.g., including a rigid proximal elongate member attached to a flexible distal elongate member) can be manufactured to reduce looseness or tolerance. The reduction can, in an exemplary embodiment, reduce the looseness or tolerance to substantially zero. A person skilled in the art will appreciate that looseness or tolerance may not be precisely zero but nevertheless be considered to be substantially zero due to, e.g., tolerances in measurement devices. The surgical device can thus be manufactured to neutralize tolerance arising from presence of the flexible distal portion. In an exemplary embodiment, the tolerance can be neutralized by simultaneously applying a distally-directed force to a tubular member of the actuation shaft so as to push the tubular member distally and applying a proximally-directed force to a rigid proximal elongate member of the actuation shaft, and accordingly to a flexible distal elongate member of the actuation shaft attached thereto, so as to pull the flexible distal elongate member and the rigid proximal elongate member proximally, thereby reducing sagging and looseness. The tensioned tube and the tensioned rigid proximal elongate member can then be attached together to maintain the load and achieve the reduced sagging and looseness in the assembled device. The proximally-directed force can be applied to the rigid proximal elongate member (and flexible distal elongate member attached thereto) after a distal end of the flexible distal elongate member has been attached to an end effector of the surgical device, which can facilitate the tensioning by holding the distal end of the flexible distal elongate member in a substantially fixed position during the tensioning. The distally-directed force can be applied to the tubular member after assembly of an actuator of the surgical device associated with the actuation shaft being tensioned, which can facilitate the tensioning by allowing a distal end of the tubular member to push against the actuator during the tensioning.

FIG. 1 illustrates one embodiment of a surgical device 2 that can include a proximal handle portion 4 having a shaft assembly 6 extending distally therefrom. As also shown in FIGS. 2 and 3, the device 2 can include a working element 8, also referred to herein as an "end effector," coupled to a distal end of the shaft assembly 6. The end effector 8 can be coupled to the shaft assembly 6 at a pivot joint 10. A proximal end of the end effector 8 can be pivotally coupled to the joint 10 at the distal end of the shaft assembly 6.

The end effector 8 can have a variety of sizes, shapes, and configurations. As shown in FIGS. 1-3, the end effector 8, including the first and second jaws 12a, 12b, can be disposed at a distal end of the surgical device 2. The end effector 8 in this illustrated embodiment includes a tissue grasper having a pair of opposed jaws 12a, 12b configured to move between open and closed positions. The end effector 8 can have other configurations, e.g., scissors, a babcock, a retractor, etc. In an exemplary embodiment, the end effector 8 can be rigid. The end effector 8 can include the first, top, or upper jaw 12a and the second, bottom, or lower jaw 12b pivotally connected together at the pivot joint 10.

One or both of the first jaw 12a and the second jaw 12b can include spacers 30 on facing tissue engagement surfaces thereof. The spacers 30 can be configured to maintain a minimum gap of space between the jaws 12a, 12b, e.g., between the tissue engagement surfaces thereof, when the jaws 12a, 12b are in the closed position. The gap of space can help prevent electrodes 24, discussed further below, from becoming damaged and/or from creating a closed circuit loop between the jaws 12a, 12b, as opposed to a closed circuit loop with tissue engaged between the jaws 12a, 12b. In this illustrated embodiment, only the top jaw includes spacers 30 extending therefrom toward the bottom jaw 12b, as shown in FIG. 3. In other embodiments, only the bottom jaw may include spacers, or both the top and bottom jaws may include spacers.

One or both of the jaws 12a, 12b can include the electrodes 24, which can be configured to contact tissue positioned between the jaws 12a, 12b and to apply energy thereto. The electrodes 24 are arranged longitudinally along the bottom jaw 12b in this illustrated embodiment, but the electrodes 24 can be arranged in any of a variety of ways on the upper jaw 12a and/or the lower jaw 12b.

The handle portion 4 can have a variety of sizes, shapes, and configurations. The handle portion 4 can include a main housing 32, which can house a variety of elements therein and can have some elements accessible outside thereof, such as a first actuator 13, a second actuator 14, a third actuator 16, a fourth actuator 18, and a fifth actuator 20.

The first actuator 13 can be configured to effect the opening and closing of the opposed jaws 12a, 12b, e.g., movement of the jaws 12a, 12b toward and away from one another. The jaws 12a, 12b in FIGS. 1-3 and 6 are shown in the open position. As in this illustrated embodiment, the upper jaw 12a can be configured to move relative to the bottom jaw 12b, which can remain stationary relative to the shaft assembly 6, to effect the opening and closing of the end effector 8. In other embodiments, in order to effect opening and closing of the end effector, the bottom jaw can be configured to move relative to the upper jaw, or both the upper and lower jaws can be configured to move relative to the shaft assembly.

Figure 4:
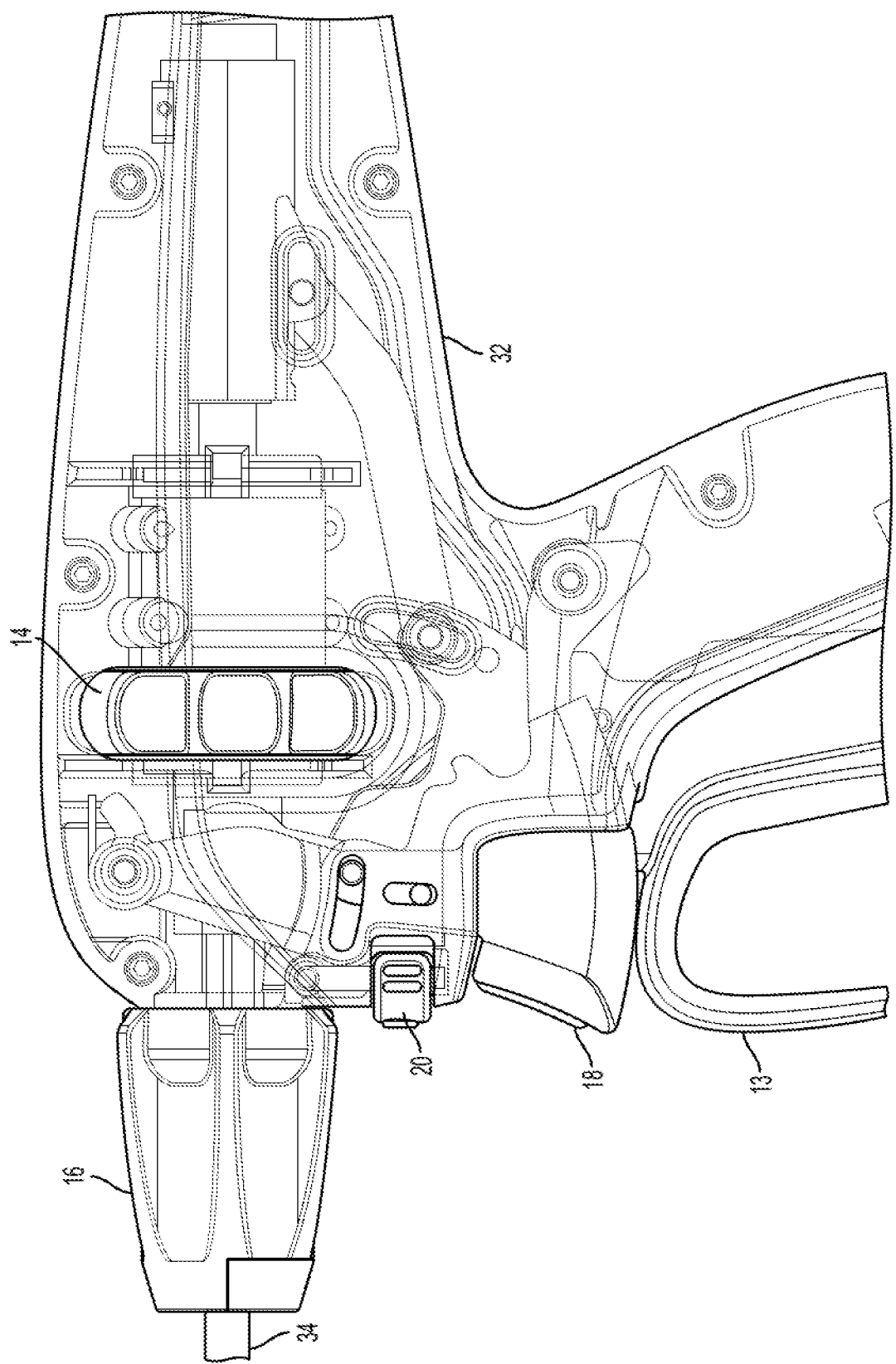
FIG. 4 is a side, partially transparent view of a proximal portion of the surgical device of FIG. 1.
Figure 5:
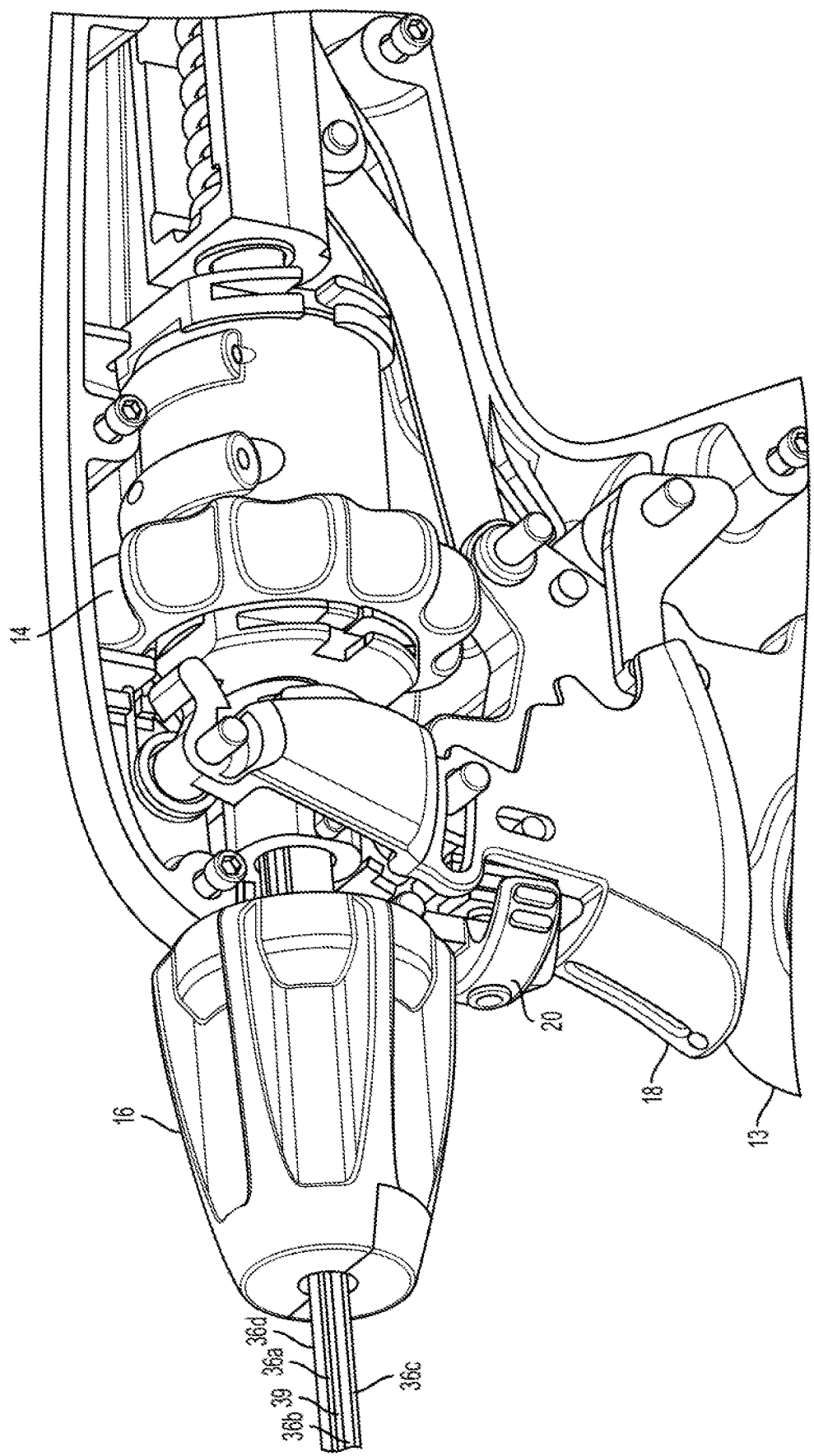
FIG. 5 is a perspective view of a proximal portion of the surgical device of FIG. 1 with select elements of the device omitted for clarity of illustration.

In an exemplary embodiment, the first actuator 13 can include a gripper arm, also referred to herein as a "handle" and a "movable handle." The handle 13 can, in other embodiments, have different sizes, shapes, and configurations, e.g., no thumb rests, multiple finger loops, different arcuate shape, etc. As shown in FIGS. 1, 4, and 5, the handle 13 can be pivotally attached to the main housing 32. The handle 13 can be configured to move toward and away from the main housing 32, thereby causing opening and closing of the end effector 8, as discussed further below.

The second actuator 14 can be configured to effect articulation of the end effector 8, e.g., movement of both jaws 12a, 12b in a same direction relative to a longitudinal axis A of the shaft assembly 6. The articulation can be independent of the opening and closing of the jaws 12a, 12b. The end effector 8 in FIGS. 1-3 is shown in an unarticulated position, e.g., at a zero angle relative to the longitudinal axis A. The second actuator 14 can be operatively connected to an actuation mechanism, which can be disposed within the main housing 32 and is discussed further below, such that actuation of the second actuator 14, e.g., manual movement thereof by a user, can cause articulation of the end effector 8. In an exemplary embodiment, the second actuator 14 can be configured to be actuated so as to cause the jaws 12a, 12b to articulate in opposite directions D1, D2 (shown in FIG. 3) relative to the longitudinal axis A.

The second actuator 14 can have a variety of sizes, shapes, and configurations. As in this illustrated embodiment, the second actuator 14 can include a rotatable knob. Rotation of the second actuator 14 in one direction (e.g., clockwise) can be configured to cause articulation of the end effector 8 in the first direction D1 (e.g., right) and rotation of the second actuator 14 in the opposite direction (e.g., counterclockwise) can be configured to cause articulation of the end effector 8 in the second direction D2 (e.g., left). The knob 14 can be rigid. The knob 16 can include a moveable ring, as shown in FIG. 5. The knob 14 can include one or more finger depressions on an exterior surface thereof, as in this illustrated embodiment. The finger depressions can facilitate manual movement of the knob 14 using one or more fingers seated in the finger depressions. As in this illustrated embodiment, the finger depressions can extend around an entire circumference of the knob's exterior surface.

The third actuator 16 can be configured to rotate the shaft assembly 6 and the end effector 8 about the longitudinal axis A of the shaft assembly 6. The third actuator 16 includes a rotatable knob in this illustrated embodiment that can be rotated about the longitudinal axis A, but the third actuator 16 can have a variety of other configurations, e.g., a lever, a button, a movable handle, etc. As in this illustrated embodiment, the third actuator 16 can be configured to continuously and repeatedly rotate the shaft assembly 6 and the end effector 8 360° in both clockwise and counterclockwise directions. In other words, the shaft assembly 6 can be configured for unlimited bi-directional rotation. As will be appreciated by a person skilled in the art, the shaft assembly 6 and the end effector 8 can be rotated less than 360° as desired during performance of a surgical procedure (e.g., rotated 20°, rotated 90°, rotated 150°, etc.) and can be rotated more than 360° as desired during performance of a surgical procedure (e.g., rotated 450°, rotated 480°, rotated 720°, etc.).

Figure 6:
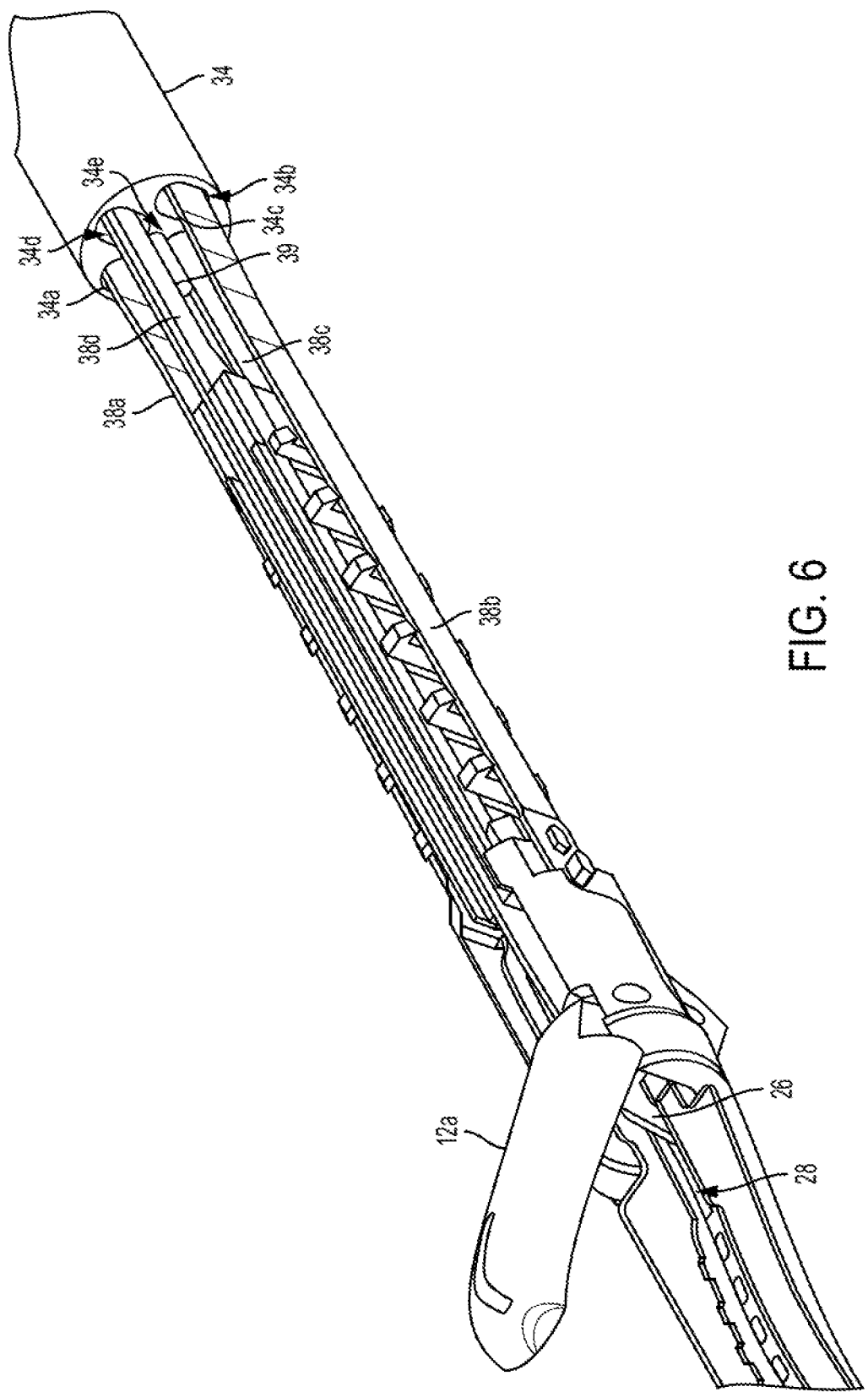
FIG. 6 is a perspective view of a distal portion of the surgical device of FIG. 1 with a flexible outer shell of the device omitted for clarity of illustration.
Figure 7:
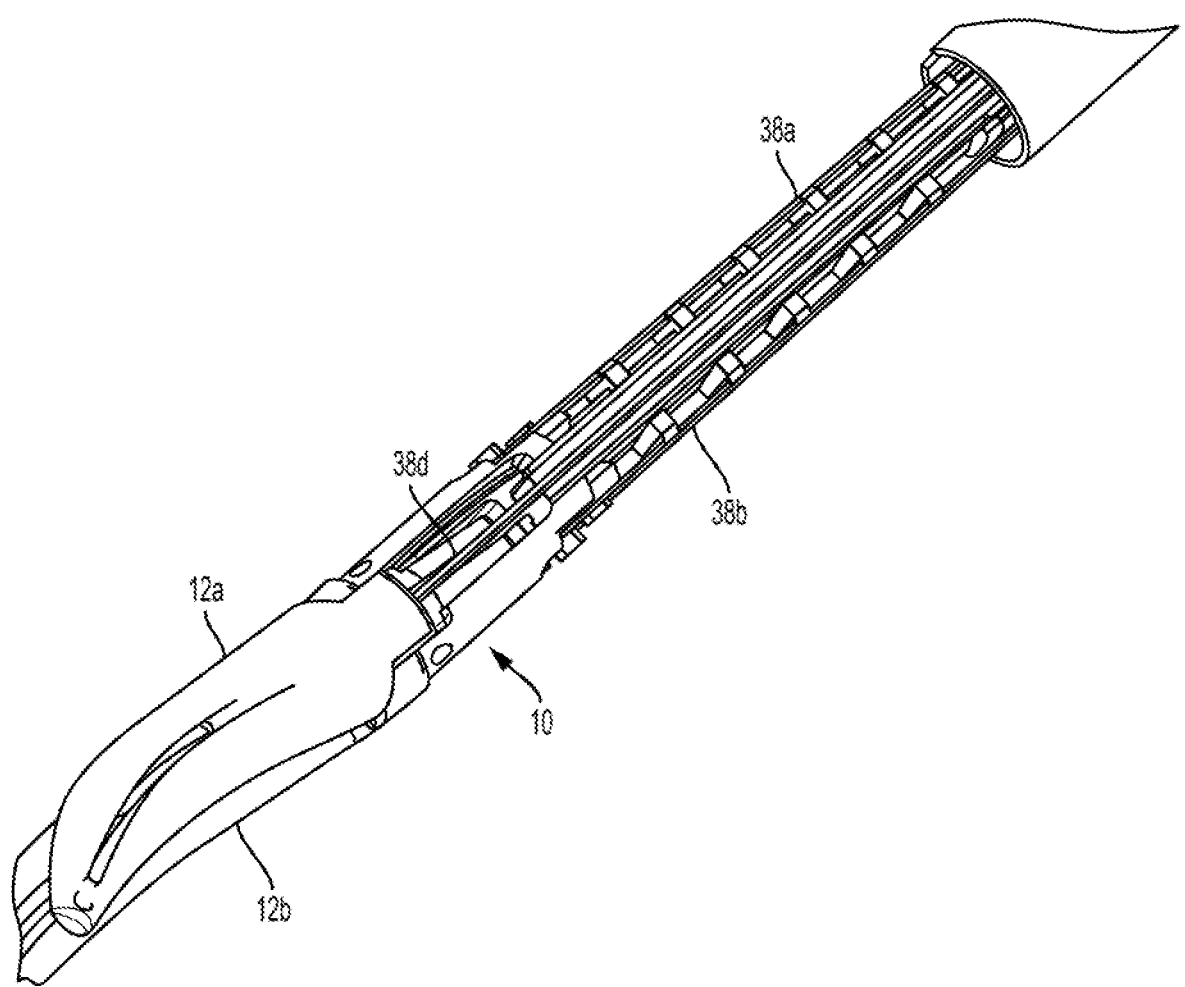
FIG. 7 is a another perspective view of the distal portion of the surgical device of FIG. 6.

The fourth actuator 18 can be configured to translate a cutting element 26 (e.g., a knife, a blade, etc.) along the end effector 8. The cutting element 26 can be configured to cut tissue positioned between the jaws 12a, 12b, as will be appreciated by a person skilled in the art. As shown in FIGS. 3 and 6, the jaws 12a, 12b can include an elongate slot 28 therein (the slot in the upper jaw 12a is obscured in FIGS. 3 and 6) through which the cutting element 2 can be configured to slide.

As in this illustrated embodiment, the surgical device 2 can be powered and be configured as an electrosurgical tool configured to apply energy to tissue, such as radiofrequency (RF) energy. The handle portion 4 can have a power cord 22 extending proximally therefrom that can be configured to supply electrical power to the device 2, such as by connecting to a generator, by plugging into an electrical outlet, etc. The fifth actuator 20 can be configured to turn on and off the application of the energy, which can be delivered to tissue via the electrodes 24. The fifth actuator 20 includes a button in this illustrated embodiment, but the fifth actuator 20 can have other configurations, e.g., a knob, a lever, a movable handle, a switch, etc. In other embodiments, the surgical device can be unpowered, e.g., not be configured to apply energy to tissue.

The shaft assembly 6 can have a variety of sizes, shapes, and configurations. The shaft assembly 6 can have any longitudinal length, although in an exemplary embodiment it can be long enough to allow the handle portion 4 to be manipulated outside a patient's body while the shaft assembly 6 extends through an opening in the body with the end effector 8 disposed within a body cavity, e.g., have a longitudinal length of about 33 cm. In this way, the end effector 8 can be easily manipulated when the device 2 is in use during a surgical procedure. The shaft assembly 6 can have any diameter. For example, the shaft assembly's diameter can be less than or equal to about 15 mm, e.g., less than or equal to about 10 mm, less than or equal to about 7 mm, less than or equal to about 5 mm, etc., which can allow for insertion of the shaft assembly 6 through an minimally invasive access device, such as during a laparoscopic surgical procedure. The end effector 8 mated to the shaft assembly's distal end can have a diameter equal to or less than the shaft assembly's diameter, at least when the jaws 12a, 12b are in the closed position, which can facilitate insertion of the device's distal portion into a patient's body.

As in this illustrated embodiment, the shaft assembly 6 can include an outer elongate shaft 34 (also referred to herein an "outer shell") and at least one actuation shaft extending between the handle portion 4 and the end effector 8. The one or more actuation shafts can be configured to facilitate articulation of the end effector 8, to facilitate opening/closing of the end effector 8, and/or to facilitate movement of the cutting element 26 along the end effector 8. As in this illustrated embodiment, the device 2 can include first and second actuation shafts configured to facilitate articulation of the end effector 8, a third actuation shaft configured to facilitate opening/closing of the end effector 8, and a fourth actuation shaft configured to facilitate movement of the cutting element 26 along the end effector 8. In other embodiments, a surgical device can include any combination of the actuation shafts configured to facilitate articulation of the end effector, opening/closing of the end effector, and movement of the cutting element along the end effector, e.g., only include the first and second actuation shafts; only include the fourth actuation shaft; include the first, second, and third actuation shafts; include the third and fourth actuation shafts; etc. The actuation shafts can each have relatively small diameters, which can facilitate their inclusion in a device configured to use in a minimally invasive surgical procedure. In an exemplary embodiment, the actuation shafts can each have a diameter of about 0.04 in. In an exemplary embodiment, the outer shell 34 can have a diameter in a range of about 0.2 in. to 0.221 in. A person skilled in the art will appreciate that an element may not have a diameter of a precisely value but nevertheless be considered to have a diameter of about that value due to, e.g., manufacturing tolerances.

As in this illustrated embodiment, each of the actuation shafts can include a distal elongate member and a proximal elongate member having a distal end attached to a proximal end of the distal elongate member. The distal end of the proximal elongate member can be attached to the proximal end of the distal elongate member in a variety of ways, such as by welding, crimping, gluing, threading, swaging, stamping, trapping, riveting, etc. In an exemplary embodiment, the distal end of the proximal elongate member can be attached to the proximal end of the distal elongate member by welding or crimping, which can be cost effective for manufacturing and/or which can be a relatively simple process during manufacturing. The proximal elongate member can be a rigid member (e.g., generally unable to flex or bend without cracking, breaking, or otherwise becoming damaged), and the distal elongate member can be a flexible member (e.g., generally able to flex or bend without cracking, breaking, or otherwise becoming damaged). The actuation shaft can be made from one or more materials such as titanium, stainless steel, a stranded cable, etc. The rigid and flexible members of the actuation shaft can be made from the same material or can be made from different materials. In an exemplary embodiment, the actuation shaft can have a yield strength in a range of about 40 to 200 ksi. The rigid nature of the proximal elongate member can facilitate stability of the device 2, which can help ease insertion of the device 2 into a patient's body directly or through an access device such as a trocar. This property of the proximal elongate member can facilitate smooth, stable longitudinal translation of the actuation shaft relative to the outer shaft 34, discussed further below. The rigid nature of the proximal elongate member can facilitate making actuation shafts in a variety of longitudinal lengths for different surgical devices since the proximal elongate member can be cut to a desired longitudinal length, as discussed further below. The flexible nature of the distal elongate member can accommodate articulation of the end effector 8 since the distal elongate member can be configured to bend so as to facilitate articulation of the end effector 8 coupled thereto. As discussed further below, the actuation shaft having a rigid portion and a flexible portion can ease manufacturing of the device 2 since an entirely flexible actuation shaft need not be formed, such as by stamping, which is traditionally more expensive than methods to form a rigid member, such as molding or casting. The actuation shaft having a rigid portion and a flexible portion can ease manufacturing of surgical devices since distal elongate members can all be formed with a same longitudinal length and proximal elongate members can be formed at selected, different longitudinal lengths, thereby allowing formation of actuation shafts having different longitudinal lengths appropriate for use in different sized devices and/or reducing costs since it is traditionally more expensive to manufacture a flexible member for actuation of a surgical device than to form a rigid member for actuation of a surgical device.

The proximal and distal elongate members can have a variety of configurations. The proximal elongate member can be rigid, as mentioned above, and can include an elongate rod (as in this illustrated embodiment), an elongate band, etc. The distal elongate member can be flexible, as mentioned above, and can include an elongate rod, an elongate band (as in this illustrated embodiment), a cable, a wire, etc. The distal elongate member being a substantially planar band can help conserve real estate at a distal portion of the device 2. A person skilled in the art will appreciate that a band may not be precisely planar but nevertheless be considered to be substantially planar due to, e.g., manufacturing tolerances.

As mentioned above, the device 2 in this illustrated embodiment includes four actuation shafts, as shown in FIGS. 5-11. The first actuation shaft can be configured to facilitate articulation of the end effector 8 and can include a first proximal elongate member 36*a*, a first distal elongate member 38*a* attached to the first proximal elongate member 36*a*, and a first elongate tube 40*a* (shown in FIG. 11) attached to the first proximal elongate member 36*a* and having an inner lumen in which the first proximal elongate member 36*a* can be disposed. The second actuation shaft can be configured to facilitate articulation of the end effector 8 and can include a second proximal elongate member 36*b*, a second distal elongate member 38*b* attached to the second proximal elongate member 36*b*, and a second elongate tube 40*b* (shown in FIG. 11) attached to the second proximal elongate member 36*b* and having an inner lumen in which the second proximal elongate member 36*b* can be disposed. The first and second elongate tubes 40*a*, 40*b* can help provide rigidity to the first and second actuation shafts, respectively, in proximal regions thereof, which can help take the positioning load of the respective actuation shafts instead of the first and second proximal elongate members 36*a*, 36*b* bearing all the positioning load. The first and second elongate tubes 40*a*, 40*b* are enclosed in tubes in this illustrated embodiment, but the first and second elongate tubes can have one or more breaks or openings therein in other embodiments. Proximal elongate members can be attached to their respective tubes in a variety of ways, such as by welding, crimping, gluing, threading, swaging, stamping, trapping, riveting, etc. In an exemplary embodiment, the attachment can be via welding or crimping, which can be cost effective for manufacturing and/or which can be a relatively simple process during manufacturing. In this illustrated embodiment, the proximal elongate members are welded to their respective tubes.

Figure 14:
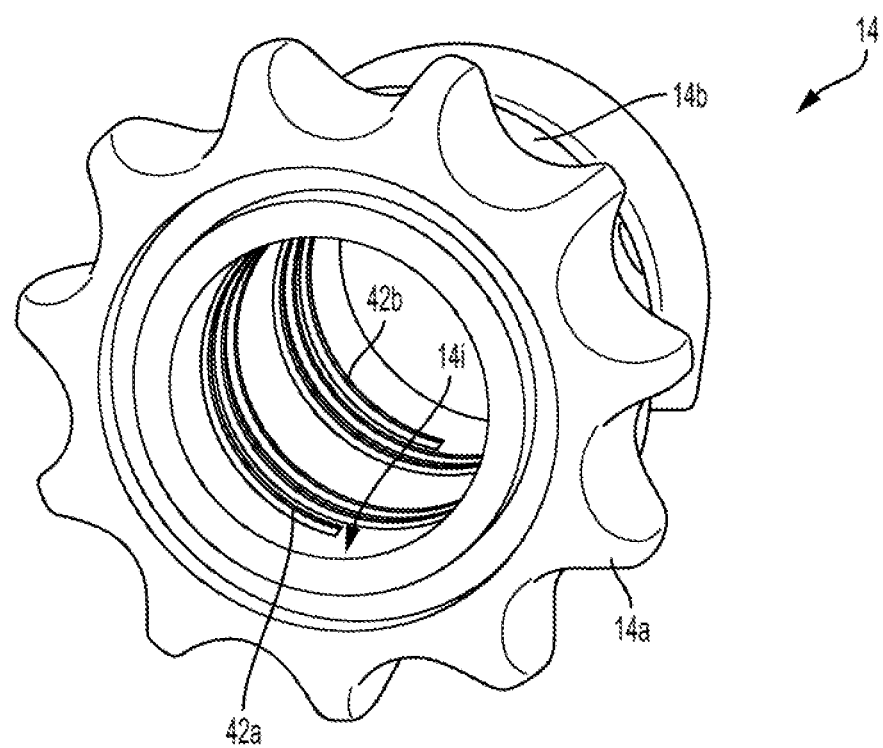
FIG. 14 is a perspective view of an actuator of the surgical device of FIG. 1.
Figure 14A:
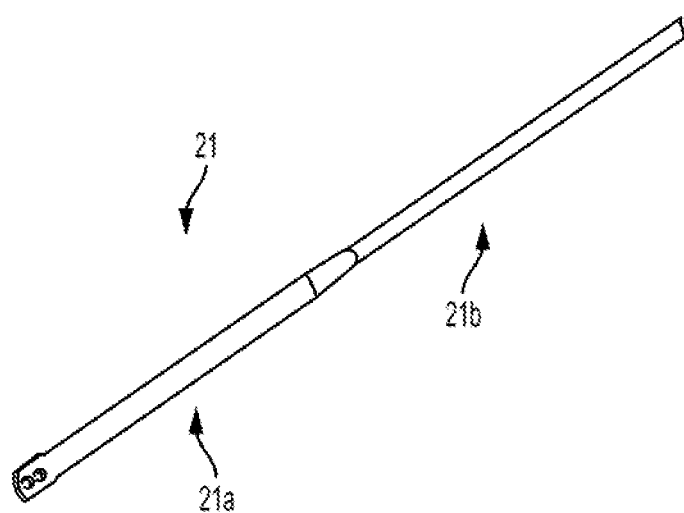
FIG. 14A is a perspective view of a distal portion of one embodiment of an actuation shaft.

FIG. 14A illustrates another exemplary embodiment of an actuation shaft 21. The actuation shaft 21 can be used as an actuation shaft in the surgical devices described herein. In this illustrated embodiment, the actuation shaft 21 includes a distal elongate member 21*a* and a proximal elongate member 21*b* that are monolithically formed. The actuation shaft 21 can include a single cylindrical rod defining the distal elongate member 21*a* and the proximal elongate member 21*b*. A distal portion of the cylindrical rod being flattened (e.g., by cold forming) and trimmed to define the distal elongate member 21*a*.

Figure 16:
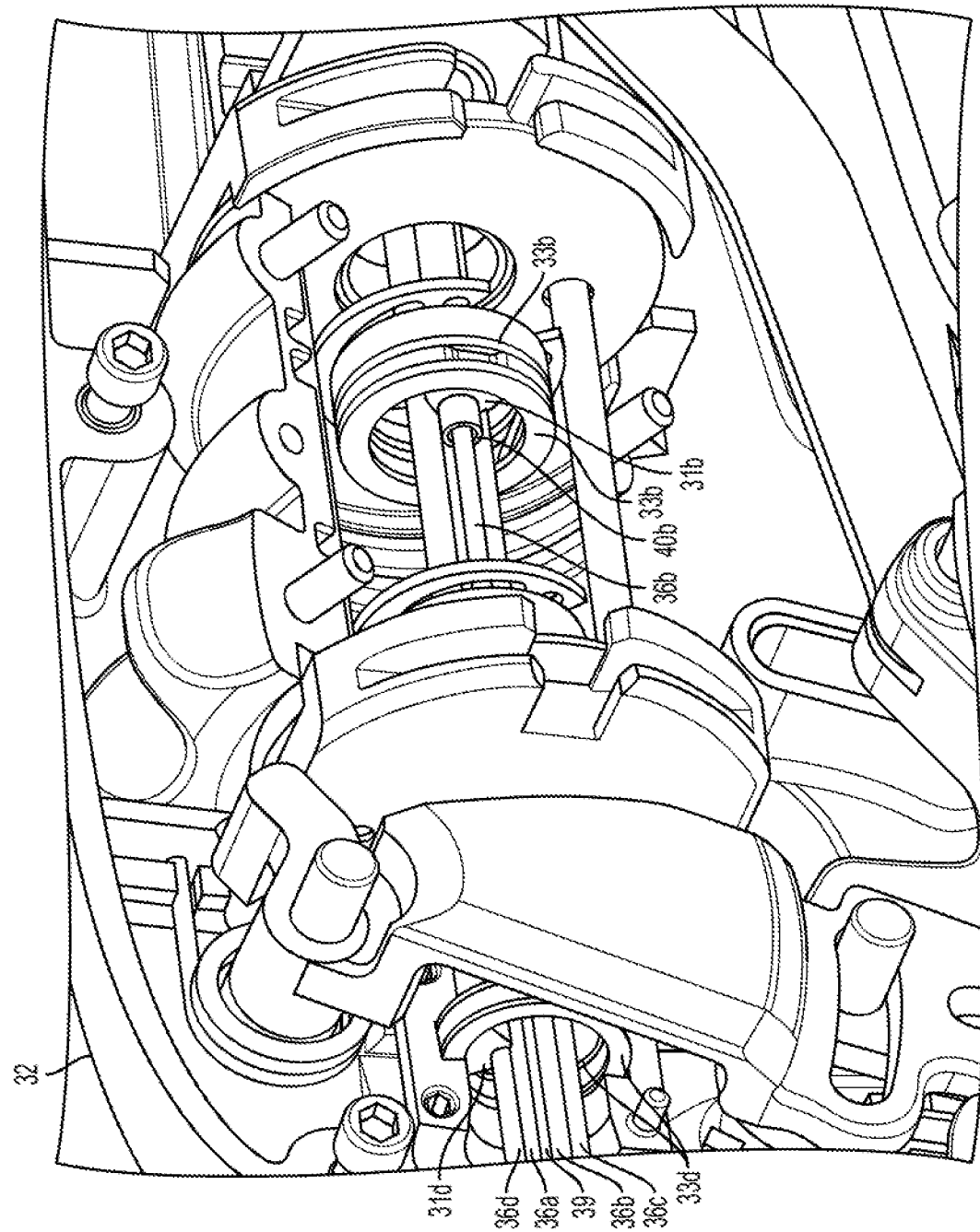
FIG. 16 is a perspective, partial view of the handle portion of the surgical device of FIG. 1 with select elements of the device omitted for clarity of illustration.
Figure 17:
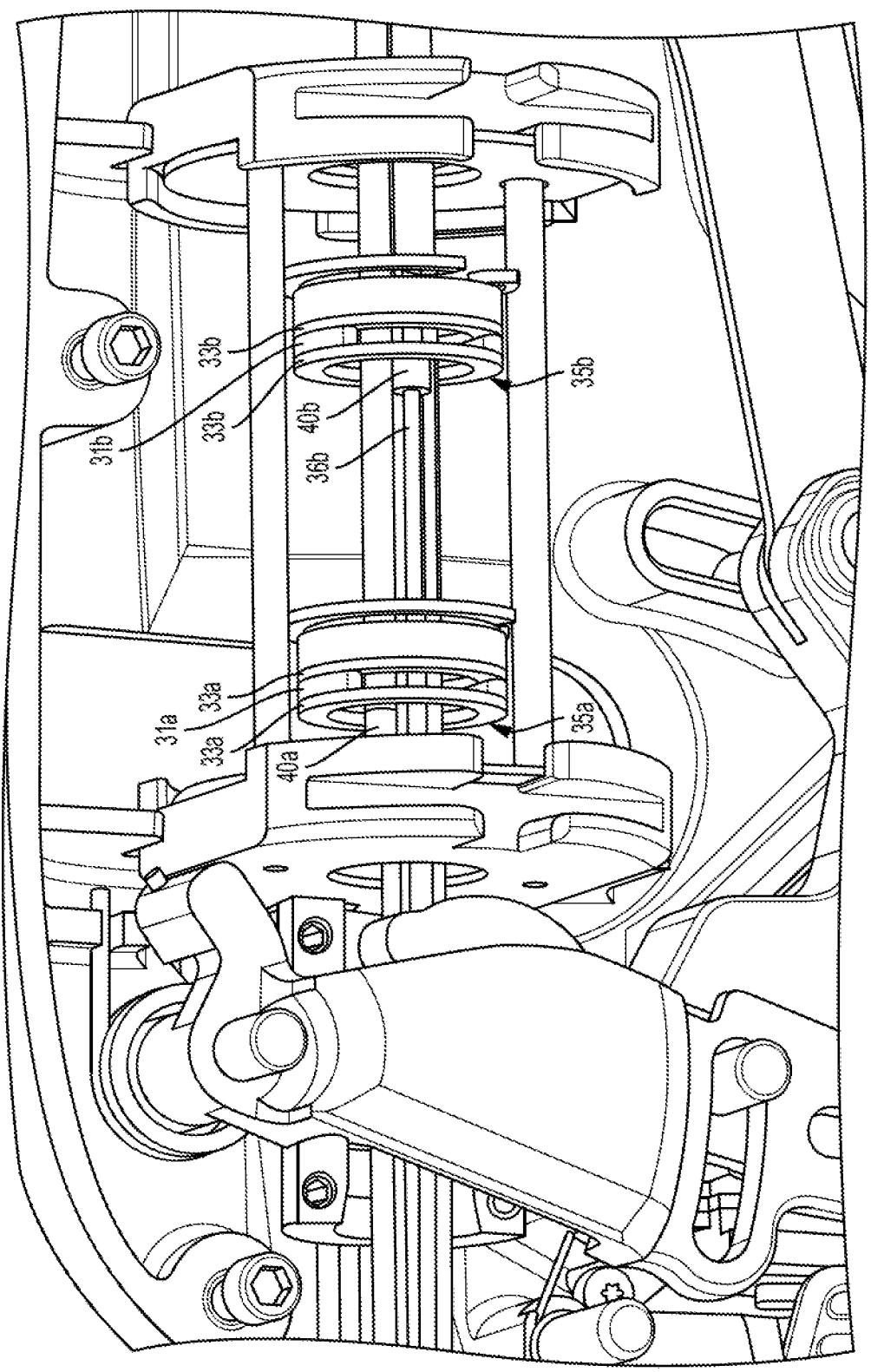
FIG. 17 is another perspective, partial view of the handle portion of the surgical device of FIG. 1 with select elements of the device omitted for clarity of illustration.

Referring again to the embodiment of FIG. 1, the first and second actuation shafts can be operatively connected to the device's second actuator 14 to facilitate articulation of the end effector 8. The first and second actuation shafts can be operatively connected to the device's second actuator 14 in a variety of ways. As in this illustrated embodiment, as shown in FIGS. 16 and 17, the device 2 can include a first stabilizing member 35*a* configured to couple the first actuation shaft to the second actuator 14, and can include a second stabilizing member 35*b* configured to couple the second actuation shaft to the second actuator 14. The first and second stabilizing members 35*a*, 35*b* can have a variety of configurations, but in an exemplary embodiment, they are the same as one another. The first stabilizing member 35*a* can include a first pair of washers 33*a* and a first clip 31*a* coupled thereto. The first pair of washers 33*a* can be ring-shaped, and the first clip 31*a* can be sandwiched therebetween, as in this illustrated embodiment. The first clip 31*a* can be configured to clip to the first tube 40*a* of the first actuation shaft, as shown in FIG. 17. The first tube 40*a* can have a notch (not shown) formed therein configured to receive the first clip 31*a* therein, as in this illustrated embodiment. The structural stability of the first proximal elongate member 36*a* positioned within the first tube 40*a* can thus be maintained since the first tube 40*a* instead of the first proximal elongate member 36*a* can directly connect to the first clip 31*a*. Similar to the first stabilizing member 35*a*, the second stabilizing member 35*b* can include a first pair of washers 33*b* and a second clip 31*b* coupled thereto that can be configured to clip to the second tube 40*b* of the second actuation shaft, as shown in FIGS. 16 and 17. The second tube 40*b* can have a notch (not shown) formed therein configured to receive the second clip 31*b* therein, as in this illustrated embodiment. The structural stability of the second proximal elongate member 36*b* positioned within the second tube 40*b* can thus be maintained since the second tube 40*b* instead of the second proximal elongate member 36*b* can directly connect to the second clip 31*b*. The second pair of washers 33*b* can be ring-shaped, and the second clip 31*b* can be sandwiched therebetween, as in this illustrated embodiment.

The third actuation shaft can be configured to facilitate opening and closing of the jaws 12*a*, 12*b* and can include a third proximal elongate member 36*c*, a third distal elongate member 38*c* attached to the third proximal elongate member 36*c*, and a third elongate tube 40*c* (shown in FIGS. 9-11) having an inner lumen in which the third proximal elongate member 36*c* can be disposed. The third actuation shaft can be operatively connected to the first actuator 13 in a way such that actuation of the first actuator 13, e.g., movement of the handle 13, can cause opening and closing of the end effector 8. Movement of the handle 13 from an open position shown in FIGS. 5 and 9, in which the end effector 8 is open, to a closed position shown in FIG. 10, in which the end effector 8 is closed, can be achieved by moving the handle 13 toward the main housing 32 can cause the third actuation shaft to move proximally, as shown by the proximal movement of the third actuation shaft's third tube 40c from FIG. 9 to FIG. 10. Likewise, movement of the handle 13 from the closed position of FIG. 10 to the open position of FIG. 9 can cause the end effector 8 to open. The third actuation shaft can be operatively connected to the first actuator 13 in a variety of ways, such as by using a stabilizing member (not shown) similar to the stabilizing members described herein.

Figure 18:
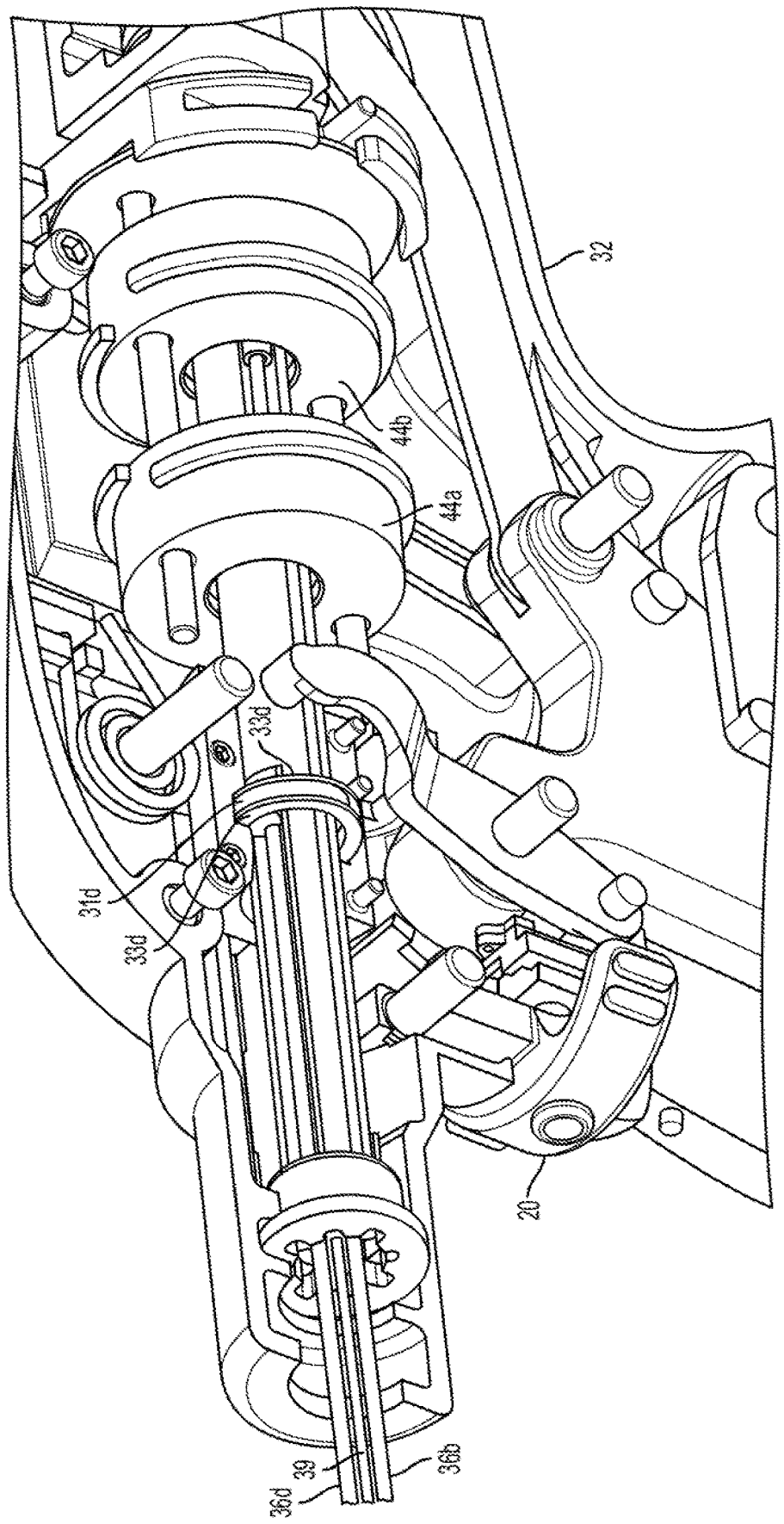
FIG. 18 is a perspective, partial view of a proximal portion of the surgical device of FIG. 1 with select elements of the device omitted for clarity of illustration.

The fourth actuation shaft can be configured to facilitate movement of the cutting element 26 through the end effector 8 and can include a fourth proximal elongate member 36d, a fourth distal elongate member 38d attached to the fourth proximal elongate member 36d, and a fourth elongate tube (obscured in the Figures) having an inner lumen in which the fourth proximal elongate member 36d can be disposed. The fourth actuation shaft can be operatively connected to the fourth actuator 18 such that actuation of the fourth actuator 18 can be configured to cause movement of the fourth actuation shaft and thereby move the cutting element 26 along the end effector 8. The fourth actuation shaft can be operatively connected to the fourth actuator 18 in a variety of ways. As in this illustrated embodiment, as shown in FIGS. 16 and 18, the device 2 can include a third stabilizing member 35d configured to couple the fourth actuation shaft to the fourth actuator 18. The third stabilizing member 35d can be configured similar to the stabilizing members described herein, and can include a third pair of washers 33c and a third clip 31c coupled thereto that can be configured to clip to the fourth tube 40d of the fourth actuation member. The fourth tube 40d can have a notch (not shown) formed therein configured to receive the third clip 31c therein, as in this illustrated embodiment. The structural stability of the fourth proximal elongate member 36d positioned within the fourth tube 40d can thus be maintained since the fourth tube 40d instead of the fourth proximal elongate member 36d can directly connect to the third clip 31c.

The fifth actuator 20 can be operatively connected to a conductive lead 39 (shown in FIGS. 5, 9, and 10 and in FIG. 6 with a distal portion thereof absent to ease illustration of other parts of the device 2), which in this illustrated embodiment includes an RF cable, configured to be in electrical communication with the power cord 22 and with the electrodes 24. The actuation of the fifth actuator 20, e.g., pushing the button, can be configured to close a circuit and thereby allow power to be provided to the RF cable 39, which can accordingly allow power to be supplied to the electrodes 24.

Figure 12:
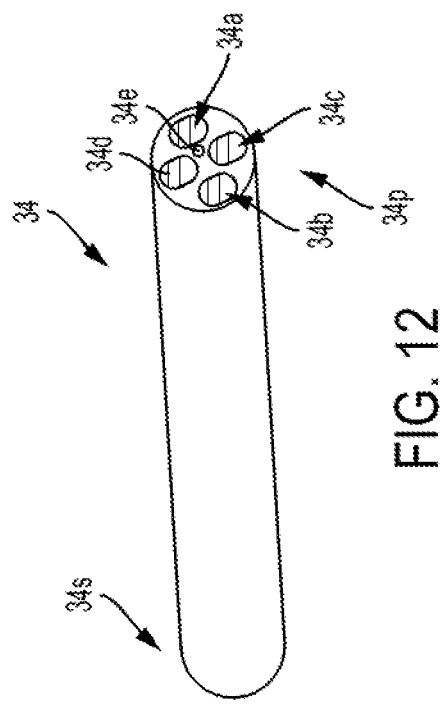
FIG. 12 is a perspective view of an outer elongate shaft of the surgical device of FIG. 1.

The outer elongate shaft 34 of the shaft assembly 6, which is illustrated as a standalone element in FIG. 12, can have a variety of sizes, shapes, and configurations. The outer shell 34 can be configured to stabilize movement of the actuation shafts during actuation of various actuators. The outer shell 34 can include a plurality of inner lumens 34a, 34b, 34c, 34d, 34e extending therethrough, as in this illustrated embodiment. The inner lumens 34a, 34b, 34c, 34d, 34e can be isolated from one another, as in this illustrated embodiment, which can help allow elements disposed in each of the inner lumens 34a, 34b, 34c, 34d, 34e to have different loads without affecting others of the elements and/or can help allow elements disposed in each of the inner lumens 34a, 34b, 34c, 34d, 34e to simultaneously move in different directions. In an exemplary embodiment, a number of the inner lumens 34a, 34b, 34c, 34d, 34e can equal a number of actuator shafts, which in this illustrated embodiment is five, such that each of the actuator shafts can be disposed in its own one of the inner lumens 34a, 34b, 34c, 34d, 34e. In other embodiments, the outer shell 34 can include a number of inner lumens less than a number of actuator shafts. The outer shell 34 can be configured to help protect the actuation shafts from an external environment along a longitudinal length of the outer shell 34. The first, second, third, and fourth actuation shafts can be configured to longitudinally translate within their respective ones of the inner lumens 34a, 34b, 34c, 34d, proximally and distally, in response to actuation of their respective ones of the first, second, third, and fourth actuators 13, 14, 16, 18. In an exemplary embodiment, the first and second actuation shafts configured to facilitate articulation can be slidably seated in ones of the inner lumens 34a, 34b on opposite sides (e.g., left and rights sides) of the outer shell 34, which can facilitate articulation of the end effector 8 in opposite directions (e.g., left and right).

As in this illustrated embodiment, as shown in FIGS. 4-6, the proximal elongate members 36a, 36b, 36c, 36d can be configured to be located in proximal regions of their respective inner lumens 34a, 34b, 34c, 34 and extend out a proximal end 34p of the outer shell 34, and the distal elongate members 38a, 38b, 38c, 38d can be configured to be located in distal regions of their respective inner lumens 34a, 34b, 34c, 34 and extend out a distal end 34s of the outer shell 34. Accordingly, the connection areas between the first elongate members 36a, 38b, the second elongate members 36b, 38b, the third elongate members 36c, 38c, and the fourth elongate members 36d, 38d can be located within the outer shell 34. This can help protect the connection areas from any inadvertent wear or damage.

Figure 8:
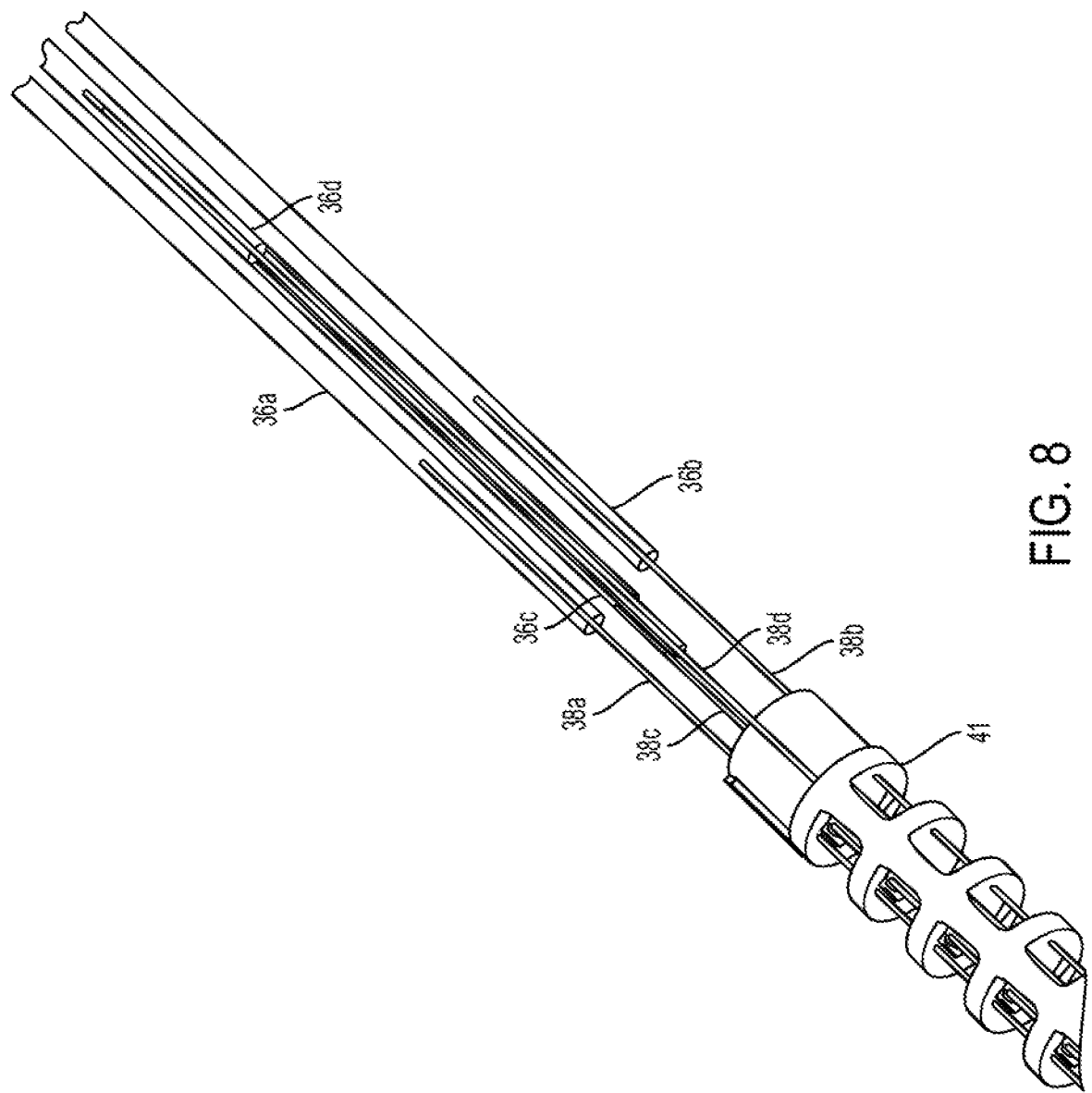
FIG. 8 is a perspective, partial view of a flexible outer shell and actuation shafts of the device of FIG. 1.
Figure 9:
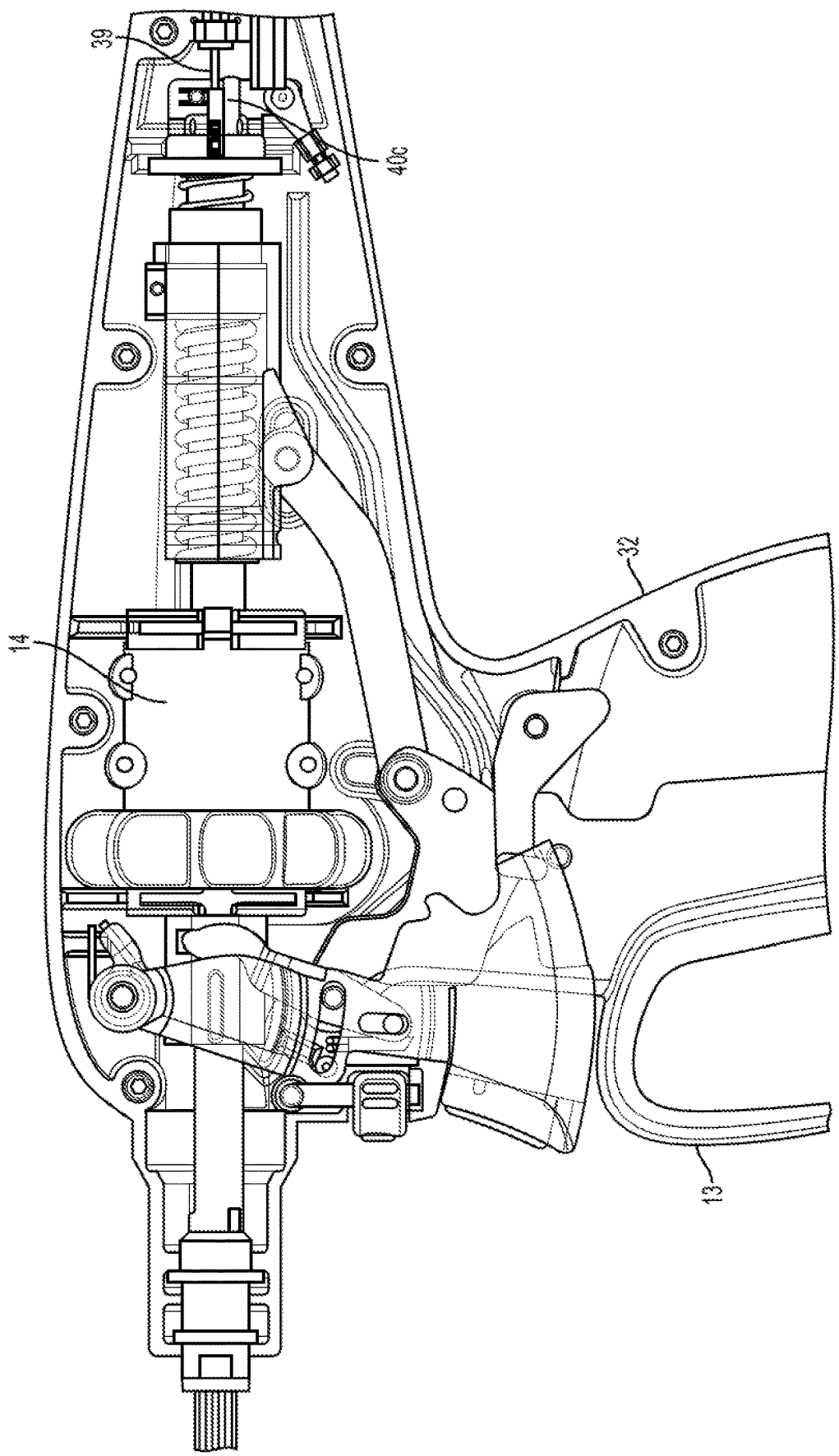
FIG. 9 is a side, partially transparent view of a proximal portion of the surgical device of FIG. 1 with a movable handle thereof in an open position and with select elements of the device omitted for clarity of illustration.
Figure 13:
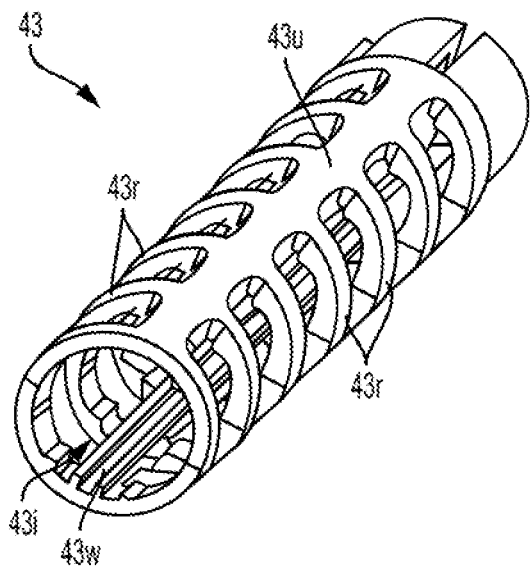
FIG. 13 is a perspective view of the flexible outer shell of the surgical device of FIG. 1.

The device 2 can include a bend region 41 configured to facilitate articulation of the end effector 8. The bend region can include a flexible outer shell 43, shown in FIGS. 3 and 8, and shown in FIG. 13 as a standalone element. The flexible outer shell 43 can, as a flexible member, be configured to flex or bend without cracking, breaking, or otherwise becoming damaged, which can facilitate articulation of the end effector 8. The flexible outer shell 43 can have an inner lumen 43i extending therethrough, an upper spine 43u extending longitudinally therealong, a lower spine 43w extending longitudinally therealong, and a plurality of spaced ribs 43r extending between the upper and lower spines 43u, 43w on either side (e.g., left and right sides) of the flexible outer shell 43. The first, second, third, and fourth actuation shafts and the RF cable 39 can each extend through the inner lumen 43i of the flexible outer shell 43, as shown in FIGS. 3 and 8. Exemplary embodiments of flexible outer shells are further described in U.S. Pat. Pub. No. 2012/0078247 entitled "Articulation Joint Features For Articulating Surgical Device" filed on Sep. 19, 2011, and in U.S. application Ser. No. 14/659,037 entitled "Flexible Neck For Surgical Instruments" filed on Mar. 16, 2015, which are hereby incorporated by reference in their entireties.

Figure 10:
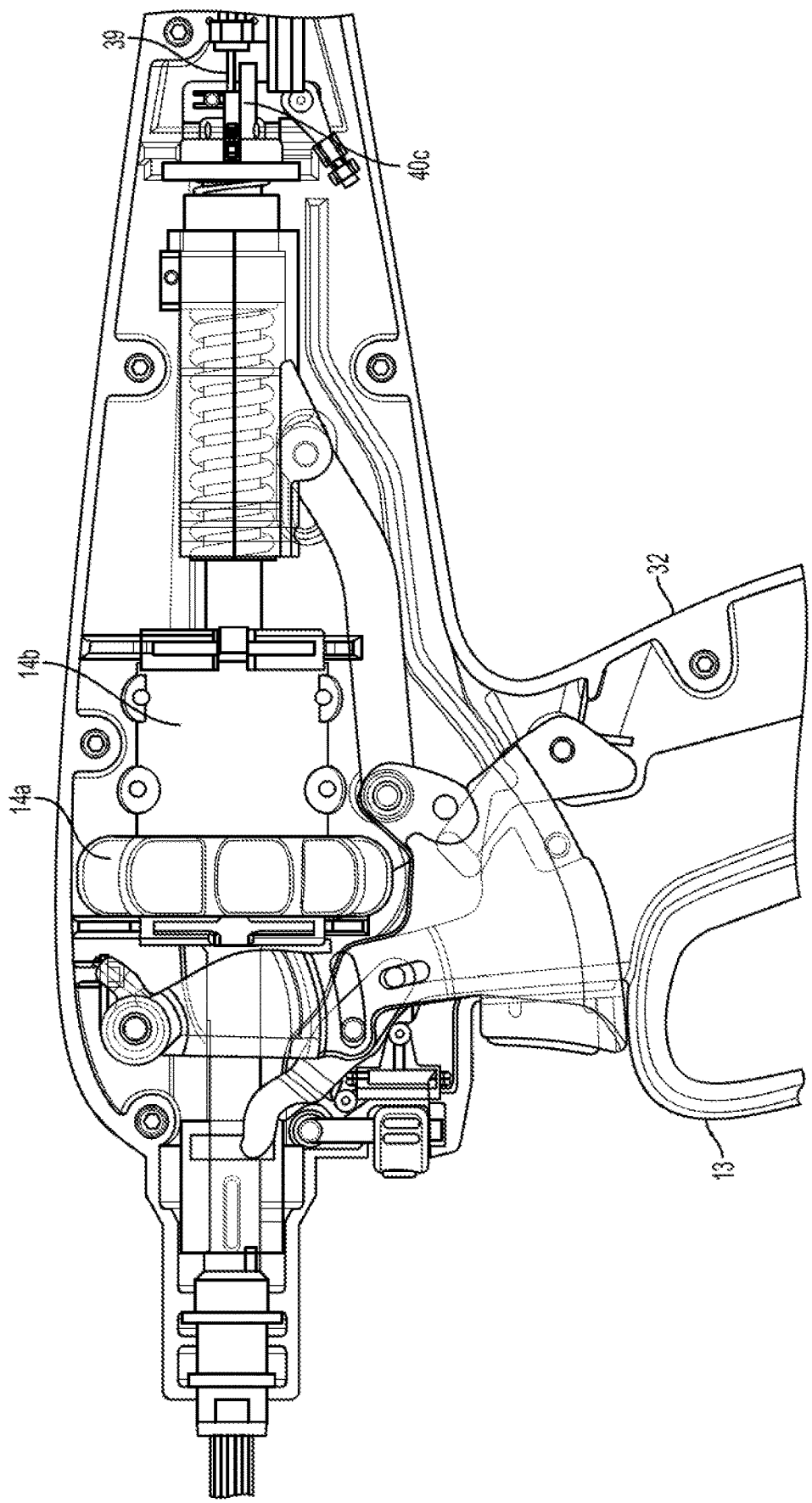
FIG. 10 is a side, partially transparent view of the proximal portion of the surgical device of FIG. 9 with select elements of the device omitted for clarity of illustration and with the movable handle thereof in a closed position.
Figure 15:
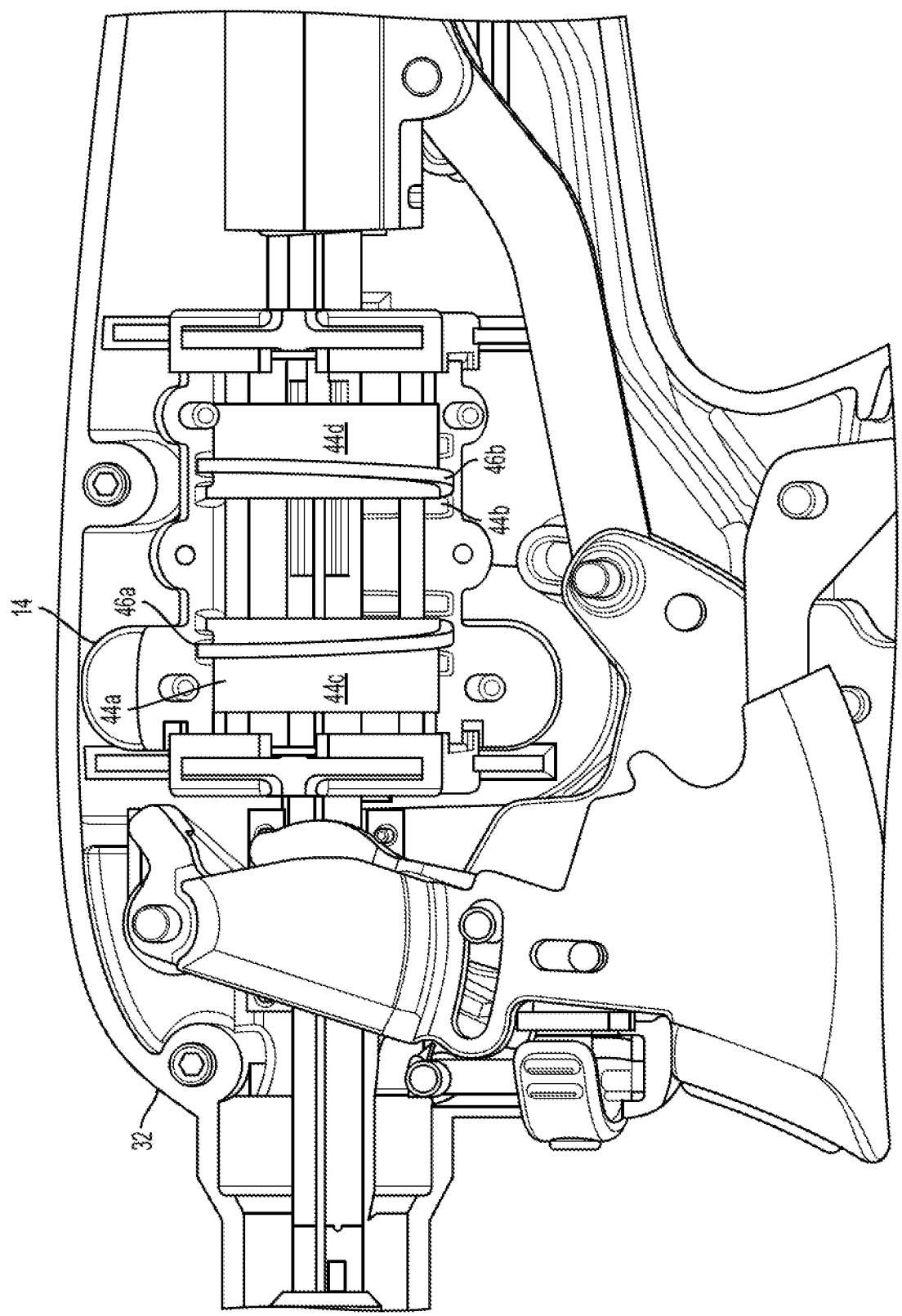
FIG. 15 is a side, partial view of a handle portion of the surgical device of FIG. 1 with select elements of the device omitted for clarity of illustration.

As mentioned above, the second actuator 14 can be configured to facilitate articulation of the end effector 8, which as also mentioned above, can include bending or flexing of the flexible outer shell 34. The actuation mechanism operatively connected to the second actuator 14 can have a variety of sizes, shapes, and configurations. As in this illustrated embodiment, the actuation mechanism can be coupled to the proximal handle portion 4 of the device 2 and can include the second actuator 14, which as described herein can be configured to be manually actuated by a user to effect articulation of the end effector 8. FIG. 14 illustrates the second actuator 14 as a standalone element, and FIG. 15 shows the second actuator 14 in cross-section. As illustrated in FIGS. 1, 10, and 14, the second actuator 14 can include a ring-shaped portion 14a configured to be accessible to a user outside the main housing 32 and can include an elongate tubular portion 14b extending proximally from the ring-shaped portion and being configured to be contained within the main housing 32. The second actuator 14 can thus be cannulated.

The second actuator 14 can include first and second threads 42a, 42b formed in an internal surface 14i thereof. The first thread 42a can be associated with the first actuation shaft, and the second thread 42b can be associated with the second actuation shaft, as discussed further below. The first and second threads 42a, 42b can be independent from one another, as in this illustrated embodiment, with each of the first and second threads 42a, 42b defining separate paths. The first and second threads 42a, 42b can wind in opposite directions around the second actuator 14, e.g., one left-handed and one right-handed. The first and second threads 42a, 42b can have any length around the second actuator's internal surface 42i. In an exemplary embodiment, the first and second threads 42a, 42b can have the same length around the second actuator's internal surface 42i, which can facilitate symmetrical articulation of the end effector 8. The first and second threads 42a, 42b in this illustrated embodiment includes grooves configured to mate with corresponding protrusions configured to slide within the grooves. In other embodiments, the first and second threads 42a, 42b of the second actuator 14 can include protrusions configured to slidably mate with corresponding grooves.

Figure 11:
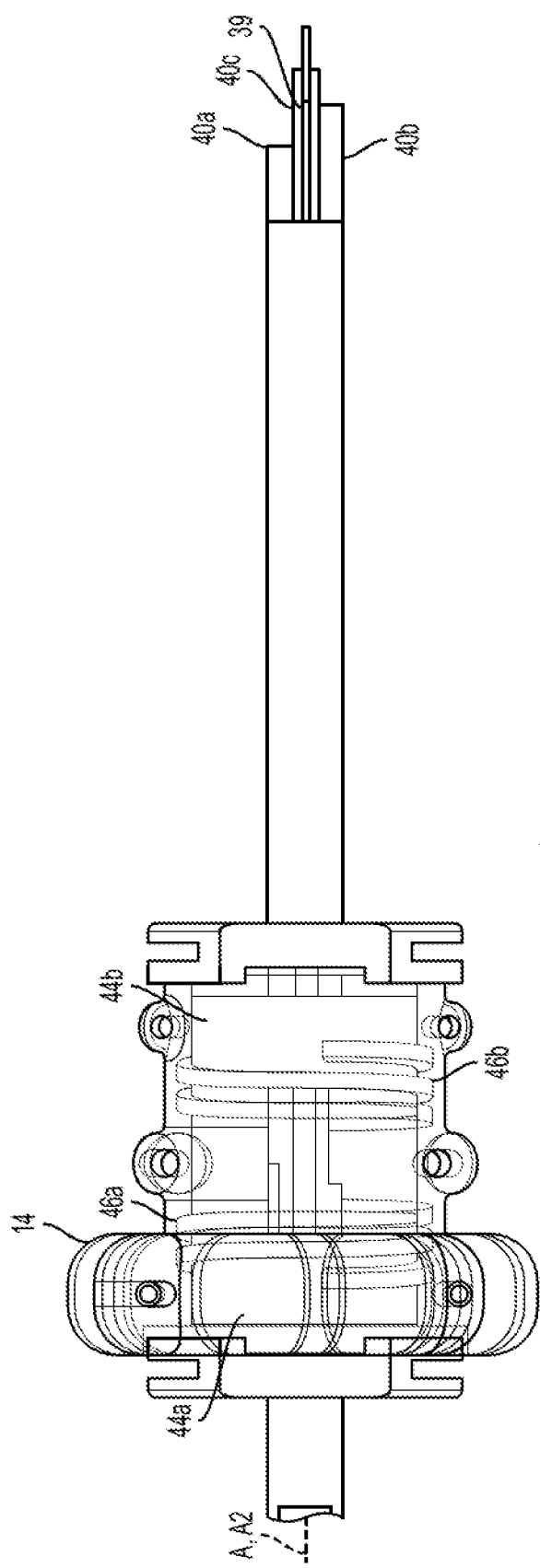
FIG. 11 is a side view of an actuation mechanism and actuation shafts of the surgical device of FIG. 1 in a first position.

The actuation mechanism can include first and second nuts 44a, 44b, also referred to herein as "drums," configured to movably mate with the second actuator 14. The first and second drums 44a, 44b can have a variety of sizes, shapes, and configurations. The first nut 44a can be associated with the first actuation shaft, and the second nut 44b can be associated with the second actuation shaft, as discussed further below. As in this illustrated embodiment, each of the first and second drums 44a, 44b can be generally cylindrical in shape and can be cannulated. The first and second drums 44a, 44b can each be configured to be disposed within the cannulated interior of the second actuator 14, as illustrated in FIGS. 11 and 15.

The first drum 44a can include a third thread 46a on an exterior surface 44c thereof that can be configured to threadably mate with the first thread 42a of the second actuator 14, and the second drum 44b can include a fourth thread 46b on an exterior surface 44d thereof that can be configured to threadably mate with the second thread 42b of the second actuator 14. The third and fourth threads 46a, 46b can be independent from one another, as in this illustrated embodiment, with each of the third and fourth threads 46a, 46b defining separate paths. The third and fourth threads 46a, 46b can wind in opposite directions around their respective drums 44a, 44b, e.g., one left-handed and one right-handed, thereby facilitating their mating with the opposite right- and left-hands of the first and second threads 42a, 42b. The third and fourth threads 46a, 46b can have any length around their respective drums' exterior surfaces 44c, 44d. In an exemplary embodiment, the third and fourth threads 46a, 46b can have the same length around their respective drums' exterior surfaces 44c, 44d, which can facilitate symmetrical articulation of the end effector 8. The third and fourth threads 46a, 46b in this illustrated embodiment includes protrusions configured to slidably mate with corresponding grooves (e.g., the grooves 42a, 42b), but in other embodiments, the third and fourth threads 46a, 46b can include grooves configured to slidably mate with corresponding protrusions.

In response to actuation of the second actuator 14, e.g., in response to a user's rotation of the second actuator 12, the second actuator 14 can be configured to rotate about a longitudinal axis A2 (shown in FIG. 11) thereof. As in this illustrated embodiment, the second actuator's longitudinal axis A2 can be coaxial with the shaft assembly's longitudinal axis A. The second actuator 14 can be configured to remain stationary along its longitudinal axis A2 during the rotation. In other words, the second actuator 14 can be configured to not move distally or proximally during its rotation. The rotation of the second actuator 14 can cause the first and second drums 44a, 44b disposed within the second actuator 14 and threadably engaged therewith (e.g., the first thread 42a threadably engaged with the third thread 46a, and the second thread 42b threadably engaged with the fourth thread 46b) to simultaneously move. The opposed threading of the first and second threads 42a, 42b, and their corresponding third and fourth threads 46a, 46b of the first and second drums 44a, 44b, can cause the first and second drums 44a, 44b to move in opposite directions. One of the first and second drums 44a, 44b can move proximally, and the other of the first and second drums 44a, 44b can move distally. The movement of the first and second drums 44a, 44b can include longitudinal translation along the second actuator's longitudinal axis A2, which as in this illustrated embodiment, can also be along the shaft assembly's longitudinal axis A. The first and second drums 44a, 44b can be configured to alternately move distally and proximally during the actuation of the second actuator 14. In other words, rotation of the second actuator 14 in a same direction, whether it be clockwise or counterclockwise, can cause the first drum 44a to first move distally and the second drum 44b to move proximally, and then cause the first and second drums 44a, 44b to switch directions so that the first drum 44a moves proximally and the second drum 44b moves distally. The first actuator shaft can be operatively connected to the first drum 44a, as discussed herein, such that the movement of the first drum 44a can cause a force to be applied to the first actuator shaft and thereby cause corresponding movement of the first actuator shaft, e.g., longitudinal translation of the first drum 44a in a proximal direction can cause longitudinal translation of the first actuator shaft in the proximal direction. The second actuator shaft can be operatively connected to the second drum 44b, as discussed herein, such that the movement of the second drum 44b can cause a force to be applied to the second actuator shaft and thereby cause corresponding movement of the second actuator shaft, e.g., longitudinal translation of the second drum 44b in a distal direction can cause longitudinal translation of the second actuator shaft in the distal direction. The movement of the first and second actuator shafts can be configured to cause the end effector 8 to articulate.

The first actuator shaft can be operatively connected to the first drum 44a and the second actuator shaft can be operatively connected to the second drum 44b in a variety of ways. For example, as mentioned above, the first and second stabilizing members 35a, 35b can be seated within their respective associated drums 44a, 44b.

The first and second stabilizing members 35a, 35b can be configured to facilitate actuation of the second actuator 14, and hence facilitate articulation of the end effector 8, regardless of the rotational position of the shaft assembly 6 about the shaft assembly's longitudinal axis A. In other words, the third actuator 16 can be configured to be at any rotational position about the longitudinal axis A when the second actuator 14 is actuated to articulate the end effector 8. The rotation of the shaft assembly 6 can rotate the first and second actuation shafts of the shaft assembly 6, as discussed herein, which adjusts the position of the first and second actuation shafts relative to the second actuator 14 and to the actuation mechanism. The first and second stabilizing members 35a, 35b can be configured to rotate within and relative to their respective drums 44a, 44b during rotation of the shaft assembly 6 in response to actuation of the third actuator 16. Accordingly, regardless of the rotational position of the first and second stabilizing members 35a, 35b relative to their respective drums 44a, 44b, the first and second actuation shafts coupled to the first and second stabilizing members 35a, 35b can be moved proximally/distally in response to the proximal/distal movement of the drums 44a, 44b during actuation of the second actuator 14. Similar to the first and second stabilizing members 35a, 35b, the third stabilizing member 35d can be configured to facilitate actuation of the fourth actuator 18, and hence facilitate movement of the cutting element 26, regardless of the rotational position of the shaft assembly 6 about the shaft assembly's longitudinal axis A.

FIGS. 11 and 19-21 illustrate an embodiment of the actuation of the second actuator 14 and the movement of the first and second drums 44a, 44b in response thereto, thereby causing movement of the first and second actuation shafts and, hence, causing articulating movement of the end effector 8. FIG. 11 illustrates a first position of the second actuator 14 in which the first and second drums 44a, 44b are at their outermost positions relative to one another, with the first drum 44a being as far distal as possible for the first drum 44a and the second drum 44b being as far proximal as possible for the second drum 44b. The second actuation shaft is located more proximally than the first actuation shaft, as shown by the more proximal position of the second tube 40b as compared to the first tube 40a. The end effector 8 is accordingly articulated to the left, e.g., articulated in the second direction D2 (see FIG. 3), with the first and second distal elongate members 38a, 38b and the flexible outer shell 43 bent in the bend region 41, since the second actuation shaft is tensioned proximally, and is hence pulling on the left side of the end effector 8 to urge articulation to the left, and since the first actuation shaft is tensioned distally, and is hence pushing on the right side of the end effector 8 to urge articulation to the left.

FIG. 19 illustrates a second position of the second actuator 14 in which the second actuator 14 has been rotated clockwise from the first position of FIG. 11. The rotation of the second actuator 14 has caused the first drum 44a to move proximally and the second drum 44b to move distally. The first drum 44a has moved within the second actuator 14 due to the first drum's threaded engagement with the second actuator's first thread 42a, and the second drum 44b has moved within the second actuator 14 due to the second drum's threaded engagement with the second actuator's second thread 42b. The rotation of the second actuator 14 has caused the first and second drums 44a, 44b to move closer together so as to be separated from each other by less distance than in FIG. 11. The proximal movement of the first drum 44a has caused the first actuation shaft operatively connected thereto to correspondingly move proximally, as shown by the more proximal position of the first tube 40a in FIG. 19 as compared to FIG. 11. Similarly, the distal movement of the second drum 44b has caused the second actuation shaft operatively connected thereto to correspondingly move distally, as shown by the more distal position of the second tube 40b in FIG. 19 as compared to FIG. 11. The end effector 8 has accordingly moved to the right, e.g., in the first direction D1 (see FIG. 3), from its position in FIG. 11. The RF cable 39, the third actuation shaft, and the fourth actuation shaft have not moved in response to the actuation of the second actuator 14 between FIGS. 11 and 19.

FIG. 20 illustrates a third position of the second actuator 14 in which the second actuator 14 has been rotated clockwise from the second position of FIG. 19. The rotation of the second actuator 14 has caused the first drum 44a to move proximally and the second drum 44b to move distally. The rotation of the second actuator 14 has caused the first and second drums 44a, 44b to move closer together so as to be separated from each other by less distance than in FIG. 19. The proximal movement of the first drum 44a has caused the first actuation shaft operatively connected thereto to correspondingly move proximally, as shown by the more proximal position of the first tube 40a in FIG. 20 as compared to FIG. 19. Similarly, the distal movement of the second drum 44b has caused the second actuation shaft operatively connected thereto to correspondingly move distally, as shown by the more distal position of the second tube 40b in FIG. 20 as compared to FIG. 19. The end effector 8 has accordingly moved further to the right, e.g., in the first direction D1 (see FIG. 3), from its position in FIG. 19. The RF cable 39, the third actuation shaft, and the fourth actuation shaft have not moved in response to the actuation of the second actuator 14 between FIGS. 19 and 20.

Figure 21:
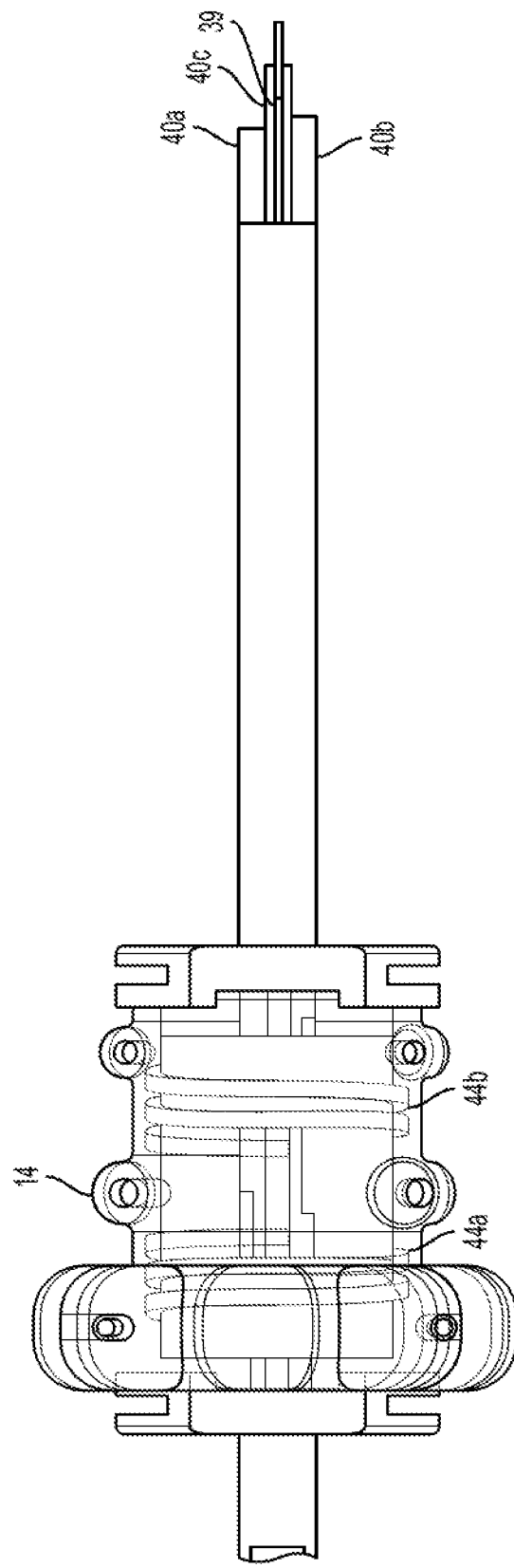
FIG. 21 is a side view of the actuation mechanism and actuation shafts of FIG. 20 moved from the third position to a fourth position.

FIG. 21 illustrates a fourth position of the second actuator 14 in which the second actuator 14 has been rotated clockwise from the third position of FIG. 20. The rotation of the second actuator 14 has caused the first drum 44a to move distally and the second drum 44b to move proximally. The rotation of the second actuator 14 has caused the first and second drums 44a, 44b to move closer together so as to be separated from each other by more distance than in FIG. 20. The distal movement of the first drum 44a has caused the first actuation shaft operatively connected thereto to correspondingly move distally, as shown by the more distal position of the first tube 40a in FIG. 21 as compared to FIG. 20. Similarly, the proximal movement of the second drum 44b has caused the second actuation shaft operatively connected thereto to correspondingly move proximally, as shown by the more proximal position of the second tube 40b in FIG. 21 as compared to FIG. 20. The end effector 8 has accordingly moved to the left, e.g., in the first direction D2 (see FIG. 3), from its position in FIG. 20. The RF cable 39, the third actuation shaft, and the fourth actuation shaft have not moved in response to the actuation of the second actuator 14 between FIGS. 20 and 21.

The second actuator 14 can continue rotating clockwise after the fourth position of FIG. 21, continually moving the first drum 44a longitudinally proximally and distally and moving the second drum 44b alternately to the first drum 44a, e.g., distally when the first drum 44a is moving proximally. The second actuator 14 can be rotated counterclockwise at any point, e.g., before, between, or after any of the first, second, third, and fourth positions, which can allow the end effector's angular position to be angled as desired during the course of performance of a surgical procedure and/or can help accommodate right-handed and left-handed users. The second actuator 14 can stop being rotated at any time so as to hold the end effector 8 in position, whether articulated or unarticulated.

Figure 22:
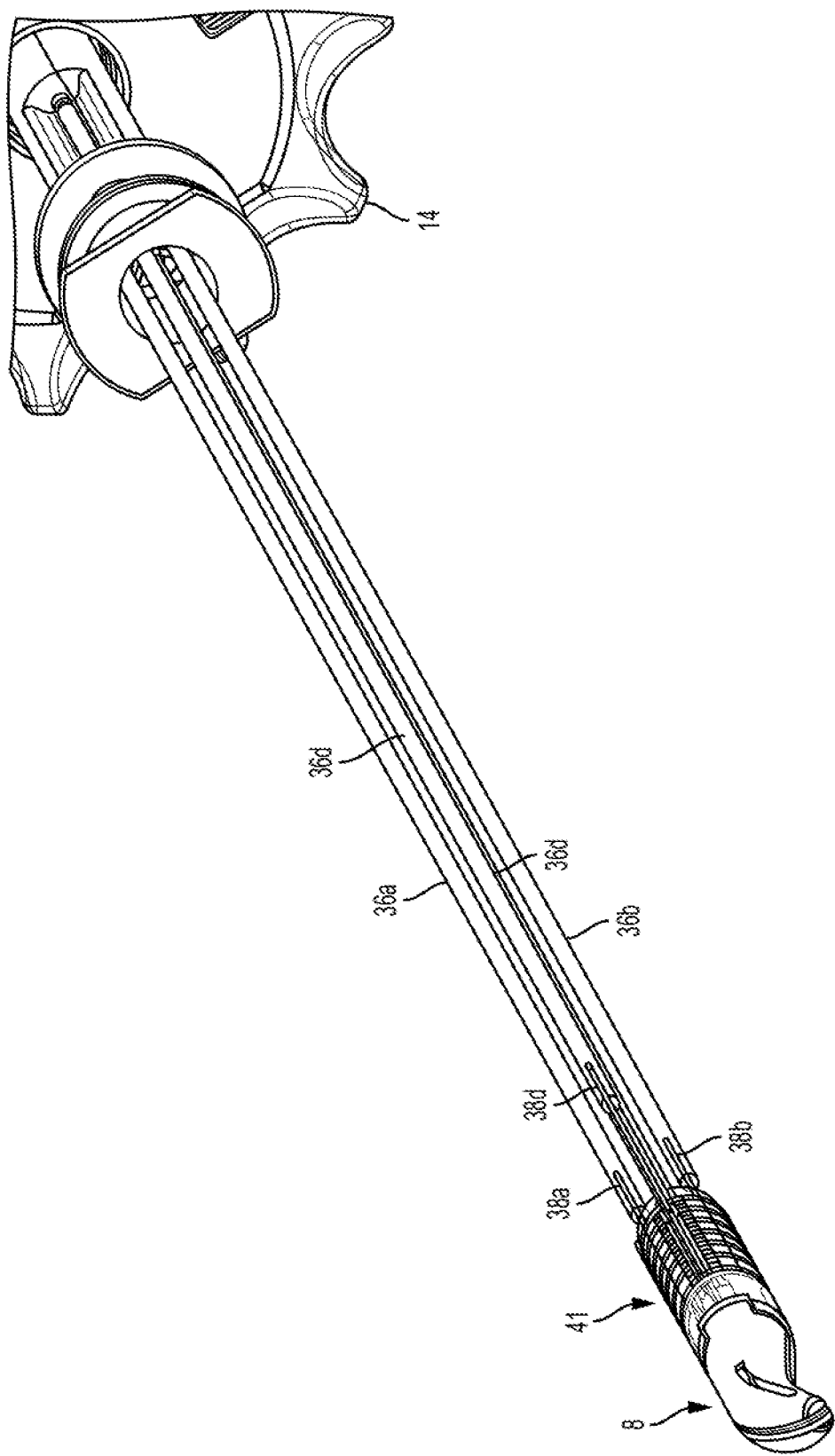
FIG. 22 is a perspective view of a distal portion of the surgical device of FIG. 1 with first and second actuation shafts of the device in a first position and with select elements of the device omitted for clarity of illustration.
Figure 23:
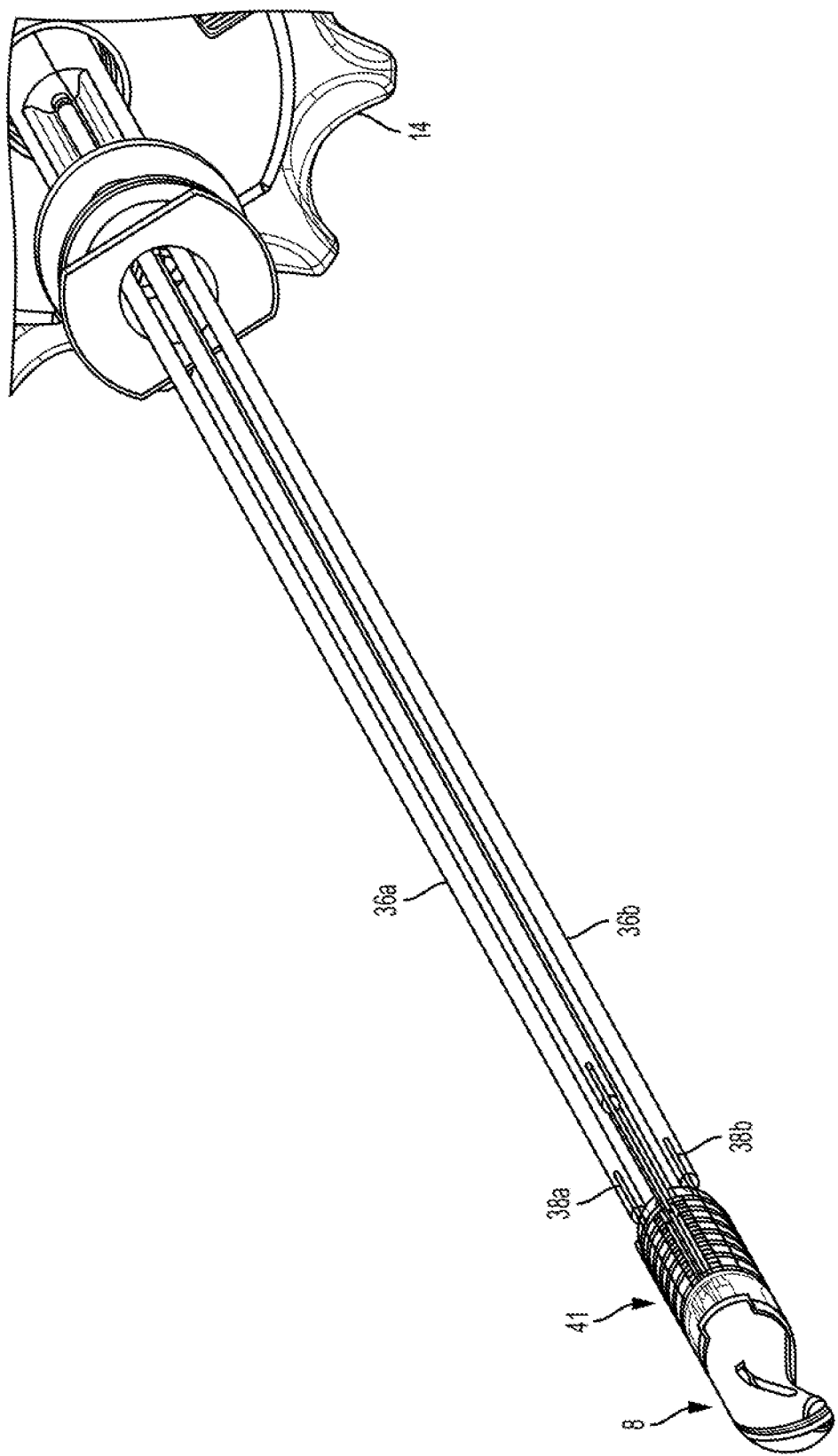
FIG. 23 is a perspective view of a distal portion of the surgical device of FIG. 22 with select elements of the device omitted for clarity of illustration and with the first and second actuation shafts of the device moved from the first position to a second position.
Figure 24:
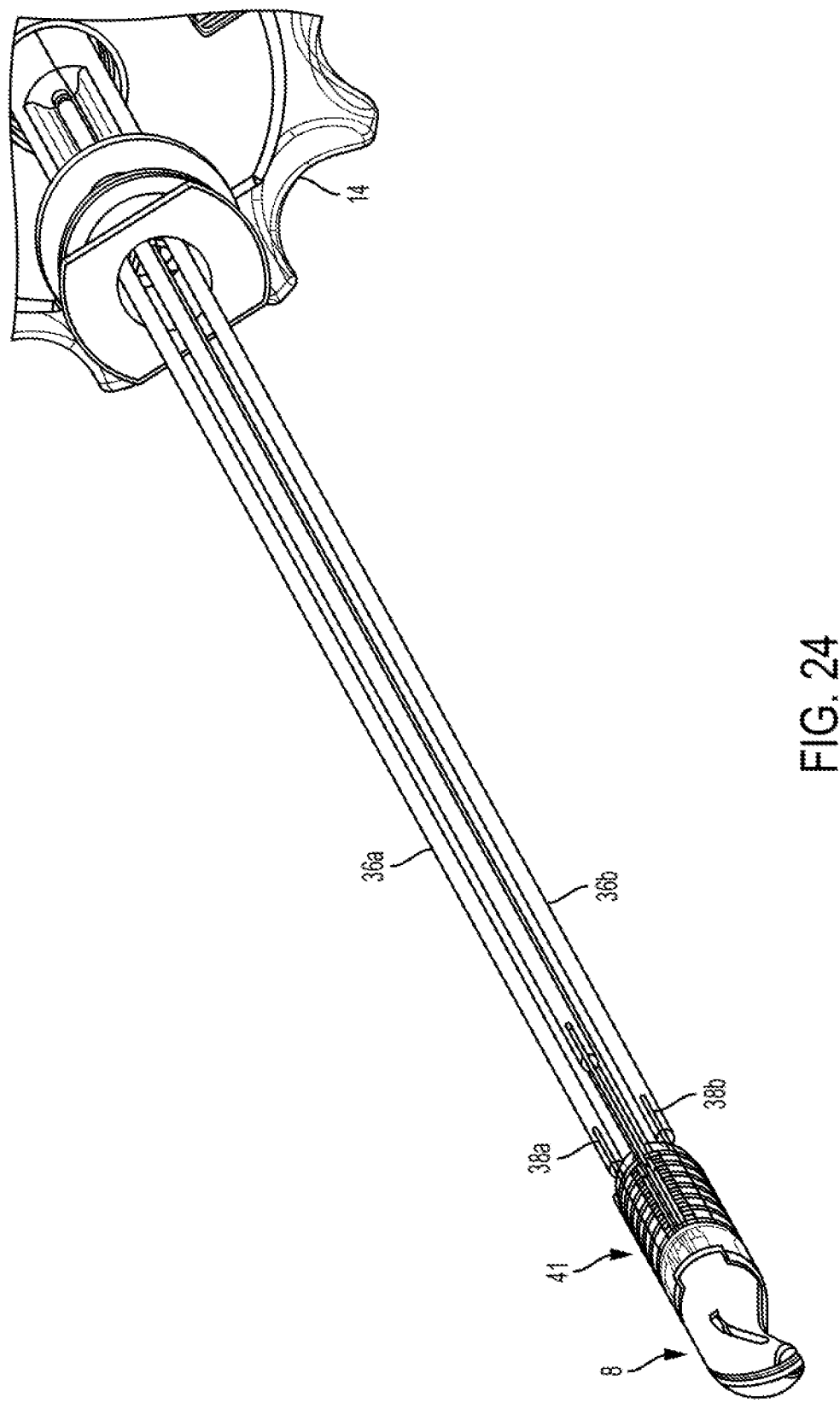
FIG. 24 is a perspective view of a distal portion of the surgical device of FIG. 23 with select elements of the device omitted for clarity of illustration and with the first and second actuation shafts of the device moved from the second position to a third position.
Figure 25:
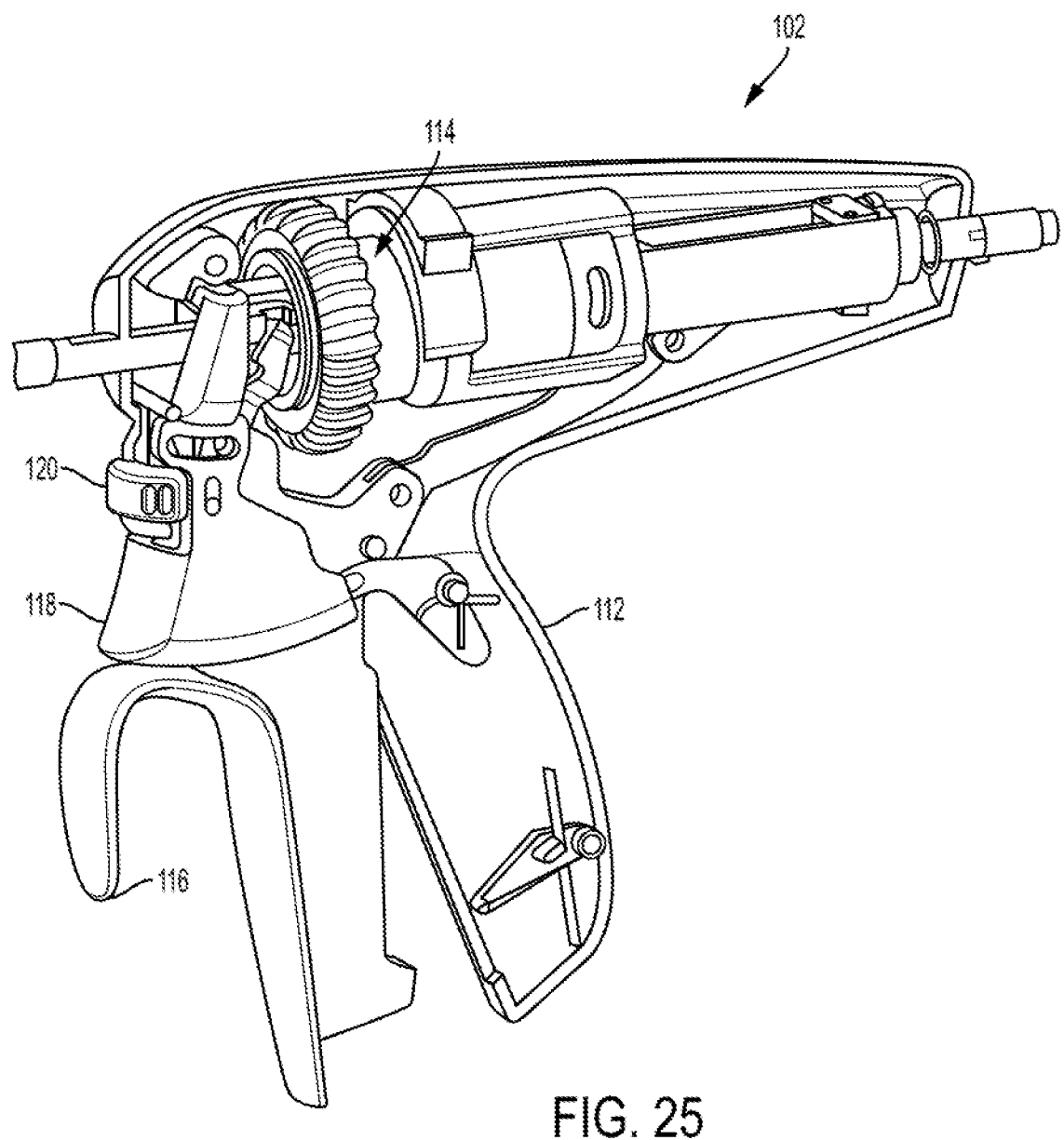
FIG. 25 is a perspective view of a proximal portion of another embodiment of a surgical device with select elements of the device omitted for clarity of illustration.
Figure 26:
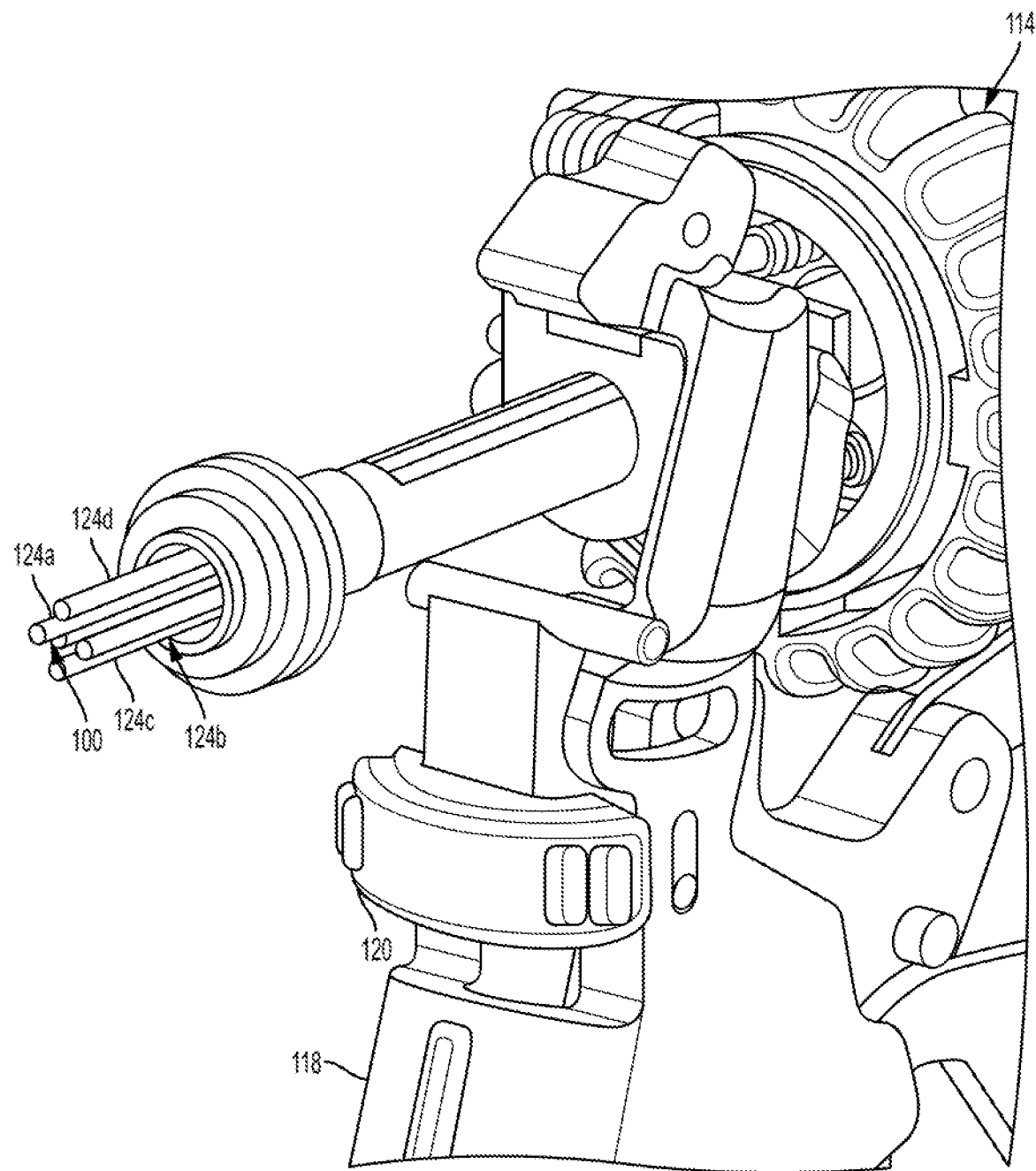
FIG. 26 is a perspective view of a portion of the surgical device of FIG. 25 with select elements of the device omitted for clarity of illustration.

FIGS. 22-24 illustrate another embodiment of the actuation of the second actuator 14 and the movement of the first and second drums 44a, 44b in response thereto, thereby causing movement of the first and second actuation shafts and, hence, causing articulating movement of the end effector 8. For ease of illustrating movement of the first and second actuator shafts in FIGS. 23 and 24, the end effector 8 is illustrated in its unarticulated position to avoid obscuring other elements of the device 2 although the end effector 8 would be articulated in view of the positions of the first and second actuation shafts in FIGS. 23 and 24, as discussed below. FIG. 22 illustrates the end effector 8 in the unarticulated position, in which the first and second actuation shafts are substantially equally tensioned so as to not exert a force on the end effector 8 and cause articulation thereof. A person skilled in the art will appreciate that the tensions may not be precisely equal but nevertheless be considered to be substantially equal due to, e.g., manufacturing tolerances. Distal ends of the first and second proximal elongate members 36a, 36b are substantially aligned when the end effector 8 is in the unarticulated position, and distal ends of the first and second distal elongate members 38a, 38b are substantially aligned when the end effector 8 is in the unarticulated position.

FIG. 23 illustrates a subsequent position of the second actuator 14 from FIG. 22 after rotation of the second actuator in the clockwise direction. The first actuation shaft has moved proximally in response to the second actuator's actuation, as shown by the first proximal elongate member 36a and the first distal elongate member 38a each being moved proximally from their positions in FIG. 22. The second actuation shaft has moved distally in response to the second actuator's actuation, as shown by the second proximal elongate member 36b and the second distal elongate member 38b each being moved distally from their positions in FIG. 22. The end effector 8 would accordingly be articulated right, e.g., in the first direction D1 (see FIG. 3). The third and fourth actuation shaft have not moved in response to the actuation of the second actuator 14 between FIGS. 22 and 23.

FIG. 24 illustrates a subsequent position of the second actuator 14 from FIG. 23 after rotation of the second actuator in the clockwise direction. The first actuation shaft has moved distally in response to the second actuator's actuation, as shown by the first proximal elongate member 36a and the first distal elongate member 38a each being moved distally from their positions in FIG. 23. The second actuation shaft has moved proximally in response to the second actuator's actuation, as shown by the second proximal elongate member 36b and the second distal elongate member 38b each being moved proximally from their positions in FIG. 23. The end effector 8 would accordingly be articulated to the left, e.g., in the second direction D2 (see FIG. 3), from its articulated position in FIG. 23. The third and fourth actuation shaft have not moved in response to the actuation of the second actuator 14 between FIGS. 23 and 24.

FIG. 25-35 illustrate another embodiment of a surgical device. The device can generally be configured and used similar to the surgical device 2 of the embodiment of FIGS. 1-24 and similar to other embodiments of surgical devices described herein. The device can include a proximal handle portion 102, a shaft assembly 104 extending distally from the handle portion 102, and an end effector 106 including a pair of opposed jaws 108a, 108b and being coupled to a distal end of the shaft assembly 104 at a pivot joint 110. The device in this illustrated embodiment includes a conductive lead 100 (e.g., an RF cable, etc.) and can hence be powered.

The handle portion 102 can include a main housing 112, which can house a variety of elements therein and can have some elements accessible outside thereof, such as a first actuator 116 configured to effect the opening and closing of the opposed jaws 108a, 108b, a second actuator 114 configured to effect articulation of the end effector 106, a third actuator (not shown in FIGS. 25-35) configured to rotate the shaft assembly 104 and the end effector 106 about a longitudinal axis A3 of the shaft assembly 104, a fourth actuator 118 configured to translate a cutting element (obscured in FIGS. 25-35) along the end effector 106, and a fifth actuator 120 configured to turn on and off the application of energy, which includes RF energy in this illustrated embodiment.

Figure 28:
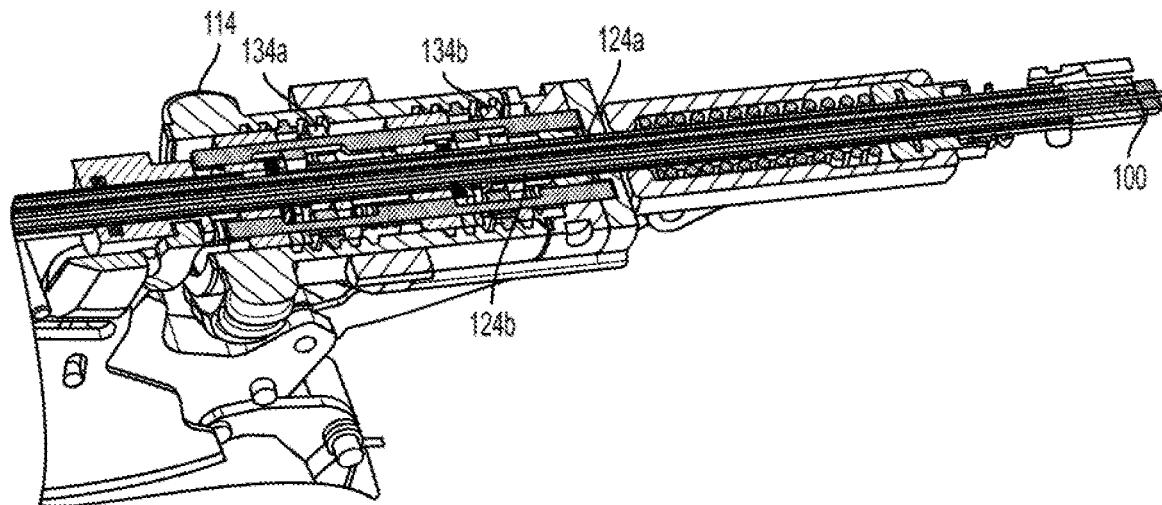
FIG. 28 is a cross-sectional perspective view of another portion of the surgical device of FIG. 25 with select elements of the device omitted for clarity of illustration.
Figure 29:
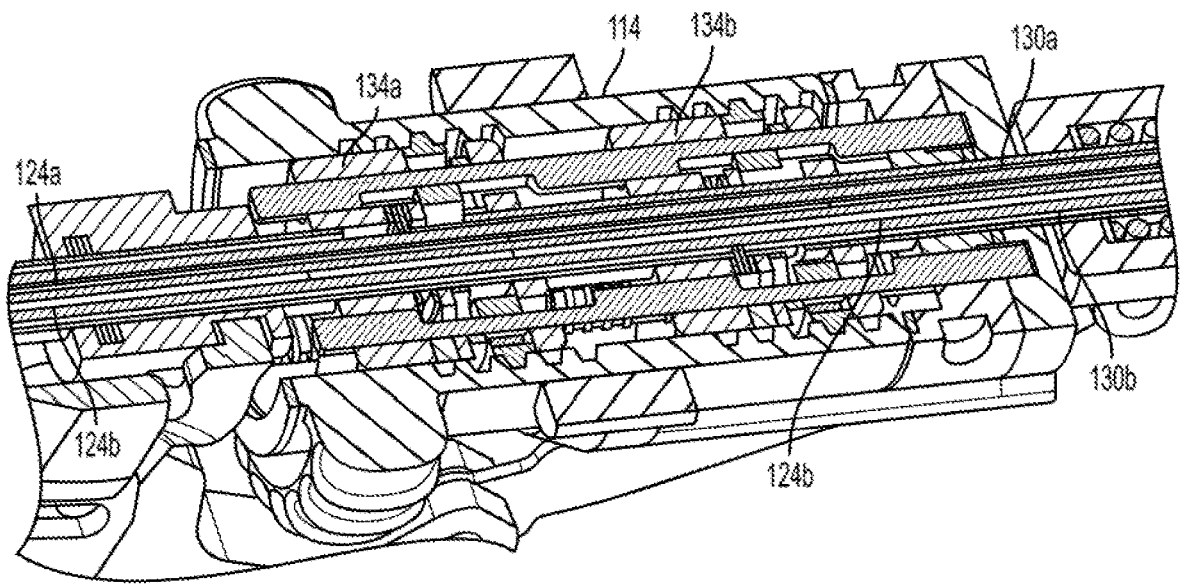
FIG. 29 is an enlarged view of a partial area of the portion of the surgical device of FIG. 28.
Figure 30:
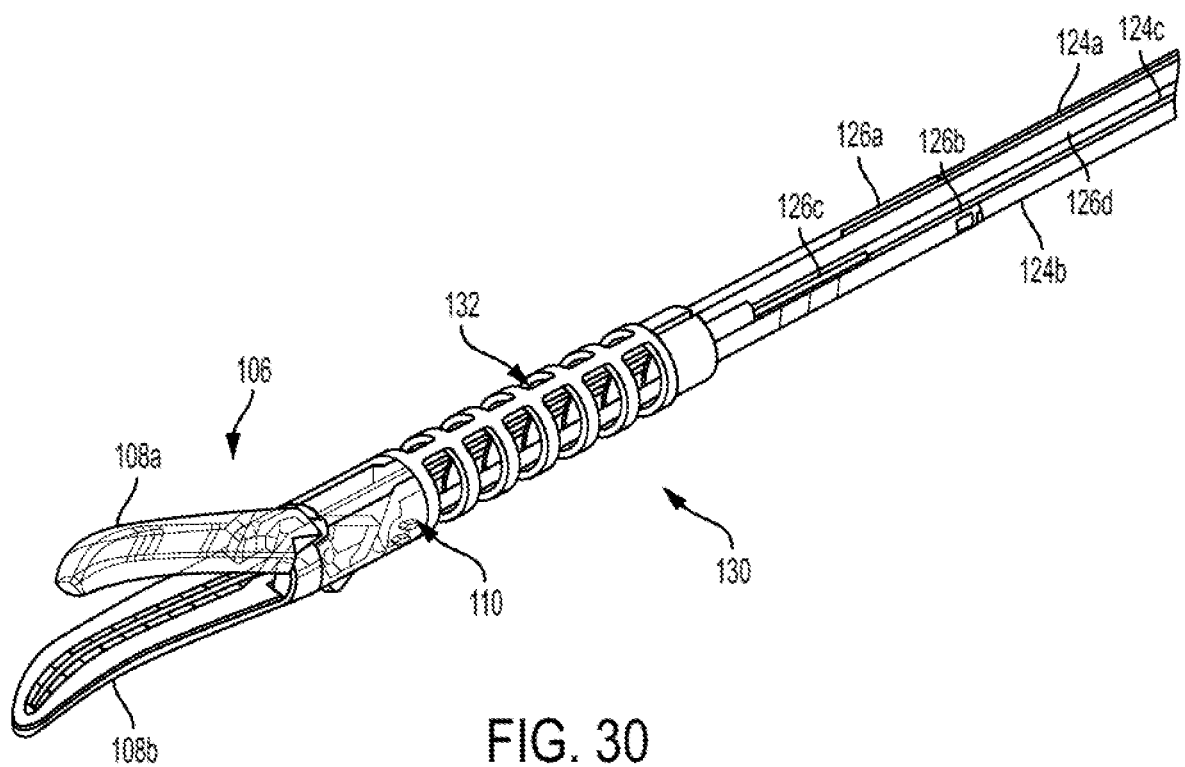
FIG. 30 is a perspective, partially transparent view of a distal portion of the surgical device of FIG. 25 with an outer elongate shaft of the device omitted for clarity of illustration.
Figure 31:
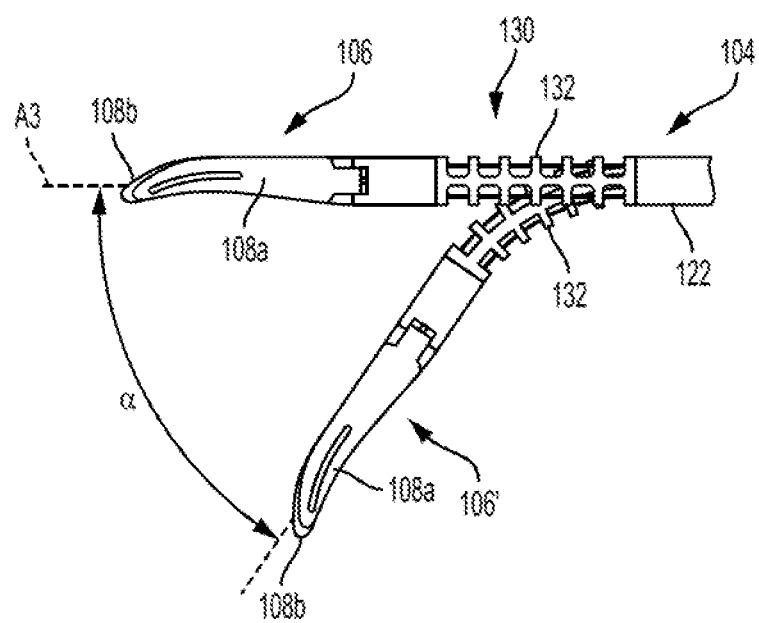
FIG. 31 is a top view of a distal portion of the surgical device of FIG. 25 showing an end effector of the device in an unarticulated position and in an articulated position.

The second actuator 114 configured to effect articulation of the end effector 106 can be operatively connected to an actuation mechanism, which can include first and second drums 134a, 134b. The second actuator 114 and the first and second drums 134a, 134b can be threadably engaged, as shown in FIGS. 28 and 29. FIGS. 30 and 31 illustrate the end effector 106 in an unarticulated position, e.g., at a zero angle relative to the longitudinal axis A3. FIG. 31 illustrates the end effector 106' in an articulated position, e.g., at an articulation angle α relative to the longitudinal axis A3, which in the illustrated embodiment of FIG. 31 is articulation to the left.

Figure 35:
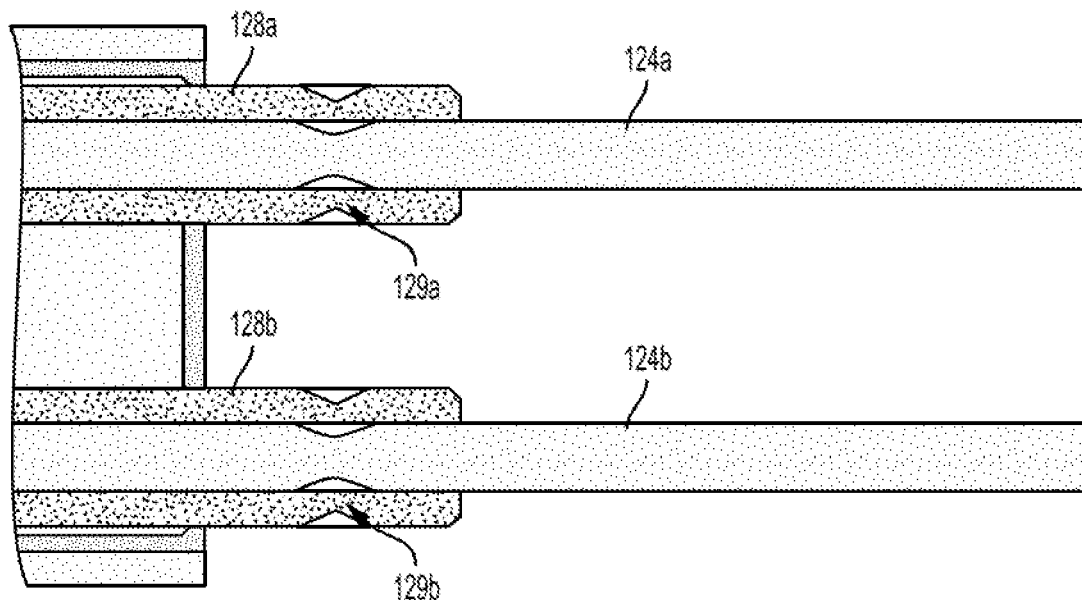
FIG. 35 is a side, cross-sectional view of select elements in a distal portion of the portion of the surgical device of FIG. 32.

The shaft assembly 104 can include an outer elongate shell 122 and at least one actuation shaft extending between the handle portion 102 and the end effector 106. In this illustrated embodiment, the device includes a first actuation shaft including a first proximal elongate member 124a, a first distal elongate member 126a having a proximal end attached to a distal end of the first proximal elongate member 124a, and a first tube 128a attached to the first proximal elongate member 124a; a second proximal elongate member 124b, a second distal elongate member 126b having a proximal end attached to a distal end of the second proximal elongate member 124b, and a second tube 128b attached to the second proximal elongate member 124b; a third proximal elongate member 124c, a third distal elongate member 126c having a proximal end attached to a distal end of the third proximal elongate member 124c, and a third tube 128c attached to the third proximal elongate member 124c; and a fourth proximal elongate member 124d, a fourth distal elongate member 126d having a proximal end attached to a distal end of the fourth proximal elongate member 124d, and a fourth tube 128d attached to the fourth proximal elongate member 124d. As shown in FIG. 35, the first and second proximal elongate members 124a, 124b are attached to their respective first and second tubes 128a, 128b in this illustrated embodiment by laser welding at connection areas 129a, 129b, but as mentioned herein, elongate members and tubes can be attached together in other ways (e.g., crimping, threading, etc.). Each of the conductive lead 100 and the first, second, third, and fourth actuation shafts can extend through a bend region 130 of the device that includes a flexible outer shell 132.

The device can include a first stabilizing member 136a including a pair of washers 138a and a clip 140a and being configured to couple the first actuation shaft to the second actuator 114, a second stabilizing member 136b including a pair of washers 138b and a clip 140b and being configured to couple the second actuation shaft to the second actuator 114, a third stabilizing member (not shown in FIGS. 25-35) configured to couple the third actuation shaft to the first actuator 116, a fourth stabilizing member 136c including a pair of washers 138c and a clip 140c and being configured to couple the fourth actuation shaft to the fourth actuator 118, and a fifth stabilizing member including a pair of washers (not shown in FIGS. 25-35) and a clip 140d and being configured to couple the conductive lead 100 to the fifth actuator 120.

Figure 36:
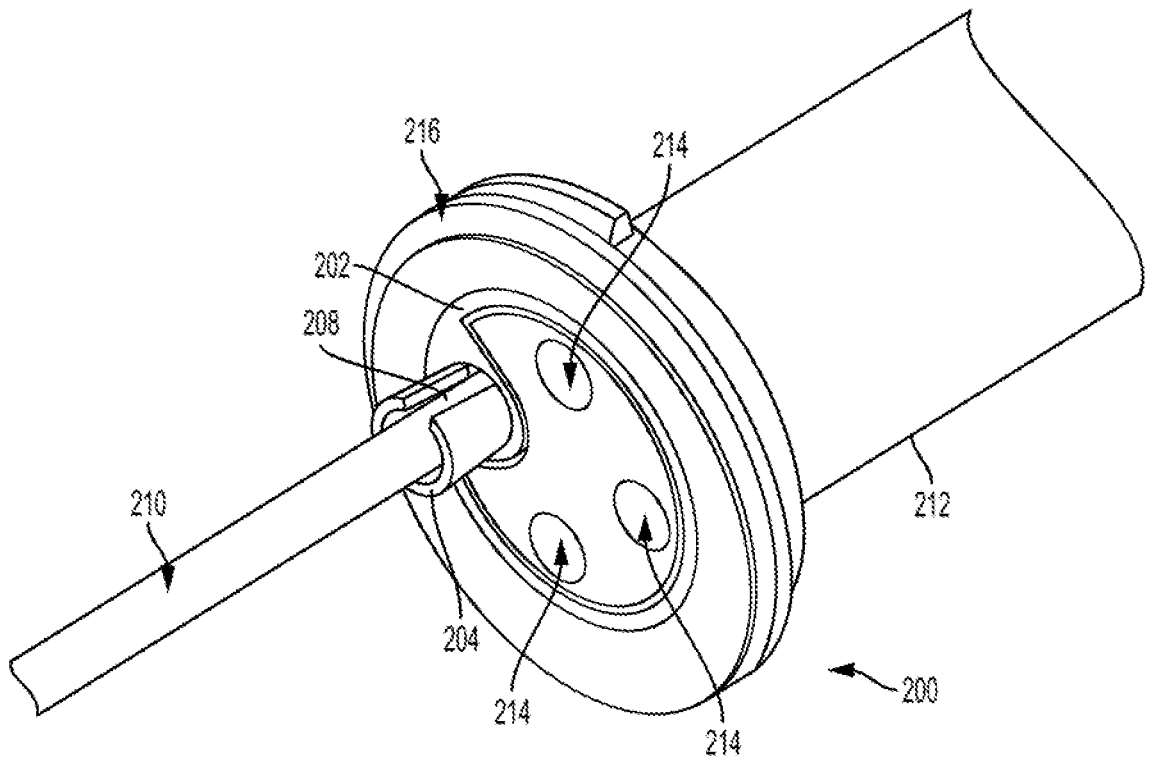
FIG. 36 is a perspective view of a portion of another embodiment of a surgical device with an actuation shaft of the device secured to a stabilizing member of the device.
Figure 37:
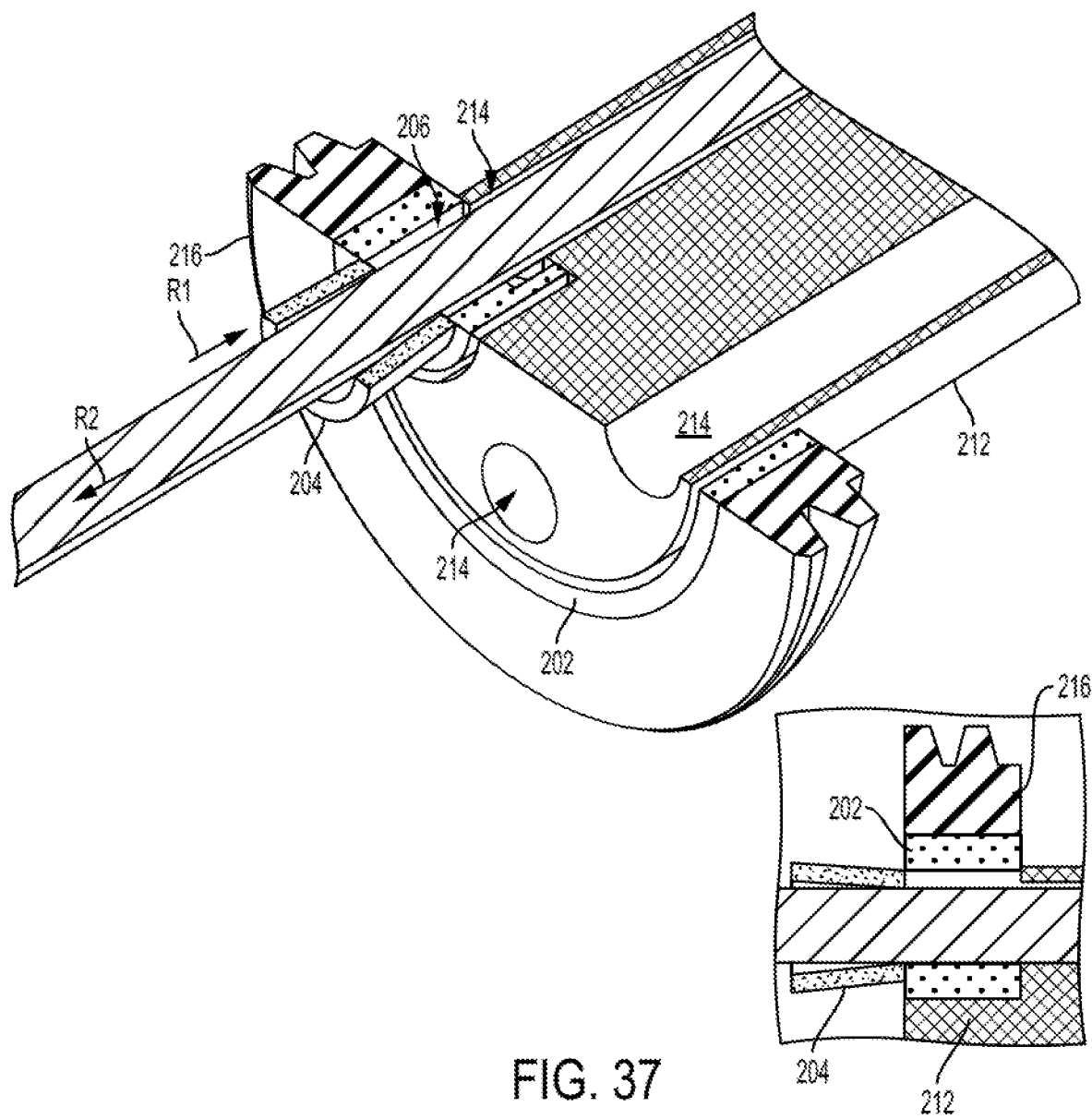
FIG. 37 is a perspective, cross-sectional view of the portion of the surgical device of FIG. 36 with the actuation shaft not being secured to the stabilizing member, with an inset showing a cross-sectional schematic view.

FIGS. 36 and 37 illustrate another embodiment of a stabilizing member 200 configured to facilitate operative connection of an actuation shaft 210 to an actuator. The actuation shaft 210 can generally be configured and used similar to other actuation shafts described herein. A proximal elongate member of the actuation shaft 210 is illustrated in FIGS. 36 and 37. The stabilizing member 200 in this illustrated embodiment can allow the actuation shaft 210 to be attached thereto using an interference fit. The interference fit can allow the actuation shaft 210 to be attached to the stabilizing member 200 without any modification needing to be made to the actuation shaft 210 to facilitate such attachment, e.g., no notch need be formed in the actuation shaft 210 to receive the stabilizing member, and/or can allow secure attachment between the actuation shaft 210 and the stabilizing member 200 without any other attachment technique needing to be used, e.g., welding, crimping, adhesive, etc. Another attachment technique can additionally be used, however, to help secure the actuation shaft 210 and the stabilizing member 200 together, such as by applying adhesive.

The stabilizing member 200 in this illustrated embodiment includes a washer 202 and a pin 204. The washer 202 can include an opening 206 formed therein that can be configured to receive the pin 204 therein. FIG. 36 illustrates the pin 204 positioned within the opening 206, and FIG. 37 illustrates the pin 204 outside the opening 206 in position to be advanced therein in a direction R1 toward the washer 202. In an exemplary embodiment, when the pin 204 is advanced into the opening 206 in the direction R1, the actuation shaft 210 can be moved in an opposite direction R2, which can help provide a tight interference fit to hold the actuation shaft 210 and the pin 204 in a fixed position relative to the washer 202. The pin 204 can be cannulated, which can allow the actuation shaft 210 to extend therethrough. The pin 204 can be tapered in the direction R1, which can facilitate insertion and securing of the pin 204 within the opening 206. The pin can have a longitudinal slot 208 formed therein, which can facilitate insertion of the pin 204 into the opening by allowing the pin's diameter to be reduced, and/or which can facilitate the pin 204 squeezing of the actuation shaft 210 by allowing the pin's diameter to be reduced. Instead of or in addition to the slot 208, the pin 204 can include another compression mechanism configured to facilitate compression of the pin 204 within the opening 206, such as scores in the pin's surface, holes formed in the pin 204, etc. The pin 204 can have any longitudinal length, but the pin's longitudinal length. in an exemplary embodiment is equal to or less than a depth of the opening 206, which can help prevent the pin 204 from extending out the other side of the opening 206 from which the pin 206 is inserted.

FIGS. 36 and 37 also show an embodiment of an outer shell 212 having a plurality of lumens 214 formed therein. The outer shell 212 has four lumens 214 in this illustrated embodiment, but as mentioned herein, an outer shell can have another number of lumens. The actuation shaft 210 and the outer shell 212 can generally be used and configured similar to the stabilizing members of the embodiment of FIGS. 1-24 and similar to other embodiments of stabilizing members described herein. The actuation shaft 210 in this illustrated embodiment is part of an actuation shaft configured to facilitate articulation of an end effector (not shown), but other actuation shafts can be similarly coupled to the stabilizing member 200. The opening 206 of the washer 202 can be aligned with a one of the lumens 214 for the actuation shaft 210 to facilitate extension of the proximal elongate member 212 therethrough.

FIGS. 36 and 37 also show an embodiment of a drum 216 of an actuation mechanism configured to facilitate end effector articulation. The washer 202 can be configured to be movably seated within a cannulated interior of the drum 216. The washer 202 can be configured to rotate about its longitudinal axis, which can be coaxial with a longitudinal axis of the outer shell 212 as in this illustrated embodiment, within the cannulated interior of the drum 216. This rotation can, as described herein, facilitate rotation of a shaft assembly including the actuation shaft 210.

Figure 38:
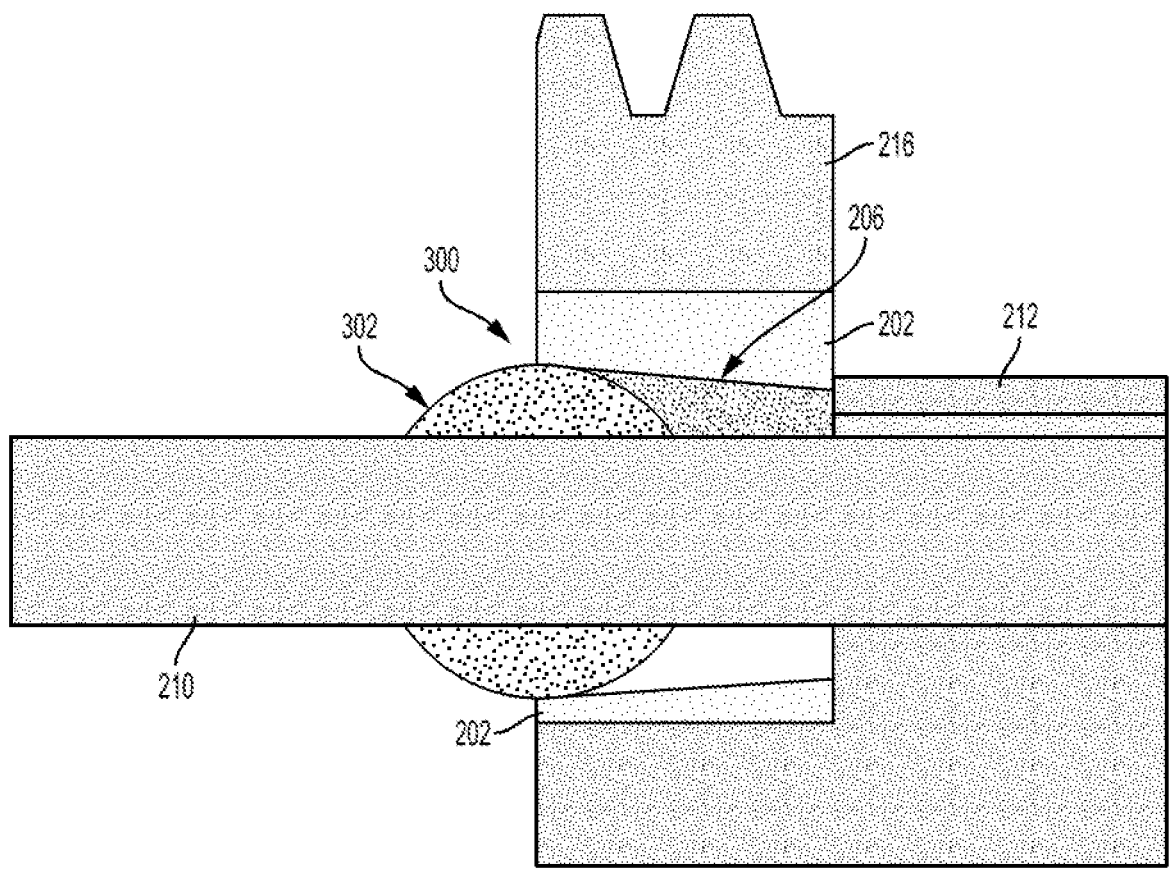
FIG. 38 is a side, cross-sectional view of a portion of yet another embodiment of a surgical device.

FIG. 38 illustrates another embodiment of a stabilizing member 300 configured to facilitate operative connection of the actuation shaft 210 to an actuator. The actuation shaft 210 in FIG. 38 is the same as the actuation shaft 210 of FIGS. 36 and 37, but other actuation shafts can be used. The stabilizing member 300 in this illustrated embodiment can allow the actuation shaft 210 to be attached thereto using an interference fit. The stabilizing member 300 in this illustrated embodiment includes the washer 202 and a spherical ball 302 configured to be received in the opening 206 of the washer 202. The spherical ball 302 can be advanced into the opening 206 and held therein by interference fit, similar to the pin 204 of FIGS. 36 and 37. The ball 302 can be cannulated, which can allow the actuation shaft 210 to extend therethrough. The ball 302 can include a longitudinal slot (not shown) therein similar to the slot 208, or other compression mechanisms can be used. Although the washer 202 of FIGS. 36 and 37 is shown in this illustrated embodiment, other washers can be similarly used with the ball 302. Although the drum 216 and the outer shell 212 of FIGS. 36 and 37 is shown in this illustrated embodiment, other drums and outer shells can be similarly used with the stabilizing member 300 of FIG. 38.

Figure 39:
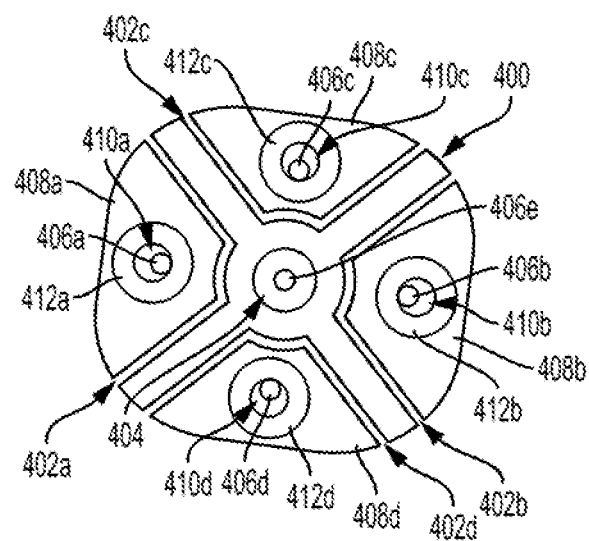
FIG. 39 is a schematic, cross-sectional view of a portion of still another embodiment of a surgical device.
Figure 40:
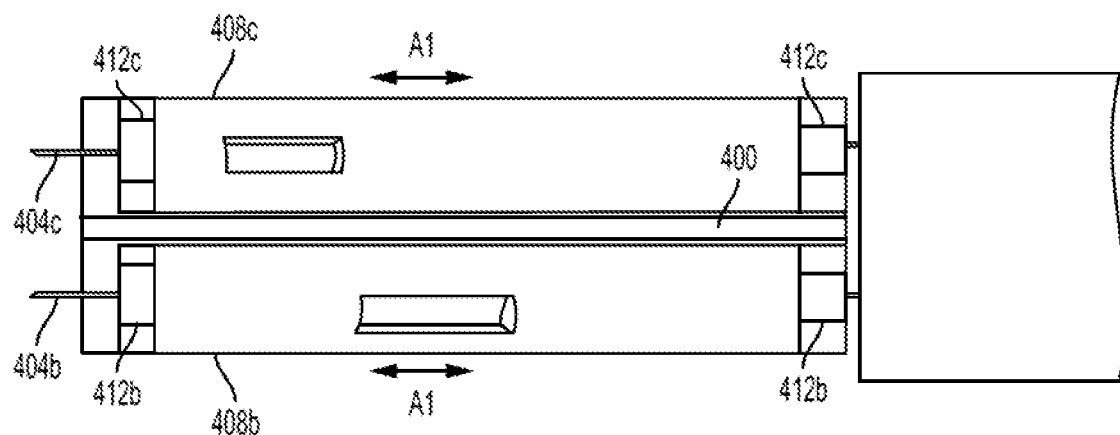
FIG. 40 is a side view of the portion of the surgical device of FIG. 39.
Figure 41:
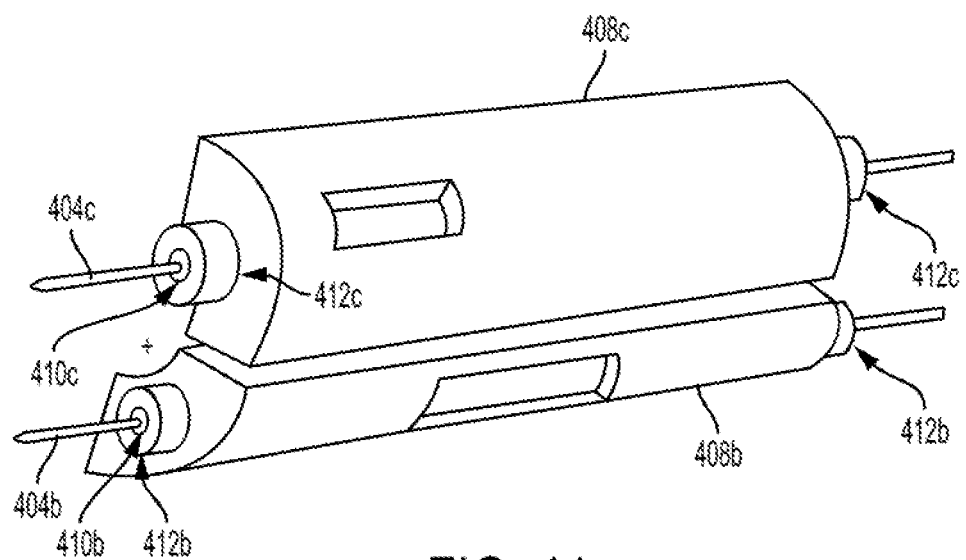
FIG. 41 is a perspective view of select element of the surgical device of FIG. 39.

FIGS. 39-41 illustrate another embodiment of an outer shell 400 configured to stabilize movement of actuation shafts during actuation of various actuators. The outer shell 400 can have a cross-sectional shape defining a plurality of longitudinal channels 402a, 402b, 402c, 402d extending along the outer shell 400. The channels 402a, 402b, 402c, 402d can generally be used similar to the lumens 34a, 34b, 34c, 34d, 34e of the outer shell 34 in the embodiment of FIG. 12 and be configured to slidably receive actuation shafts therein. The outer shell 400 can include at least one inner lumen 404 extending therethrough, which can also each be configured to slidably receive an actuation shaft therein. As in this illustrated embodiment, a first actuation shaft 406a configured to facilitate articulation of an end effector (not shown) can be seated in the first channel 402a, a second actuation shaft 406b configured to facilitate articulation of the end effector can be seated in the second channel 402b, a third actuation shaft 406c configured to facilitate opening/closing of the end effector can be seated in the third channel 402c, a fourth actuation shaft 406d configured to facilitate movement of a cutting element (not shown) along the end effector can be seated in the fourth channel 402d, and a fifth actuation shaft 406e (e.g., an RF cable, etc.) configured to transmit energy can be seated in the inner lumen 404. In an exemplary embodiment, the first and second actuation shafts 406a, 406b configured to facilitate articulation can be slidably seated in ones of the channels 402a, 402b on opposite sides (e.g., left and rights sides) of the outer shell 400, which can facilitate articulation of the end effector in opposite directions (e.g., left and right).

As in this illustrated embodiment, the outer shell 400 can have an "X" cross-sectional shape to define the longitudinal channels 402a, 402b, 402c, 402d, which can accordingly be wedge-shaped. The inner lumen 404 can be a central lumen of the outer shell 400, as in this illustrated embodiment, such that the channels 402a, 402b, 402c, 402d surround the inner lumen 404.

The first, second, third, and fourth actuation shafts 406, 406b, 406c, 406d can be configured to be attached to first, second, third, and fourth guide members 408a, 408b, 408c, 408d, respectively. The guide members 408a, 408b, 408c, 408d can be configured to facilitate sliding of the actuation shafts 406, 406b, 406c, 406d within their respective channels 402a, 402b, 402c, 402d, as the cross-sectional shapes of the actuation shafts 406, 406b, 406c, 406d (circles, in this illustrated embodiment) may not match the cross-sectional shapes of the channels 402a, 402b, 402c, 402d (wedges, in this illustrated embodiment). Cross-sectional shapes of the guide members 408a, 408b, 408c, 408d (wedges, in this illustrated embodiment) can match the cross-sectional shapes of the channels 402a, 402b, 402c, 402d, thereby facilitating sliding movement within the channels 402a, 402b, 402c, 402d. The guide members 408a, 408b, 408c, 408d can have a variety of sizes, shapes, and configurations. As in this illustrated embodiment, each of the guide members 408a, 408b, 408c, 408d can have an inner lumen 410a, 410b, 410c, 410d extending therethrough configured to seat one of the actuation shafts 406, 406b, 406c, 406d therein.

The actuation shafts 406, 406b, 406c, 406d can be fixedly seated within their respective inner lumen 410a, 410b, 410c, 410d so as to be configured to be fixed to and to move in their respective channels 402a, 402b, 402c, 402d with their respective guide members 408a, 408b, 408c, 408d. The actuation shafts 406, 406b, 406c, 406d can be fixedly seated within their respective inner lumen 410a, 410b, 410c, 410d in a variety of ways. As in this illustrated embodiment, each of the guide members 408a, 408b, 408c, 408d can include attachment mechanisms 412a, 412b, 412c, 412d at opposed proximal and distal ends thereof (the first and fourth proximal attachment mechanisms 412a, 412c are not shown in FIGS. 39-41). The attachment mechanisms 412a, 412b, 412c, 412d can be configured to be crimped to their associated one of the actuation shafts 406, 406b, 406c, 406d, thereby securing the actuation shafts 406, 406b, 406c, 406d thereto. Prior to the crimping, the actuation shafts 406, 406b, 406c, 406d can be slidably adjusted within their respective inner lumens 410a, 410b, 410c, 410d, which can help properly position and/or tension the actuation shafts 406, 406b, 406c, 406d.

In an exemplary embodiment, the outer shell 400 can be made from an electrically insulating material, which can help insulate the fifth actuator 406e. In an exemplary embodiment, the outer shell 400 can be made from a material having a low coefficient of friction, which can facilitate sliding of the guide members 408a, 408b, 408c, 408d within the outer shell's channels 402a, 402b, 402c, 402d.

FIGS. 42-45 illustrate another embodiment of an outer shell configured to stabilize movement of actuation shafts during actuation of various actuators. The outer shell can include an inner member 500 and an outer member 502 configured to seat the inner member 500 therein in a cannulated interior 502i thereof. The inner member 500 can generally be configured similar to the outer shell 400 of the embodiment of FIG. 39, having a cross-sectional shape that defines a plurality of longitudinal channels 504a, 504b, 504c, 504d extending along the inner member 500 and having an inner lumen 506 extending therethrough. Each of the channels 504a, 504b, 504c, 504d can be configured to slidably seat one of first, second, third, and fourth actuation shafts 510a, 510b, 510c, 510d therein.

The outer member 502 can have at least one opening 508 formed therein, which in this illustrated embodiment includes at least one longitudinal slot. In an exemplary embodiment, a number of the openings 508 can equal a number of the channels 504a, 504b, 504c, 504d such that each one of the openings 508 is associated with one of the channels 504a, 504b, 504c, 504d and accordingly with one of the actuation shafts 510a, 510b, 510c, 510d.

Figure 42:
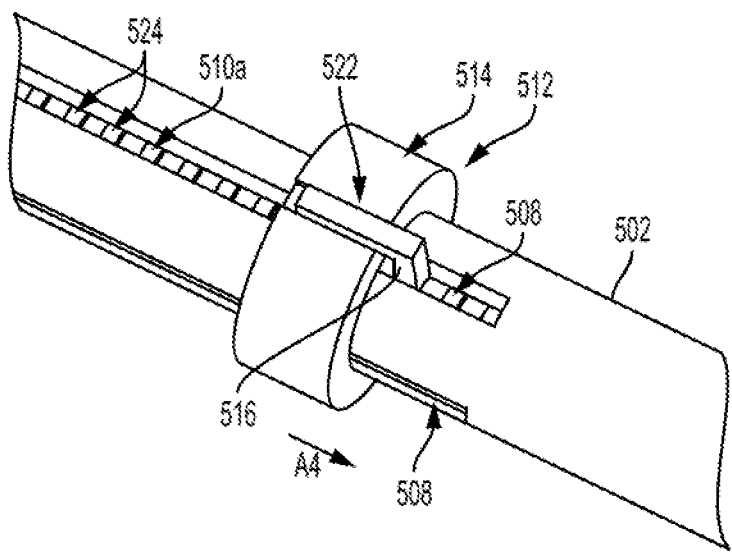
FIG. 42 is a perspective view of a portion of another embodiment of a surgical device.
Figure 43:
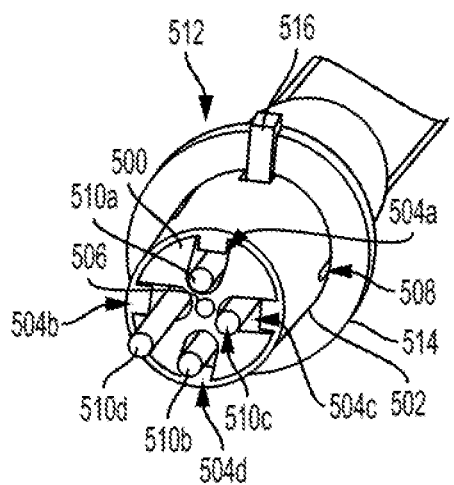
FIG. 43 is another perspective view of the portion of the surgical device of FIG. 42.
Figure 44:
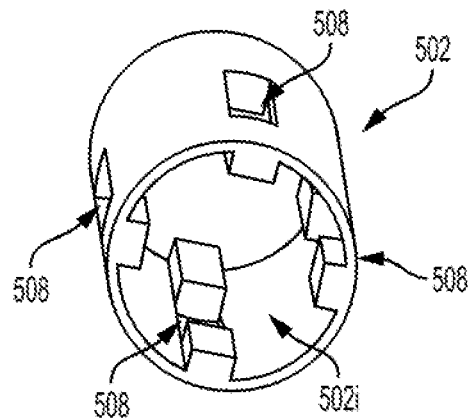
FIG. 44 is a perspective of an outer member of the surgical device of FIG. 42.
Figure 45:
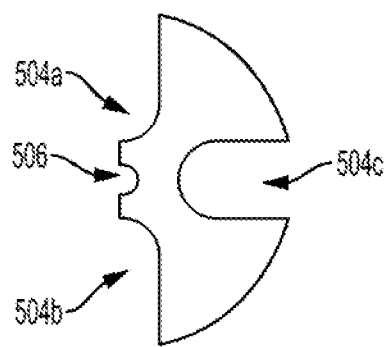
FIG. 45 is a cross-sectional view of an inner member of the surgical device of FIG. 42.
Figure 46:
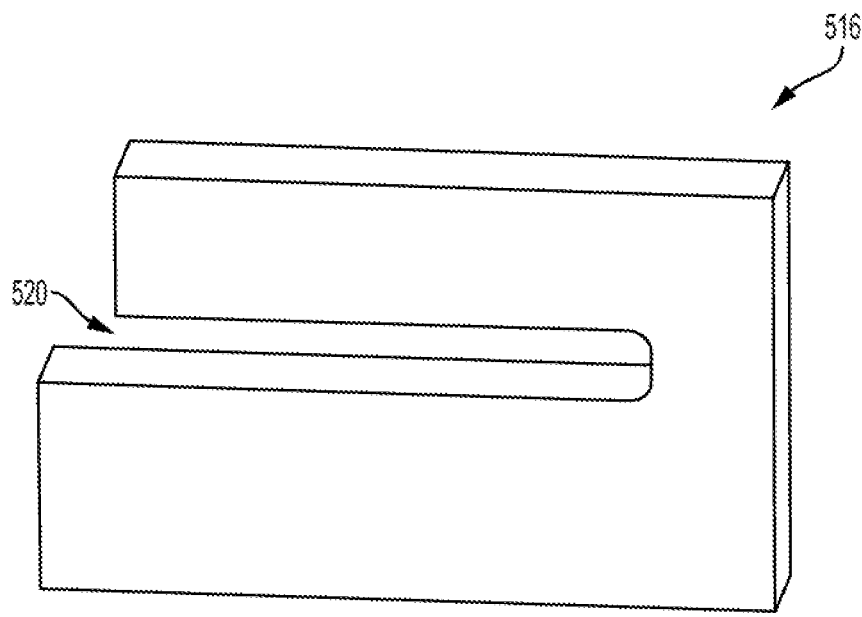
FIG. 46 is a perspective of a block of the surgical device of FIG. 42.
Figure 47:
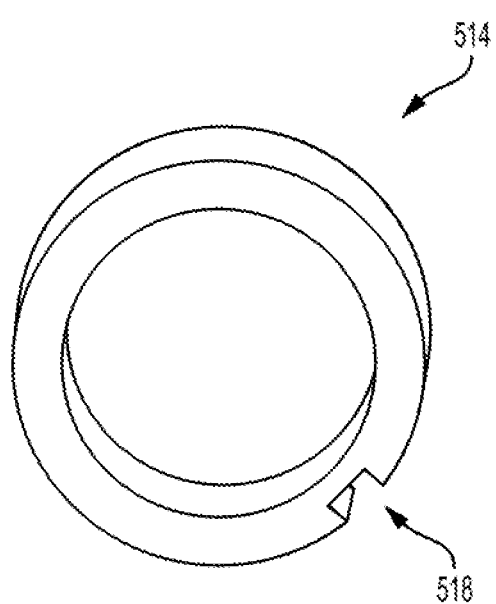
FIG. 47 is a perspective of a washer of the surgical device of FIG. 42.

FIGS. 42 and 43, as well as FIGS. 46 and 47, illustrate another embodiment of a stabilizing member 512 that can be configured to facilitate operative connection of an actuation shaft to an actuator and that can be configured to attach to an outer shell, e.g., the outer shell of FIGS. 42 and 43. The stabilizing member 512 in this illustrated embodiment includes a washer 514 and a block 516 configured to mate with the washer 514 and with an actuation shaft. The washer 514 can include a cut-out 518 formed therein configured to mate with a corresponding cut-out 520 formed in the block 516. When the cut-outs 518, 520 are mated together, and the block 516 positioned within one of the outer shell's openings 508, the washer 514 and the block 516 can be secured together, such as by welding at least one mating edge 522 between the washer 514 and the block 516. The opening 508 in which the block 516 can be seated can allow the stabilizing member 512 to be positioned at a selected position along the outer shell, e.g., by moving longitudinally within the opening 508.

An actuation shaft configured to mate with the stabilizing member 512 can have a plurality of cut-outs formed in an exterior surface thereof that can be configured to mate with the block 516. FIGS. 42 and 43 illustrate the stabilizing member 512 mated to the first actuation shaft 510a with the block 516 mated with a plurality of notches 524 formed in an exterior surface of the first actuation shaft 510a, but other actuation shafts can be similarly mated to stabilizing member 512. The stabilizing member 512 can allow attachment thereof directly to a proximal elongate member without the device including a tube in which the proximal elongate member is seated, as shown in FIG. 42.

The surgical devices described herein can be manufactured in a variety of ways. In embodiments of surgical devices including first and second actuation shafts configured to facilitate articulation of an end effector of the surgical device, where the first and second actuation shafts each include a flexible elongate member, the first and second actuation shafts can be tensioned during manufacturing to take looseness or tolerance out of the system so as to provide a stable shaft assembly and an end effector that can symmetrically articulate. In other words, the first and second actuation shafts, namely the flexible elongate members thereof, can be pre-tensioned during manufacturing to reduce looseness and tolerance. In an exemplary embodiment, the first and second actuation shafts can be pre-tensioned from proximal ends thereof, which can allow the device's actuation mechanism and shaft assembly to otherwise be assembled before the tensioning, can provide more room for the actuation mechanism located distal to where tension is applied to the first and second actuation shafts, and/or can provide better aesthetics in the end effector.

Figure 27:
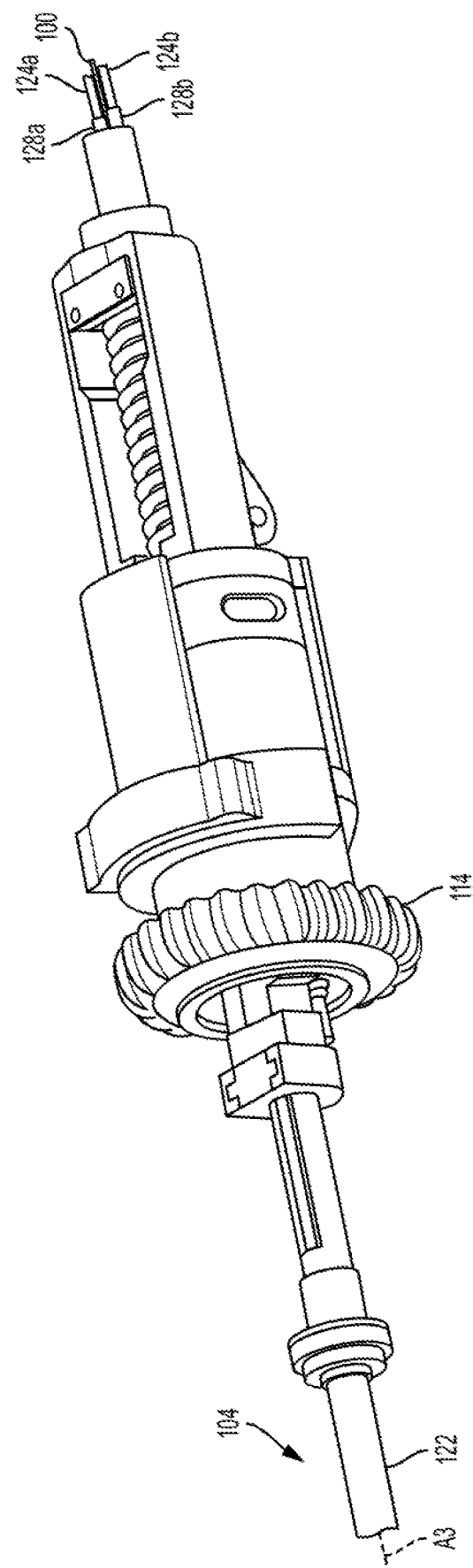
FIG. 27 is a perspective view of another portion of the surgical device of FIG. 25 with select elements of the device omitted for clarity of illustration.
Figure 32:
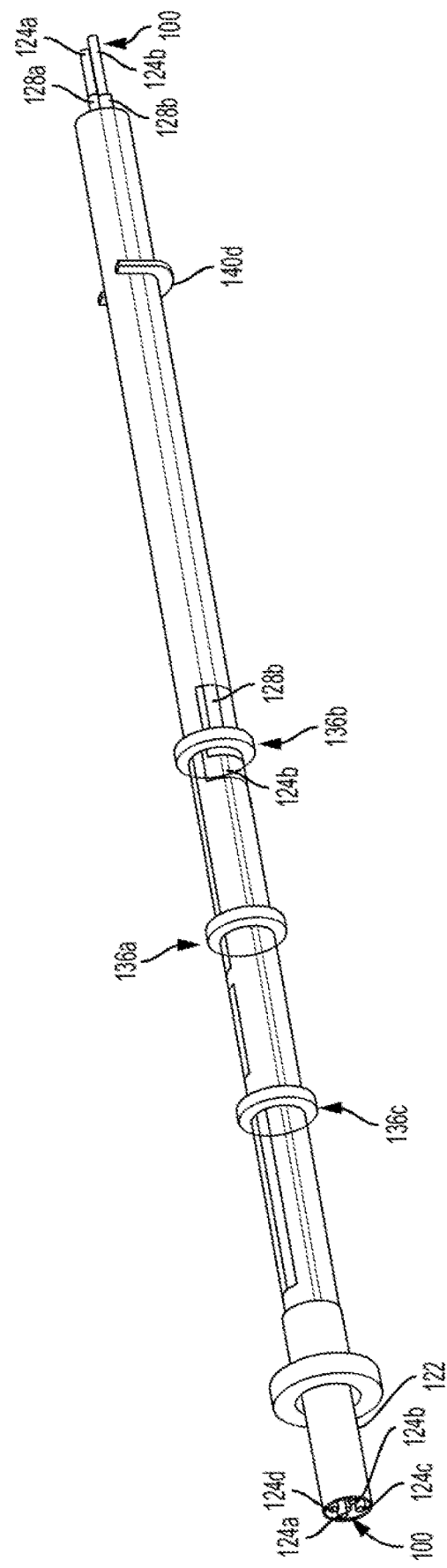
FIG. 32 is a perspective view of yet another portion of the surgical device of FIG. 25 with select elements of the device omitted for clarity of illustration.
Figure 33:
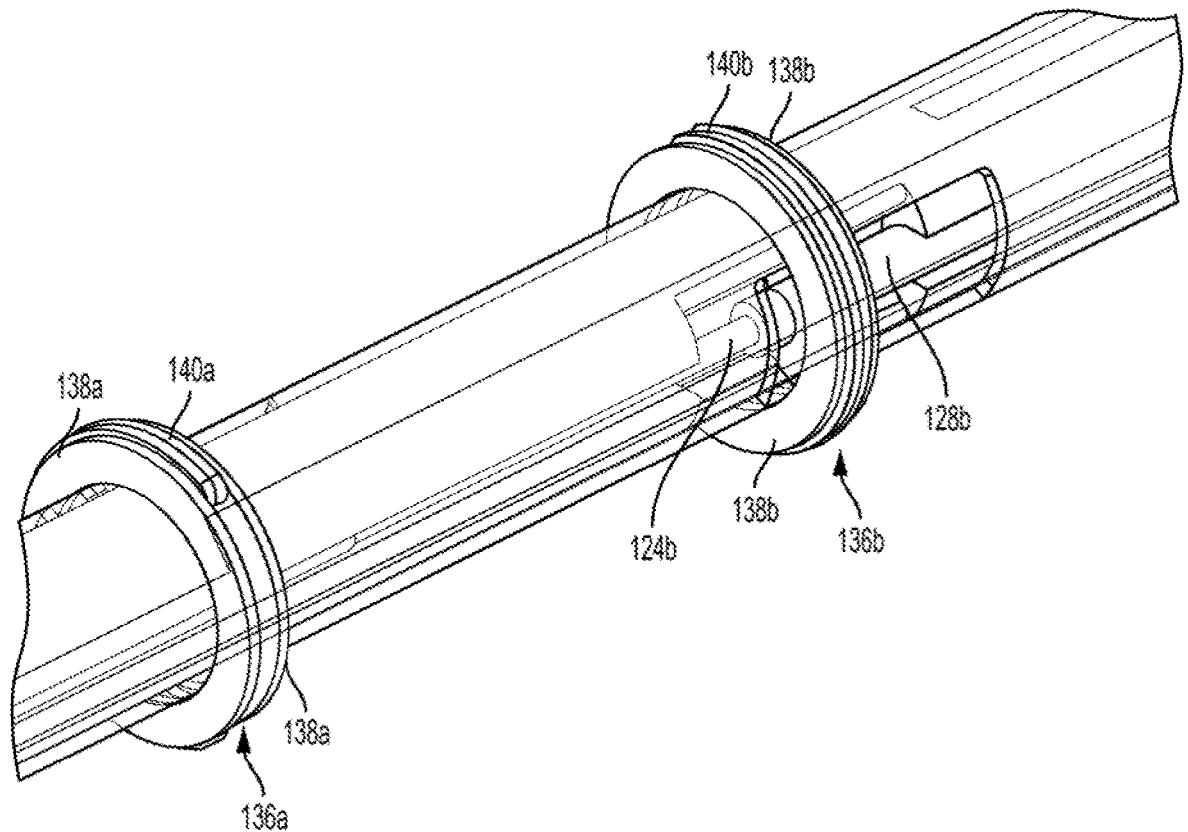
FIG. 33 is an enlarged, partially transparent view of a partial area of the portion of the surgical device of FIG. 32.
Figure 34:
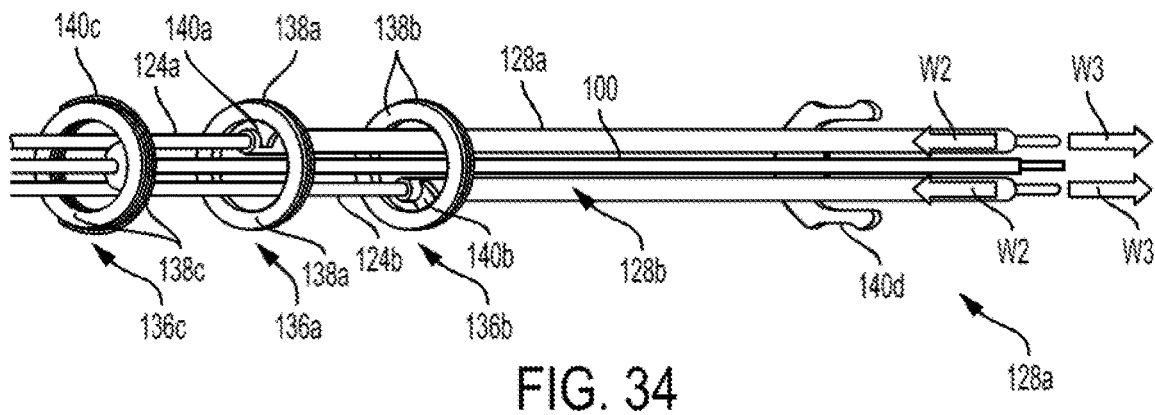
FIG. 34 is a perspective view of select elements of the portion of the surgical device of FIG. 32.

One embodiment of a method of manufacturing a surgical device is described with reference to the device of FIGS. 25-35, but any of the surgical devices disclosed herein can be similarly assembled. The device can be assembled as shown in FIGS. 27 and 32 in any of a variety of ways, as will be appreciated by a person of skill in the art. Distal ends of the first and second actuation shafts can be attached to the end effector 106, such as shown in FIG. 30 with the first distal elongate member 126a attached to a proximal end of the end effector 106, e.g., to a right side of the bottom jaw 108b, and with the second distal elongate member 126b attached to the proximal end of the end effector 106, e.g., to a left side of the bottom jaw 108b.

With the end effector 106 coupled to the shaft assembly and with the shaft assembly coupled to the actuation mechanism, the first and second actuation shafts can be accessible at proximal ends thereof, as shown in FIGS. 27 and 32, where proximal ends of the first and second actuation shafts can be accessible. Then, the first and second tubes 128a, 128b can be moved in a distal direction, e.g., pushed distally, as shown by arrows W2 in FIG. 34, and the first and second proximal elongate members 124a, 124b can be moved simultaneously with the first and second tubes 128a, 128b in a proximal direction, e.g., pulled proximally, as shown by arrows W3 in FIG. 34, such that the first and second tubes 128a, 128b and the first and second proximal elongate members 124a, 124b move relative to one another with the first and second proximal elongate members 124a, 124b sliding longitudinally within their respective ones of the first and second tubes 128a, 128b. The distal movement of the first and second tubes 128a, 128b can push the first and second tubes 128a, 128b against the actuation mechanism, e.g., inside the second actuator's inner lumen, so as to tightly engage the first and second actuation shafts with the second actuator 114. The proximal movement of the first and second proximal elongate members 124a, 124b can pull on the first and second distal elongate members 126a, 126b so as straighten and take out tolerance. A set load can thereby be achieved by the distally directed force applied to the first and second tubes 128a, 128b and the proximally directed force applied to the first and second actuation shafts. At the set load, the first and second tubes 128a, 128b can be attached (e.g., welded, crimped, etc.) to their associated one of the first and second actuation shafts, e.g., to their associated one of the first and second distal elongate members 126a, 126b, as described herein (see, e.g., FIG. 35), to maintain the set load. In other words, tolerances in the shaft assembly system can be neutralized. Each of the first and second tubes 128a, 128b and each of the first and second distal elongate members 126a, 126b can be independently moved during the tensioning process, which can help allow each of the first and second actuation shafts to be accurately tensioned. The first tube 128a and the first proximal elongate member 124a are mentioned above as being tensioned at the same time as the second tube 128b and the second proximal elongate member 124b, but the first tube 128a and the first proximal elongate member 124a can be tensioned and attached together prior to the tensioning of the second tube 128b and the second proximal elongate member 124b, or the second tube 128b and the second proximal elongate member 124b can be tensioned and attached together prior to the tensioning of the first tube 128a and the first proximal elongate member 124a.

In another embodiment of a method of manufacturing a surgical device, manufacturing a surgical device including the stabilizing member 512 and the outer shell of FIGS. 42 and 43 can include, with the first actuation shaft 510a being slidably seated in the outer shell, moving the washer 514 in a proximal direction, as indicated by an arrow A4 in FIG. 42 to securely mate the block 516 thereto prior to welding or otherwise fixing the washer 514 and the block 516 together.

In manufacturing a surgical device including an outer shell, the outer shell can be formed in a variety of ways. In some embodiments, the outer shell can be formed using extrusion. In other embodiments, the outer shell can be formed using pultrusion. Pultrusion can be less expensive than other manufacturing processes and/or can facilitate stiffening of the device (e.g., a shaft assembly thereof) due to materials that can be pultruded. Pultrusion can eliminate the need to heat shrink elements of the surgical device, which can allow the device to be sterilized using a sterilization technique such as Ethylene Oxide (EO) sterilization, which can damage heat shrinking.

FIGS. 48-54 illustrate an embodiment a surgical device including an outer shell 622 that can be formed using pultrusion. The device of FIGS. 48-54 can generally be configured and used similar to the surgical device 2 of the embodiment of FIGS. 1-24 and similar to other embodiments of surgical devices described herein. The device can include a proximal handle portion 602, a shaft assembly 604 extending distally from the handle portion 602, and an end effector 606 including a pair of opposed jaws 608a, 608b and being coupled to a distal end of the shaft assembly 604 at a pivot joint 610. The device in this illustrated embodiment includes a conductive lead 600 and can hence be powered.

The handle portion 602 can include a main housing 612, which can house a variety of elements therein and can have some elements accessible outside thereof, such as a first actuator 616 configured to effect the opening and closing of the opposed jaws 608a, 608b, a second actuator 614 configured to effect articulation of the end effector 606, a third actuator (not shown in FIGS. 48-54) configured to rotate the shaft assembly 604 and the end effector 606 about a longitudinal axis A5 of the shaft assembly 604, a fourth actuator 618 configured to translate a cutting element (obscured in FIGS. 48-54) along the end effector 606, and a fifth actuator 620 configured to turn on and off the application of energy, which includes RF energy in this illustrated embodiment.

Figure 48:
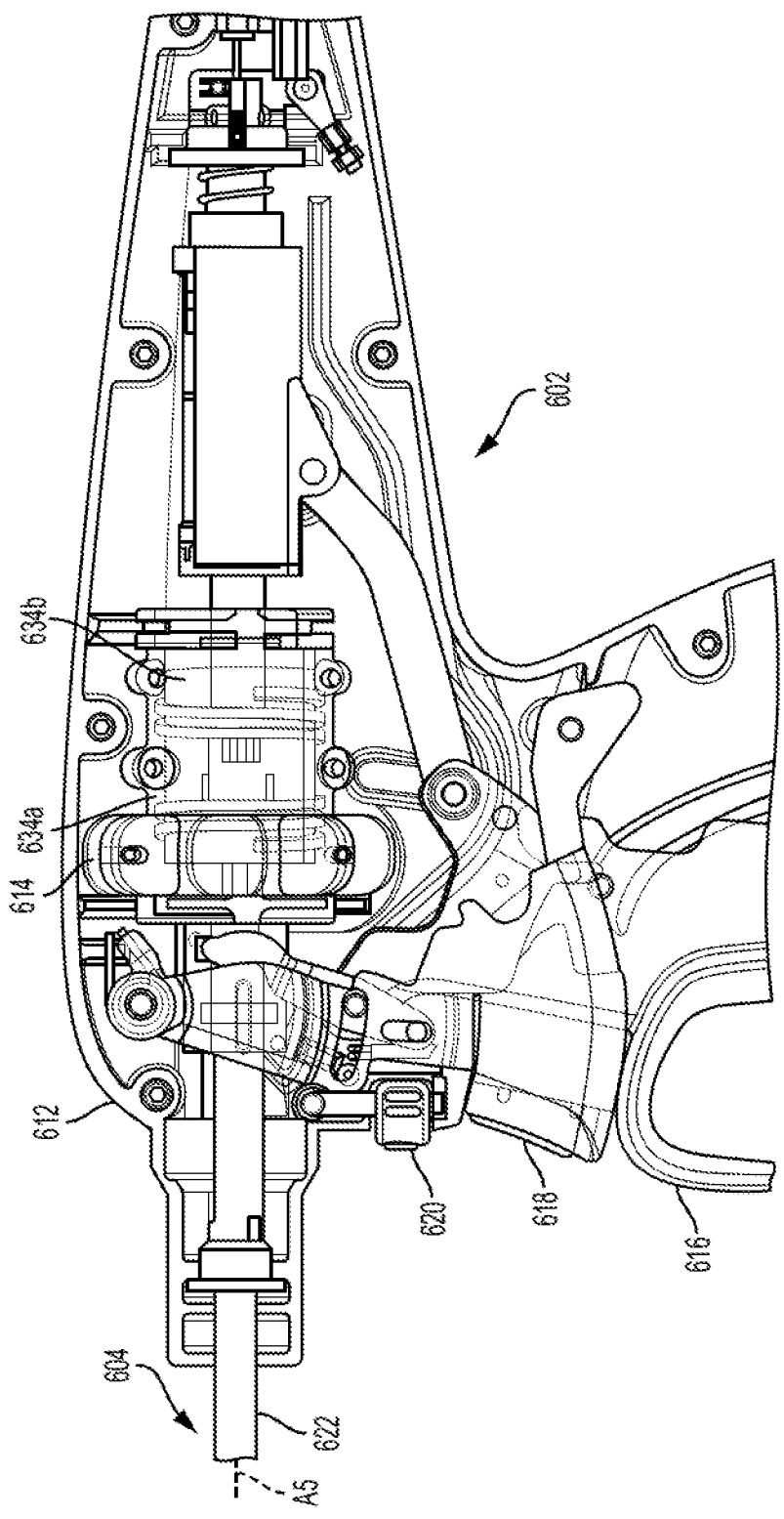
FIG. 48 is a side, partially transparent view of a portion of another embodiment of a surgical device with select elements of the device omitted for clarity of illustration.
Figure 49:
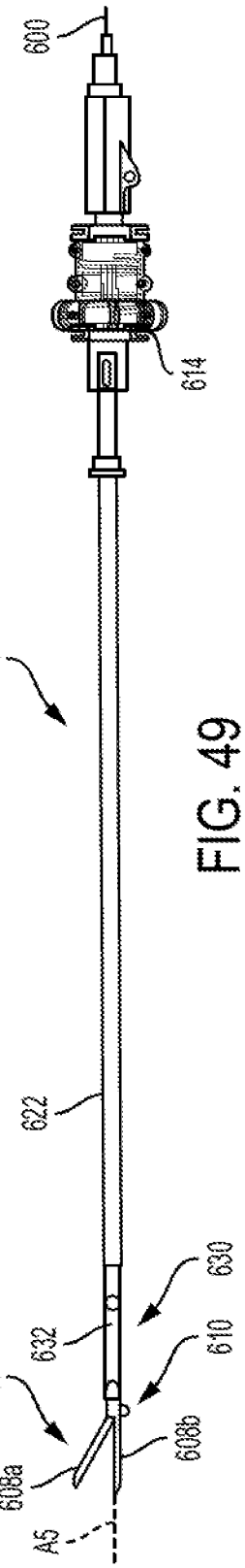
FIG. 49 is a side view of another portion of the surgical device of FIG. 48 with select elements of the device omitted for clarity of illustration.
Figure 50:
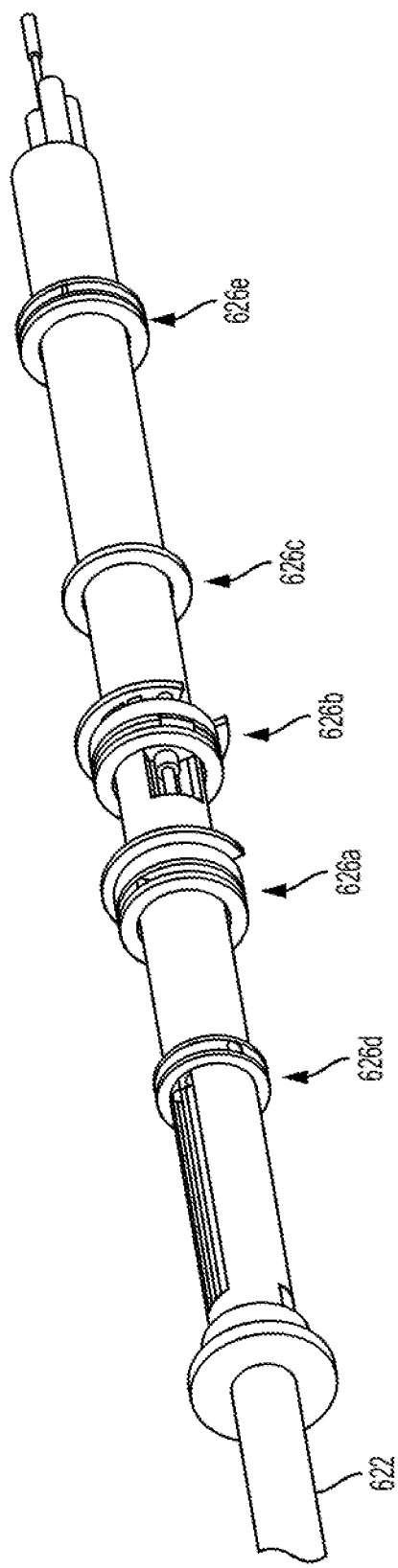
FIG. 50 is a perspective view of yet another portion of the surgical device of FIG. 48 with select elements of the device omitted for clarity of illustration.
Figure 51:
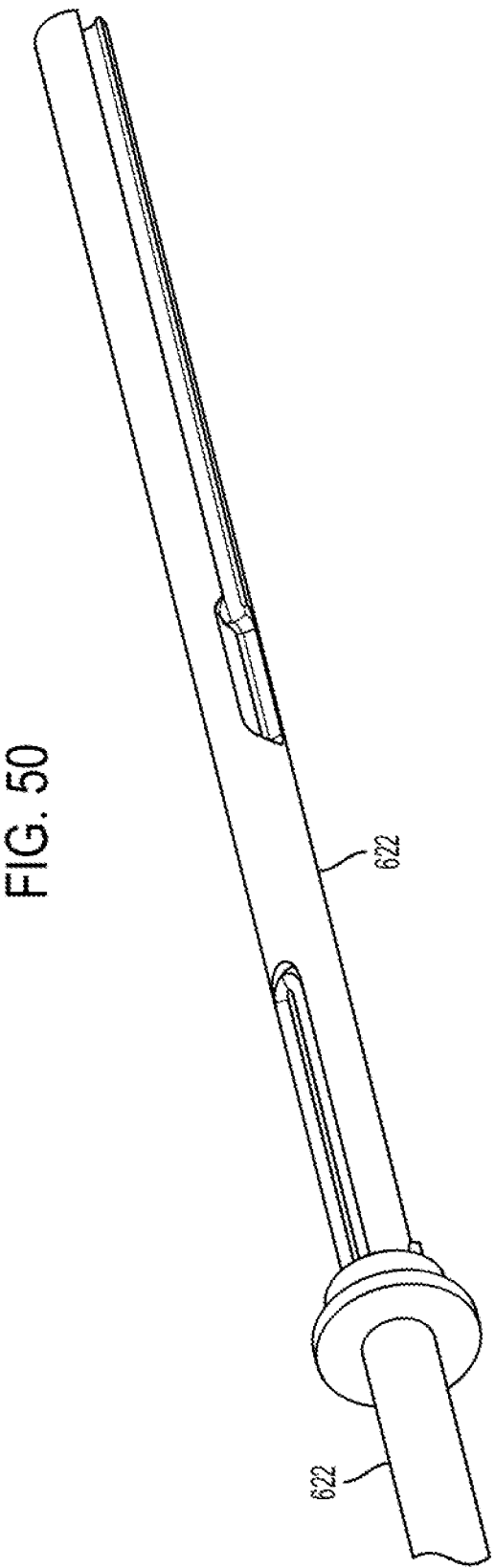
FIG. 51 is a perspective view of the portion of the surgical device of FIG. 50 with select elements of the device omitted for clarity of illustration.
Figure 52:
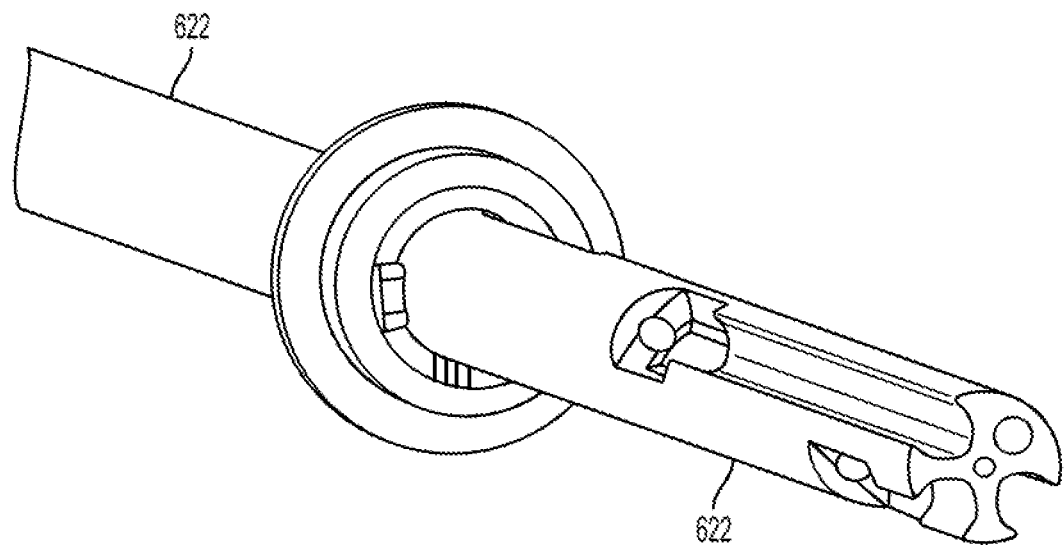
FIG. 52 is a perspective view of a portion of the device of FIG. 50.
Figure 53:
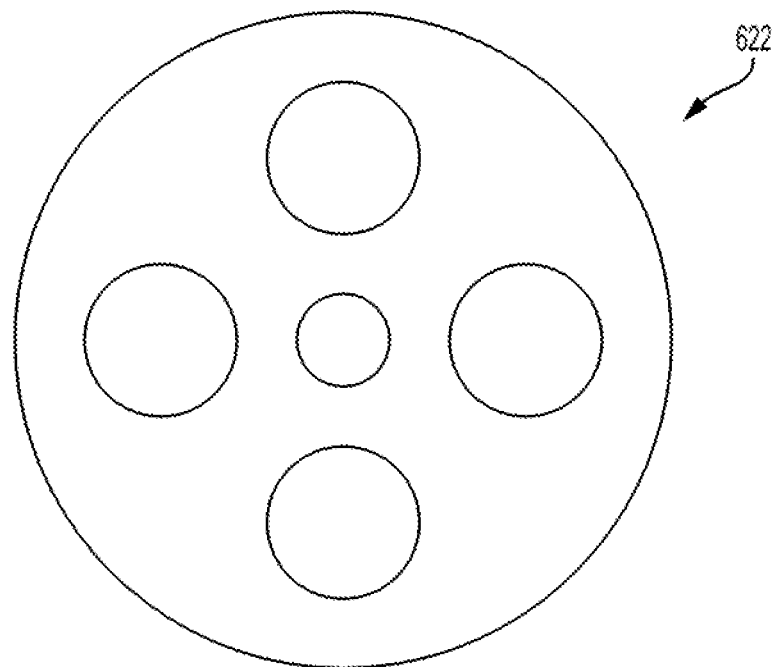
FIG. 53 is a cross-sectional view of an outer shell of the portion of the surgical device of FIG. 51.
Figure 54:
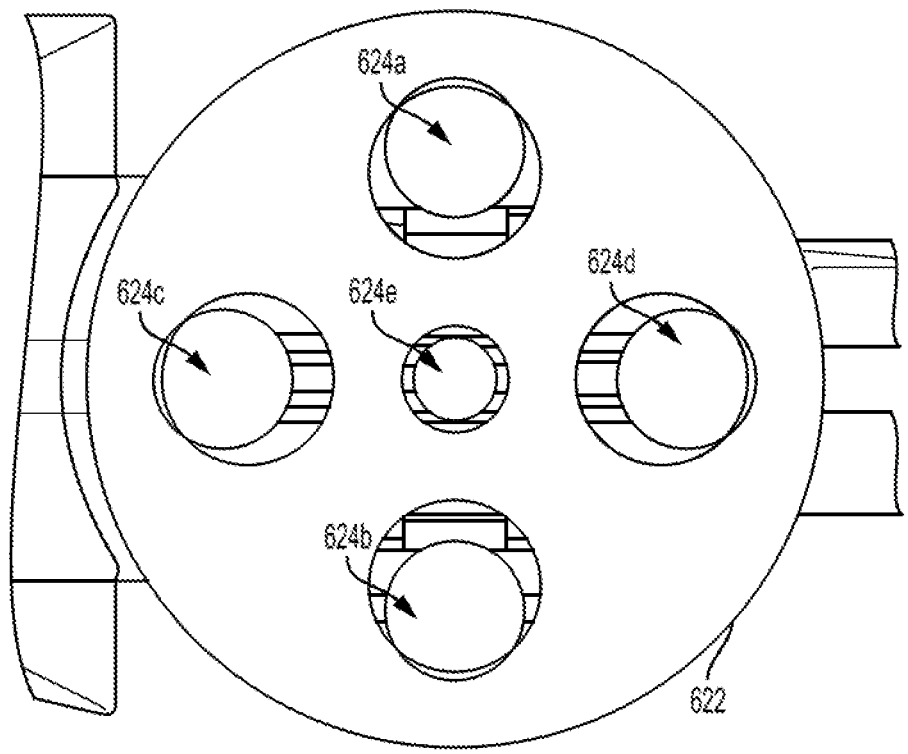
FIG. 54 is a cross-sectional view of the portion of the surgical device of FIG. 50.

The second actuator 614 configured to effect articulation of the end effector 606 can be operatively connected to an actuation mechanism, which can include first and second drums 634a, 634b. The second actuator 614 and the first and second drums 634a, 634b can be threadably engaged, as shown in FIGS. 48 and 49. FIG. 49 illustrates the end effector 606 in an unarticulated position, e.g., at a zero angle relative to the longitudinal axis A5.

The shaft assembly 604 can include the outer shell 622 and at least one actuation shaft extending between the handle portion 602 and the end effector 606. In this illustrated embodiment, the device includes a first actuation shaft 624a, a second actuation shaft 624b, a third actuation shaft 624c, a fourth actuation shaft 624d, and a fifth actuation shaft 624e. Each of the actuation shafts 624a, 624b, 624c, 624d, 624e can extend through a bend region 630 of the device that includes a flexible outer shell 632. As mentioned above, the outer shell 622 can be formed using pultrusion. In an exemplary embodiment, the outer shell 622 can be made from a composite material, which can facilitate the pultrusion process. The composite material can have a relatively high modulus, which can facilitate the pultrusion process. For example, the modulus of the composite material can be in a range of about four million to about eight million, e.g., about seven million.

The device can include a first stabilizing member 626a configured to couple the first actuation shaft 624a to the second actuator 614, a second stabilizing member 626b configured to couple the second actuation shaft 624b to the second actuator 614, a third stabilizing member 626c configured to couple the third actuation shaft 624c to the first actuator 616, a fourth stabilizing member 626d configured to couple the fourth actuation shaft 624d to the fourth actuator 618, and a fifth stabilizing member 626e including configured to couple the fifth actuation shaft 624e to the fifth actuator 620.

Figure 55:
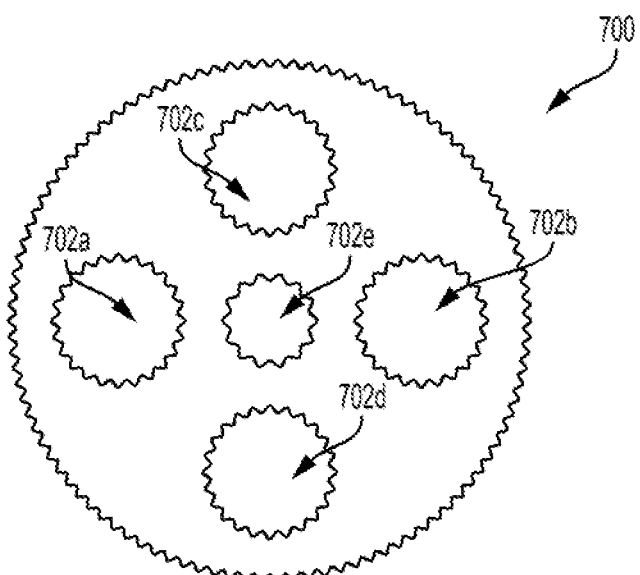
FIG. 55 is a cross-sectional view of another embodiment of an outer shell.

FIG. 55 illustrates another embodiment of an outer shell 700 including a plurality of inner lumens 702a, 702b, 702c, 702d, 702e. The outer shell 700 can be used in any of the surgical devices described herein and can generally be configured and used similar to other outer shells described herein. In this illustrated embodiment, the outer shell 700 has a splined outer surface, and each of the inner lumens 702a, 702b, 702c, 702d, 702e are defined by a splined surface. The splined surfaces can facilitate cleaning and sterilization using a process such as ethylene oxide. The outer shell 700 of this illustrated embodiment can be formed in a variety of ways, such as pultrusion or extrusion. In contrast, the embodiment of the outer shell 622 illustrated in FIG. 53 has an unsplined outer surface, and each of its inner lumens are defined by an unsplined surface.

A person skilled in the art will appreciate that the present invention has application in conventional minimally-invasive and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method, comprising:
advancing a first elongate member into a first passageway of a first tube of a shaft assembly;
coupling the first elongate member to an end effector;
with the first elongate member coupled to the end effector and within the first passageway, tensioning the first elongate member in a distal direction and tensioning the first tube in a proximal direction so that the first tube pushes proximally against an actuation mechanism and so that the first elongate member and the first tube are simultaneously tensioned;
attaching the tensioned first elongate member to the tensioned first tube so that the tensioned first elongate member and the tensioned first tube are in a fixed position relative to one another;
advancing a second elongate member into a second passageway of a second tube of the shaft assembly;
coupling the second elongate member to the end effector;
with the second elongate member coupled to the end effector and within the second passageway, simultaneously tensioning the second elongate member in the distal direction and tensioning the second tube in the proximal direction so that the second tube pushes proximally against the actuation mechanism and so that the second elongate member and the second tube are simultaneously tensioned; and
attaching the tensioned second elongate member to the tensioned second tube so that the tensioned second elongate member and the tensioned second tube are in a fixed position relative to one another.

2. The method of claim 1, further comprising:
prior to the simultaneous tensioning of the first elongate member and the first tube, attaching a proximal end of a first flexible elongate band to a distal end of the first elongate member;
prior to the simultaneous tensioning of the second elongate member and the second tube, attaching a proximal end of a second flexible elongate band to a distal end of the second elongate member;
attaching a distal end of the first flexible elongate band to the end effector; and
attaching a distal end of the second flexible elongate band to the end effector.

3. A method of assembling a surgical device, comprising:
slidably adjusting a position of a first elongate member within a first inner lumen extending through a first tubular member;
slidably adjusting a position of a second elongate member within a second inner lumen extending through a second tubular member;
coupling an end effector to the first and second elongate members, the end effector being configured to manipulate tissue;
coupling an actuation mechanism to the first and second tubular members;
after adjusting the position of the first elongate member, after coupling the first elongate member to the end effector, and after coupling an actuation mechanism to the first and second tubular members, moving the first elongate member in a proximal direction and moving the first tubular member in a distal direction so as to achieve a first tension load;

at the achieved first tension load, securing the first elongate member and the first tubular member in a fixed position relative to one another;

after adjusting the position of the second elongate member, after coupling the second elongate member to the end effector, and after coupling an actuation mechanism to the first and second tubular members, moving the second elongate member in the proximal direction and moving the second tubular member in the distal direction so as to achieve a second tension load; and at the achieved second tension load, securing the second elongate member and the second tubular member in a fixed position relative to one another;

wherein the actuation mechanism coupled to the first and second tubular members is configured to be selectively actuated so as to cause the first elongate member and the first tube to move as a unit in one of the proximal and distal directions and to cause the second elongate member and the second tube to move as a unit in the other of the proximal and distal directions, thereby causing articulation of the end effector.

4. The method of claim 3, wherein securing the first elongate member and the first tubular member in the fixed position relative to one another includes one of crimping the first elongate member and the first tubular member together and welding the first elongate member and the first tubular member together.

5. The method of claim 3, further comprising:

securing a distal end of a first rigid rod to a proximal end of a first flexible band to form the first elongate member;

securing a distal end of the first flexible band to the end effector;

securing a distal end of a second rigid rod to a proximal end of a second flexible band to form the second elongate member; and securing a distal end of the second flexible band to the end effector;

wherein the first band is configured to move with the first elongate member and the first tube as a unit in the one of the proximal and distal directions, and the second band is configured to move with the second elongate member and the second tube as a unit in the other of the proximal and distal directions.

* * * * *